(12) United States Patent
He et al.

(10) Patent No.: US 11,740,692 B2
(45) Date of Patent: Aug. 29, 2023

(54) OPTICAL EYE TRACKING

(71) Applicant: Shenzhen Goodix Technology Co., Ltd., Shenzhen (CN)

(72) Inventors: Yi He, San Diego, CA (US); Bo Pi, Carlsbad, CA (US)

(73) Assignee: SHENZHEN GOODIX TECHNOLOGY CO., LTD., Shenzhen (CN)

( * ) Notice: Subject to any disclaimer, the term of this patent is extended or adjusted under 35 U.S.C. 154(b) by 302 days.

(21) Appl. No.: 14/537,818

(22) Filed: Nov. 10, 2014

(65) Prior Publication Data

US 2015/0199006 A1 Jul. 16, 2015

Related U.S. Application Data

(60) Provisional application No. 62/037,035, filed on Aug. 13, 2014, provisional application No. 61/902,222, filed on Nov. 9, 2013.

(51) Int. Cl.
| | |
|---|---|
| *G06F 3/01* | (2006.01) |
| *A61B 3/113* | (2006.01) |
| *A61B 3/00* | (2006.01) |

(52) U.S. Cl.
CPC ............ *G06F 3/013* (2013.01); *A61B 3/0041* (2013.01); *A61B 3/113* (2013.01)

(58) Field of Classification Search
CPC combination set(s) only.
See application file for complete search history.

(56) References Cited

U.S. PATENT DOCUMENTS

| | | | |
|---|---|---|---|
| 3,864,030 | A | 2/1975 | Cornsweet |
| 5,610,673 | A | 3/1997 | Rafal et al. |
| | | (Continued) | |

FOREIGN PATENT DOCUMENTS

| | | | |
|---|---|---|---|
| CN | 1937956 | A | 3/2007 |
| CN | 101779960 | A | 7/2010 |
| | (Continued) | | |

OTHER PUBLICATIONS

International Search Report and Written Opinion dated Apr. 16, 2015 for International Application No. PCT/US2014/067827, filed on Nov. 28, 2014 (10 pages).

(Continued)

*Primary Examiner* — William Boddie
*Assistant Examiner* — Alecia D English
(74) *Attorney, Agent, or Firm* — Perkins Coie LLP

(57) ABSTRACT

Methods, systems, and devices are disclosed for optical sensing and tracking of eye movement. In one aspect, a method for tracking the movement of an eye includes emitting a first modulated light and a second modulated light toward an eye of a user, wherein the first modulated light and the second modulated light have substantially the same modulation frequency, but the modulation phases of the two modulated lights are substantially opposite to each other; receiving at a photodetector module a returned light including at least a partial retroreflected light from the eye of the user based on the first and second modulated lights; and processing the output signal from the photodetector module to determine positional and dimensional parameters of the eye of the user based at least on the partial retroreflected light corresponding to the first and second modulated lights.

14 Claims, 40 Drawing Sheets

(56) References Cited

U.S. PATENT DOCUMENTS

| | | | |
|---|---|---|---|
| 5,621,457 A * | 4/1997 | Ishiwaka | G01C 21/3641 |
| | | | 348/78 |
| 5,861,940 A * | 1/1999 | Robinson | A61B 3/113 |
| | | | 351/205 |
| 5,956,124 A | 9/1999 | Dan | |
| 6,373,961 B1 | 4/2002 | Richardson et al. | |
| 6,542,624 B1 | 4/2003 | Oda | |
| 6,634,749 B1 | 10/2003 | Morrison et al. | |
| 7,380,938 B2 | 6/2008 | Chmielewski, Jr. et al. | |
| 8,878,773 B1 * | 11/2014 | Bozarth | G06K 9/00604 |
| | | | 345/156 |
| 9,323,325 B2 | 4/2016 | Perez et al. | |
| 2002/0041259 A1 | 4/2002 | Lewis et al. | |
| 2002/0093645 A1 | 7/2002 | Heacock | |
| 2003/0038754 A1 | 2/2003 | Goldstein et al. | |
| 2004/0032952 A1 | 2/2004 | Pinto et al. | |
| 2004/0170304 A1 | 9/2004 | Haven et al. | |
| 2005/0073136 A1 | 4/2005 | Larsson et al. | |
| 2005/0175218 A1 * | 8/2005 | Vertegaal | A61B 3/113 |
| | | | 382/103 |
| 2005/0199783 A1 * | 9/2005 | Wenstrand | G06V 40/19 |
| | | | 250/214.1 |
| 2006/0093998 A1 | 5/2006 | Vertegaal | |
| 2006/0110008 A1 | 5/2006 | Vertegaal et al. | |
| 2006/0256083 A1 | 11/2006 | Rosenberg | |
| 2007/0040908 A1 * | 2/2007 | Cleveland | G06V 40/193 |
| | | | 348/78 |
| 2007/0159599 A1 | 7/2007 | Yamada | |
| 2007/0197886 A1 * | 8/2007 | Naganuma | A61B 5/0095 |
| | | | 600/322 |
| 2008/0044188 A1 | 2/2008 | Kagawa et al. | |
| 2009/0046249 A1 | 2/2009 | Northcott et al. | |
| 2009/0046899 A1 | 2/2009 | Northcott et al. | |
| 2009/0103048 A1 * | 4/2009 | Tsukiji | A61B 3/14 |
| | | | 351/246 |
| 2009/0141339 A1 | 6/2009 | Yurlov et al. | |
| 2009/0192961 A1 | 7/2009 | Fithian et al. | |
| 2010/0079508 A1 | 4/2010 | Hodge et al. | |
| 2010/0208207 A1 * | 8/2010 | Connell, II | G06K 9/0061 |
| | | | 351/210 |
| 2011/0069277 A1 | 3/2011 | Blixt et al. | |
| 2011/0090459 A1 | 4/2011 | Rathjen et al. | |
| 2011/0109880 A1 | 5/2011 | Nummela | |
| 2011/0170060 A1 | 7/2011 | Gordon | |
| 2011/0182472 A1 * | 7/2011 | Hansen | A61B 3/113 |
| | | | 382/103 |
| 2012/0032921 A1 * | 2/2012 | Lin | G06F 3/0428 |
| | | | 345/175 |
| 2012/0105486 A1 | 5/2012 | Lankford et al. | |
| 2012/0256967 A1 * | 10/2012 | Baldwin | G06F 3/0485 |
| | | | 345/684 |
| 2013/0050070 A1 | 2/2013 | Lewis et al. | |
| 2013/0050432 A1 | 2/2013 | Perez et al. | |
| 2013/0077049 A1 | 3/2013 | Bohn | |
| 2013/0094712 A1 | 4/2013 | Said | |
| 2013/0176208 A1 * | 7/2013 | Tanaka | G06F 3/013 |
| | | | 345/156 |
| 2013/0176533 A1 | 7/2013 | Raffle et al. | |
| 2013/0188834 A1 * | 7/2013 | Ebisawa | A61B 3/113 |
| | | | 382/103 |
| 2014/0058483 A1 * | 2/2014 | Zao | A61B 5/378 |
| | | | 607/88 |
| 2014/0075349 A1 | 3/2014 | Yun et al. | |
| 2014/0098198 A1 | 4/2014 | Lee et al. | |
| 2014/0354514 A1 | 12/2014 | Aronsson | |
| 2014/0361957 A1 | 12/2014 | Hua et al. | |
| 2015/0070273 A1 | 3/2015 | He et al. | |
| 2015/0145777 A1 | 5/2015 | He et al. | |

FOREIGN PATENT DOCUMENTS

| | | |
|---|---|---|
| CN | 101901485 A | 12/2010 |
| JP | 2013-215549 A | 10/2013 |
| KR | 10-2011-0116580 A | 10/2011 |
| KR | 10-2013-0043369 A | 4/2013 |
| WO | 2005/046465 A1 | 5/2005 |
| WO | 2010/118292 A1 | 10/2010 |
| WO | 2012/055444 A1 | 5/2012 |
| WO | 2015/038810 A2 | 3/2015 |
| WO | 2015/081325 A1 | 6/2015 |

OTHER PUBLICATIONS

International Search Report and Written Opinion dated Feb. 25, 2015 for International Application No. PCT/US2014/055243, filed on Sep. 11, 2014 (10 pages).
International Search Report and Written Opinion dated Feb. 19, 2015 for International Application No. PCT/US2014/064884, filed on Nov. 10, 2014 (12 pages).
Chinese Office Action dated Apr. 17, 2018 for Chinese Patent Application No. 201480072610.0, filed on Nov. 10, 2014 (8 pages).
European Communication dated Jul. 12, 2017 for European Patent Application No. 14859463.3, filed on Nov. 10, 2014 (8 pages).
European Communication dated Jun. 8, 2017 for European Patent Application No. 14866657.1, filed on Nov. 28, 2014 (9 pages).
Korean Office Action dated Jul. 31, 2017 for Korean Patent Application No. 10-2016-7016972, filed on Nov. 28, 2014 (6 pages).
Korean Office Action dated Sep. 18, 2017 for Korean Patent Application No. 10-2016-7015297, filed on Nov. 10, 2014 (11 pages).
Examination Report dated Jul. 25, 2019 for Indian Patent Application No. 201627019074 (6 pages).
Office Action dated Oct. 21, 2019 for Chinese Patent Application No. 201480065120.8 (3 pages).
Research of Remote Gaze Tracking Technique with Near IR Illumination, Mar. 2012 (abstract only).

* cited by examiner

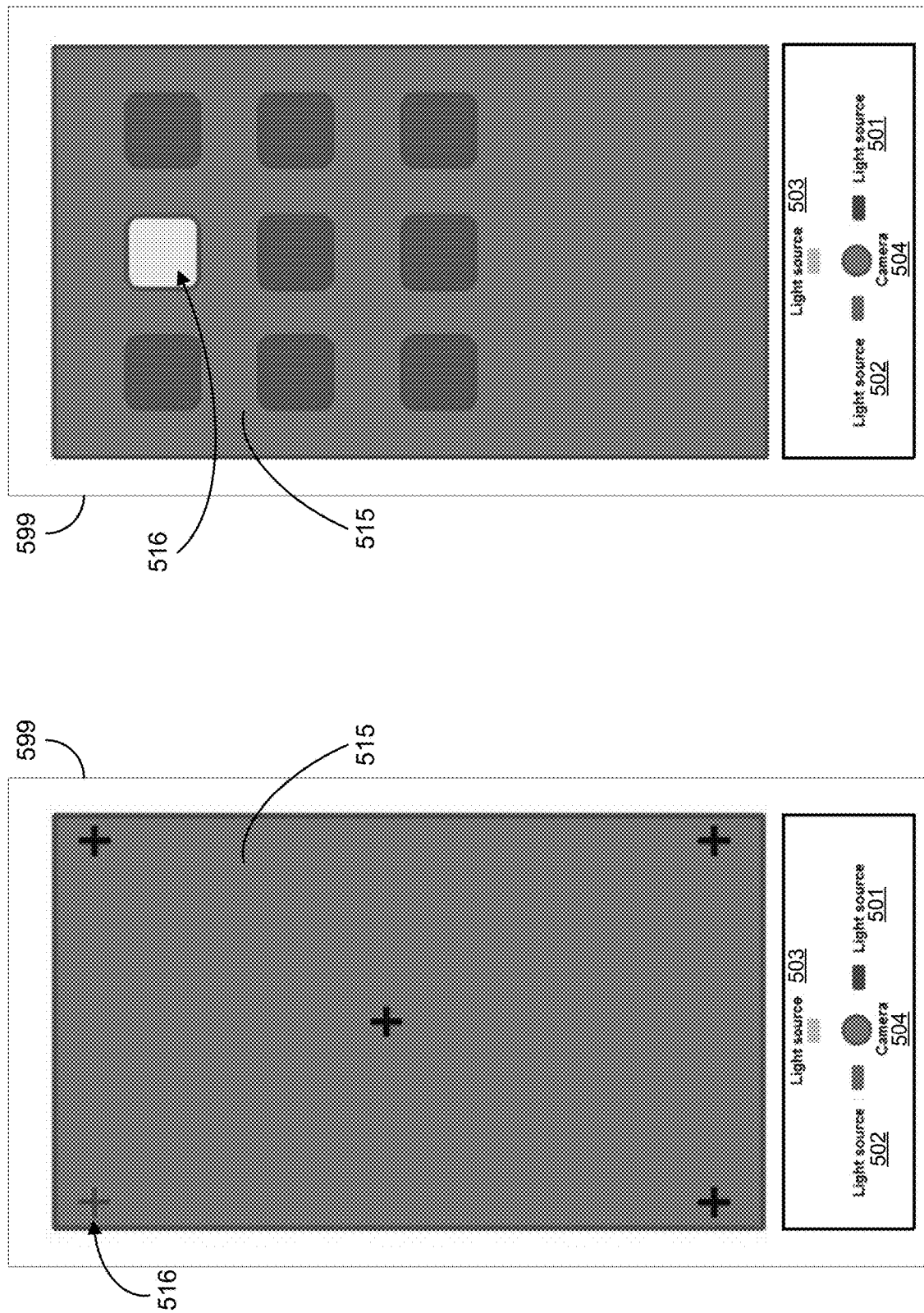

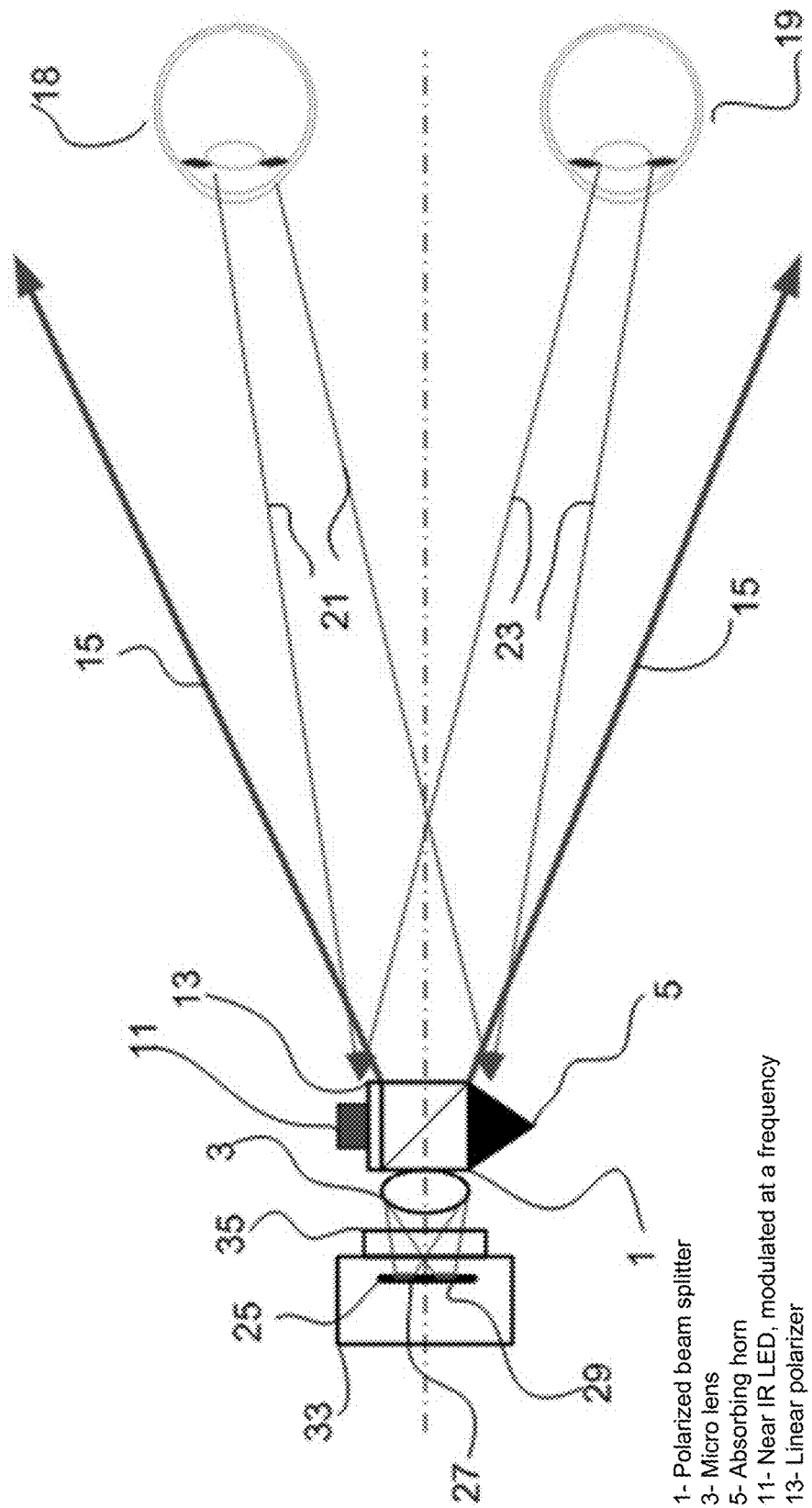

FIG. 9

1- Polarized beam splitter
3- Micro lens
5- Absorbing horn
11- Near IR LED, modulated at a frequency
13- Linear polarizer
15- LED irradiated light beam
18- Right eye
19- Left eye
21- Retro reflected light beam from right eye
23- Retro reflected light beam from left eye
25- Detector sensitive array
27- Image spot of left eye
29- Image spot of right eye
33- Detector assembly with micro processors
35- Band pass filter

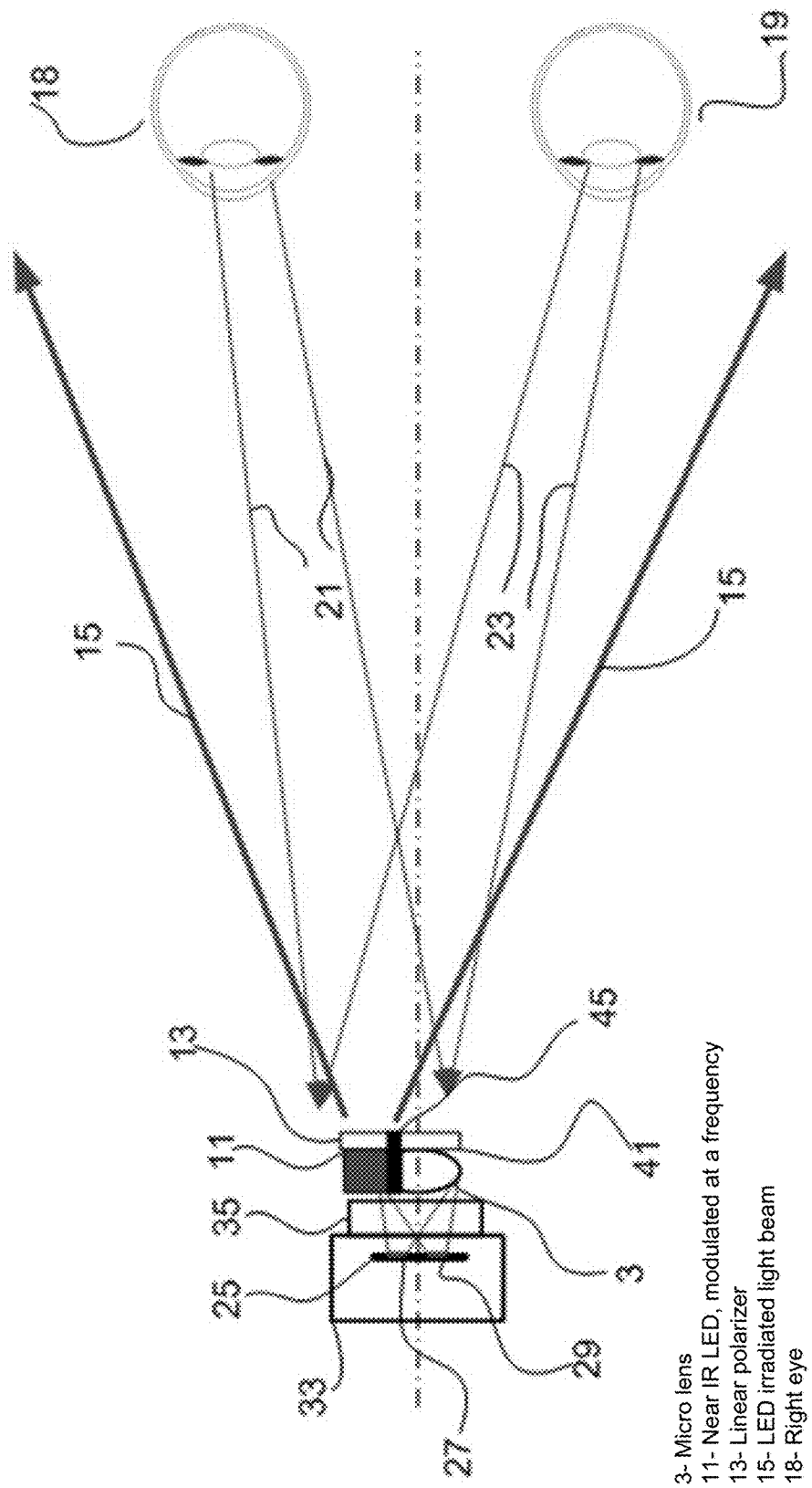

FIG. 10

3- Micro lens
11- Near IR LED, modulated at a frequency
13- Linear polarizer
15- LED irradiated light beam
18- Right eye
19- Left eye
21- Retro reflected light beam from right eye
23- Retro reflected light beam from left eye
25- Detector sensitive array
27- Image spot of left eye
29- Image spot of right eye
33- Detector assembly with micro processors
35- Band pass filter
41- Linear polarizer, receiving
45- Light blocker wall

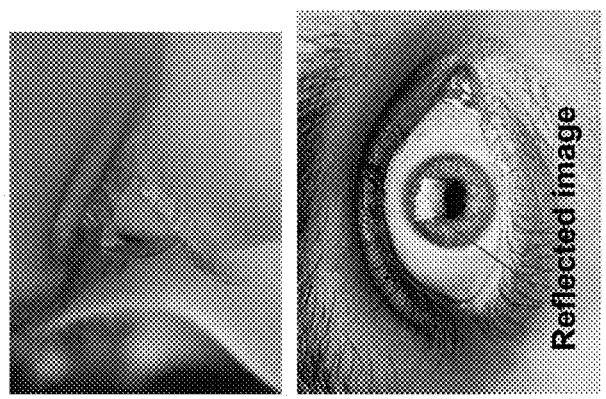
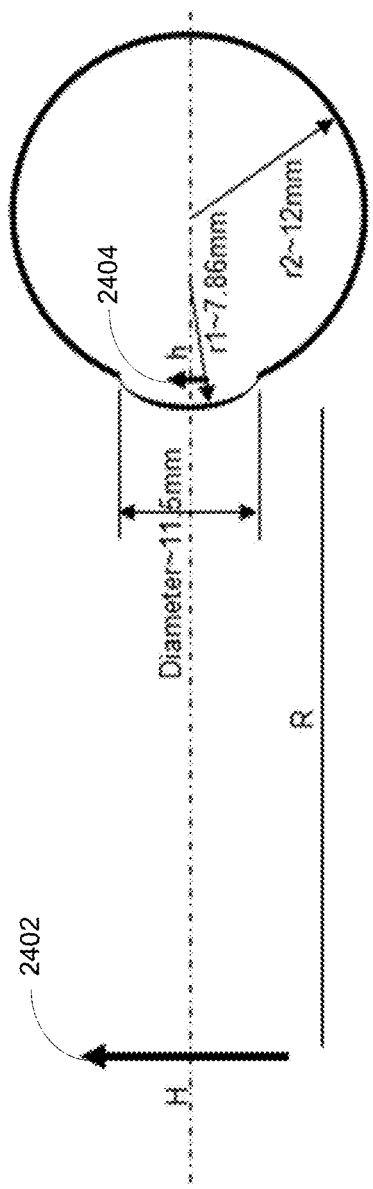
FIG. 24

331- User eye cornea
333- User eye pupil
1000- Center of the screen center
1013- image of light source 101
1033- image of light source 103
1053- image of light source 105
1073- Image of light source 107

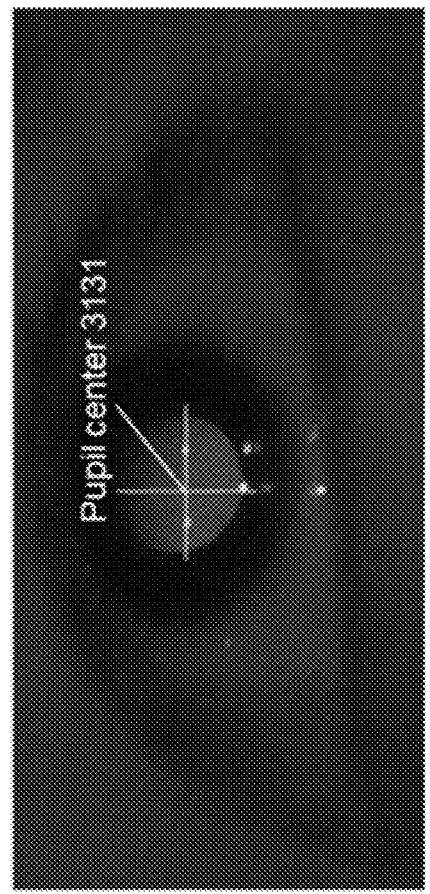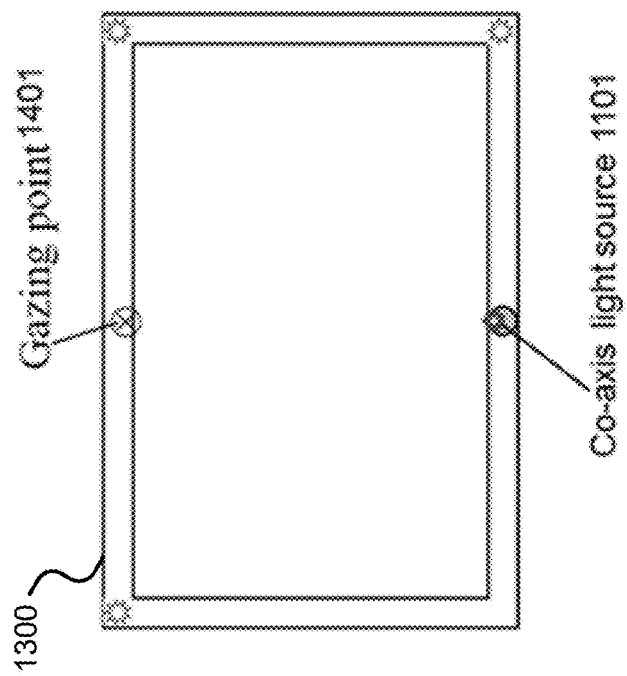
FIG. 25D
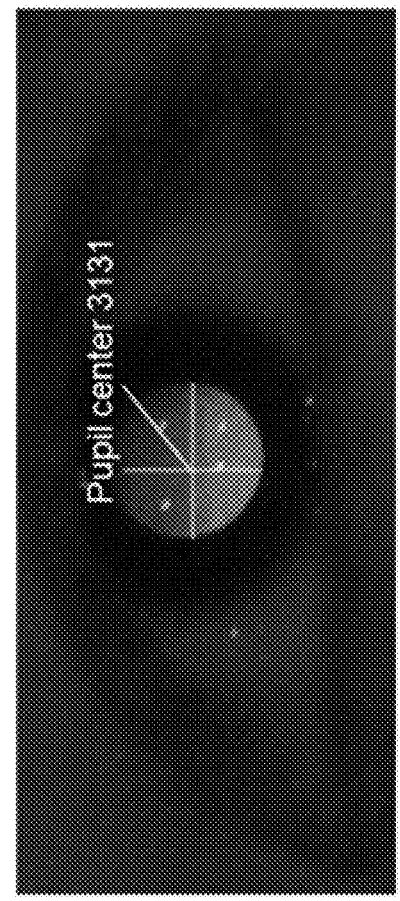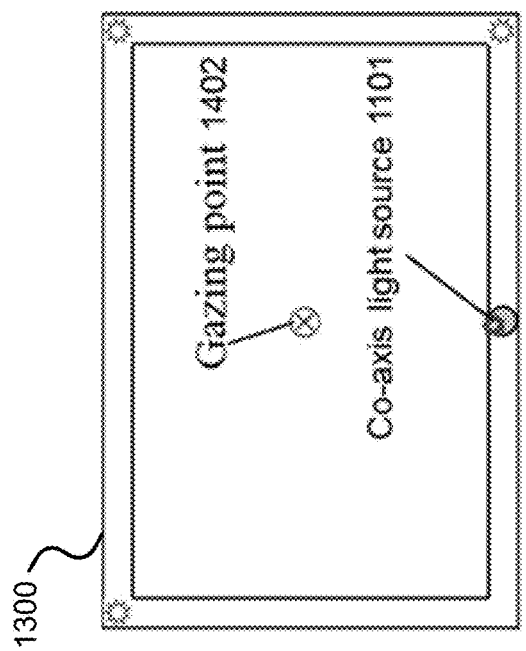
FIG. 25E

33 – User eye
44 – user head
55 – User eye retina blood vessel
66 – Light spot traces
701 – Light sources for retro-reflection
888 – Mobile device
7013 – Light beams from sources 701

OPTICAL EYE TRACKING

CROSS REFERENCE TO RELATED APPLICATIONS

This patent document claims the benefit of priority of U.S. Provisional Patent Application No. 61/902,222, filed on Nov. 9, 2013, and U.S. Provisional Patent Application No. 62/037,035, filed on Aug. 13, 2014. The entire contents of the before-mentioned patent applications are incorporated by reference as part of the disclosure of this document.

TECHNICAL FIELD

This patent document relates to eye tracking and eye reaction sensing technologies.

BACKGROUND

Electronic devices rely on various user movements as input to perform different functions and to operate in various modes or states. For examples, user gestures such as hand movements can be detected and translated into user control of a menu item or a game function. Similar to gestures, eye movements can be detected to perform scroll operation, to keep a screen turned on, or to operate a head-up-display.

SUMMARY

Techniques, systems, and devices are described for optical sensing of reflected light from an eye and tracking of eye movement for mapping the position of the eye movements to interact with a device. In some implementations, for example, the optical sensing and tracking functions are integrated into the device.

The subject matter described in this patent document can be implemented in specific ways that provide one or more of the following features. For example, the disclosed eye mapping technology can be integrated with mobile devices (e.g., smartphones and tablets) and computing devices (e.g., such as computer monitors) to track an operator's eye gaze position, movement, and blinking state. For example, the disclosed technology can use the retroreflection of light from the eye based on fixation and saccade eye movements for optical sensing and eye mapping. The disclosed eye mapping devices and methods can be used as an absolute sensor that is not sensitive to head movement nor sensitive to retina optical reflectance fluctuation.

Methods, systems, and devices are disclosed for optical sensing and tracking of eye movement to perform operations in various application. The described methods, systems and de and devices can be used to track the gaze or focus point of a user's eye or eyes relative to a display screen of a device, such as a touch sensing screen in real time. A cursor or focus indicator can be generated on the display screen based on the tracked gaze or focus point of the user's eye or eyes. The generated cursor or focus indicator can be used to select, activate, or interact with a software application, a document, a graphical user interface (GUI) or an icon or object on the GUI to cause a desired action, operation or effect. The generated cursor or focus indicator can be used in combination with one or more additional user input mechanisms such as operational buttons, switches or triggers on the device. The cursor or focus indicator control based on eye tracking described in this document can be implemented as an "eye mouse" to replace a physical mouse or pointer device to control the movement or position of the cursor on the display screen. In mobile or hand-held devices, this "eye mouse" can be used to enable a one-handed operation or control various operations and functions via the display screen.

In one aspect, a method for controlling a cursor based on a user's gaze includes presenting a display interface to the user. A first group of light sources can be used to emit a first modulated light. A photodetector module can be used to generate eye tracking signals from retroreflected lights from a user's eye corresponding to the emitted first modulated light from the first group of light sources. A second group of light sources can be used to emit a second modulated light. A visual sensor, such as a camera, can be used to capture images of the user's eye including reflection images of the emitted second modulated light from the second group of light source. The generated eye tracking signals can be used to determine eye pupil center coordinates of the user's eye, The captured images of the user's eye can be used to determine screen center coordinates of the display interface. The determined eye pupil center coordinates and the determined screen center coordinates can be used to determine a gaze point of the user's eye on the display screen. A cursor can be displayed on the display interface based on the determined gaze point.

The subject matter described in this patent document can be implemented in specific ways that provide one or more of the following features. For example, the disclosed eye tracking technology can be integrated with mobile devices (e.g., smartphones and tablets) and computing devices (e.g., such as computer monitors) to track and detect a location of gaze of an operator's eye on the mobile device, as well as the position, movement, and pupil size of the operator's eye. The disclosed technology can use the eye tracking information based on the retroreflection light to implement a cursor on the display of the mobile device and to adjust the position of the cursor based on user's point of gaze to function as an "eye mouse." The eye mouse's eye gaze detection function may be used for pay-per-gaze advertisements. The eye mouse's pupil size detection may be used to collect customer reaction data that is useful for advertisement management, games developer, and etc.

BRIEF DESCRIPTION OF THE DRAWINGS

FIG. 7A shows a diagram of an exemplary eye tracking device of the disclosed technology used for calibration.

FIG. 7B shows a diagram of an exemplary eye tracking device of the disclosed technology used for operating a user device by detecting eye movement and/or blinking to control functions of the device.

FIG. 9 shows a diagram of an exemplary eye tracking device of the disclosed technology used for detecting eye movement and/or blinking to control functions of a device.

FIG. 10 shows a diagram of an exemplary eye tracking device of the disclosed technology including a single sensor set with a light blocking barrier and used for detecting eye movement and/or blinking to control functions of a device.

FIG. 24 shows a diagram illustrating the concept of using the cornea surface as a reflection lens.

FIGS. 25D and 25E show diagrams and corresponding images from an exemplary implementation of an exemplary eye mapping device to determine the gazing point of the user's eye.

DETAILED DESCRIPTION

Figure 1:
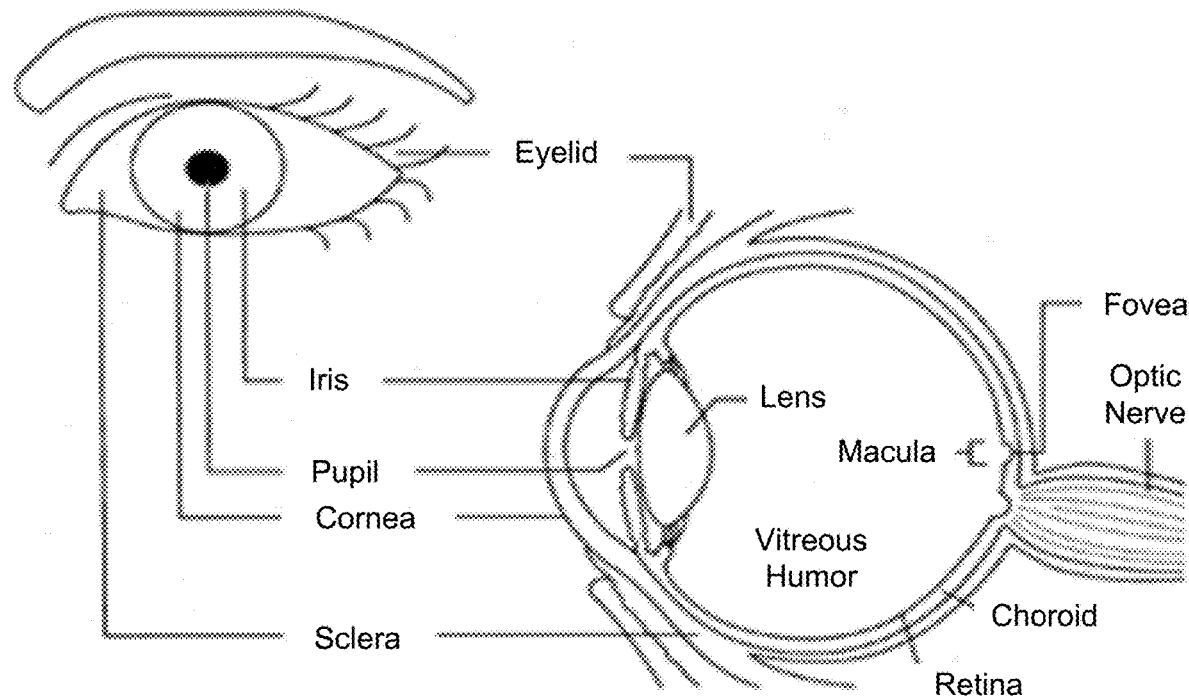
FIG. 1 shows a diagram of the anatomy of a human eye.

Examples provided below illustrate techniques for monitoring and tracking position and movement of the aiming of an eye or eyes on a display screen in real time, techniques for using the eye aiming on the display screen to place and move a cursor on the display screen, and techniques for using a physical trigger on the device to use the cursor to select, activate or interface with an object, document, software or icon on the display screen.

In one aspect, a user device having an eye-tracking feature is described. This user device includes: a front panel including a display screen; a first group of light sources positioned at a first region of the front panel; a photodetector module positioned on the front panel in the vicinity of the first group of light sources for generating eye tracking signals from retroreflected lights from a user's eye corresponding to emitted light from the first group of light sources; a second group of light sources positioned at a second region of the front panel; and a sensor camera positioned on the front panel for capturing images of a user's eye including reflection images of emitted light from the second group of light sources. The user device also includes a processor coupled to the photodetector module and the sensor camera, the processor is operable to: process the eye tracking signals to determine eye pupil center coordinates of the user's eye; process the captured images of the user's eye to determine screen center coordinates of the display screen; and compare the determined eye pupil center coordinates and the determined screen center coordinates to determine a gaze point of the user's eye on the display screen. The display screen is configured to display a cursor at the determined gaze point.

In one aspect, a technique for controlling a cursor based on a user's gaze includes the steps of: presenting a display interface to the user; using a first group of light sources to emit a first modulated light; using a photodetector module to generate eye tracking signals from retroreflected lights from a user's eye corresponding to the emitted first modulated light from the first group of light sources; using a second group of light sources to emit a second modulated light; using a sensor camera to capture images of the user's eye including reflection images of the emitted second modulated light from the second group of light source. The technique further includes: processing the eye tracking signals to determine eye pupil center coordinates of the user's eye; processing the captured images of the user's eye to determine screen center coordinates of the display interface; comparing the determined eye pupil center coordinates and the determined screen center coordinates to determine a gaze point of the user's eye on the display screen; and displaying, on the display interface, a cursor based on the determined gaze point.

In another aspect, a process for controlling a cursor based on a user's gaze, includes the steps of: presenting a display interface to the user; using a first group of light sources to emit a first modulated light and a second group of light sources to emit a second modulated light toward an eye of a user, wherein the first modulated light and the second modulated light have substantially the same modulation frequency, and wherein the modulation phases of the first modulated light and the second modulated light are substantially opposite to each other; receiving at a photodetector module, a returned light including at least a partial retroreflected light from the eye of the user based on the first and second modulated lights from the first and second groups of light sources; filtering the received light to reject background light and scattered light based on the first and second modulated lights; processing the output signal from the photodetector module to determine a location of gaze of the eye of the user on the display interface based at least on the partial retroreflected light corresponding to the first and second modulated lights; and displaying on the display interface a cursor at the determined location of gaze.

In another aspect, a portable device capable of high speed communication with another portable device is described. The portable device includes a front panel including a display screen and at least one light source positioned on the front panel outside of the display screen, wherein the at least one light source is operable to transmit data to the other portable device by emitting a light beam carrying a data signal toward the other portable device. The portable device also includes a multi-element sensor positioned on the front panel outside of the display screen, wherein the multi-element sensor is operable to receive a light beam carrying a data signal emitted by the other portable device.

FIG. 1 shows a diagram of the anatomy of a human eye. The outer wall of the eye includes three concentric layers. The outer layer includes the cornea, which is a transparent structure that covers the iris and lens that function as the focusing system of an eye, and the sclera, which is an opaque structure forming a fibrous, protective, outer layer of the eye containing collagen and elastic fiber and also referred to as the 'white of the eye'. The iris is a thin, circular structure in the eye containing pigment, e.g., determining one's 'eye color', and that controls the diameter and size of the pupil. The pupil is the adjustable opening at the center of the iris that allows varying amounts of light to enter the eye through the lens. The lens is a transparent, biconvex structure that can refract light to focus it on the retina. The retina is a layered structure in the back of the eye with several layers of neurons (the photoreceptor cells) interconnected by synapses to receive the focused light as an image and transduce the image into electro-chemical neurological signals. The photoreceptor cells of the retina include cones (e.g., ~6% of the photoreceptor cells) and rods (e.g., ~94% of the photoreceptor cells), which are located mainly along the peripheral of the retina. Cones are concentrated in the center region of the retina, known as the fovea. The macula is an oval-shaped highly pigmented yellow spot near the center of the retina and containing the fovea, parafovea, and perifovea. The fovea is a small pit that contains the largest concentration of cone cells in the eye and is responsible for central, high resolution vision. The choroid is a region of the eye rich in blood vessels that supplies the outer layers of the retina. The eye also includes fluids such as the aqueous humor located in the front region between the cornea and the iris and the vitreous humor located in the rear region behind the lens.

The vision field is generally divided in to three regions: the fovea, parafovea and peripheral vision regions. The fovea region provides the sharpest vision; the parafovea region previews foveal information; and the peripheral vision reacts to flashing objects and sudden movements. For example, peripheral vision includes approximately 15-50% of the acuity of the fovea and it is also less color-sensitive.

Figure 2:
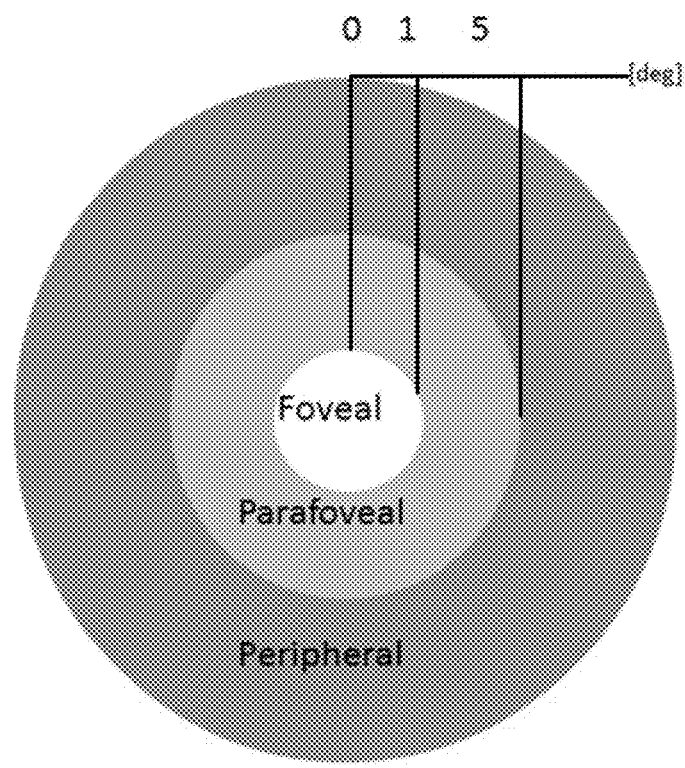
FIG. 2 shows a diagram of the vision field.

FIG. 2 shows a diagram of the vision field including the fovea, parafovea and peripheral vision regions with an exemplary degree of the visual field that the regions can see. In the human eye, the three vision field regions are asymmetric. For example, in reading, the so-called perceptual span (e.g., size of the effective vision), is 3-4 letter spaces to the left of fixation and 14-15 letter spaces to the right. Also for example, 1° of visual angle is roughly equivalent to 3-4 letter spaces.

Eyes move all the time, e.g., even during sleep. There are several different types of eye movement which can include pursuit, tremor, rotation, drift, and saccades. In humans, the eyes move around when looking at a scene, rather than a fixed steadiness, locating parts of interest of the scene to mentally create a three-dimensional map corresponding to the scene. For example, when scanning a scene or while reading words on a page, the eyes make jerky saccadic movements and stop several times, moving very quickly between each stop. A saccade is a fast movement or 'jump' of an eye, which connect fixations.

Saccades can be quick, simultaneous movements of both eyes in the same direction. Saccades occur rapidly, e.g., with durations of 40-120 ms, move quickly, e.g., up to 600°/s, and are ballistic, in which the end point of saccade cannot be changed during the movement. The saccadic movements of the human eye may be due to the role of the in resolving objects detected in vision, e.g., such that by moving the eye so that small parts of a scene can be sensed with greater resolution using the visual processing functionality of the nervous system more efficiently. A visual fixation, on the other hand, is when the eye maintains a gaze on a single location. In fixation, the eye is a relatively still and 'fixated' to the certain point, e.g., such as when reading a single word. In vision, information from the scene is mainly acquired during fixation. For example, the duration of fixation can vary from 120-1000 ms, e.g., typically 200-600 ms, and a typical fixation frequency is less than 3 Hz.

Figure 3A:
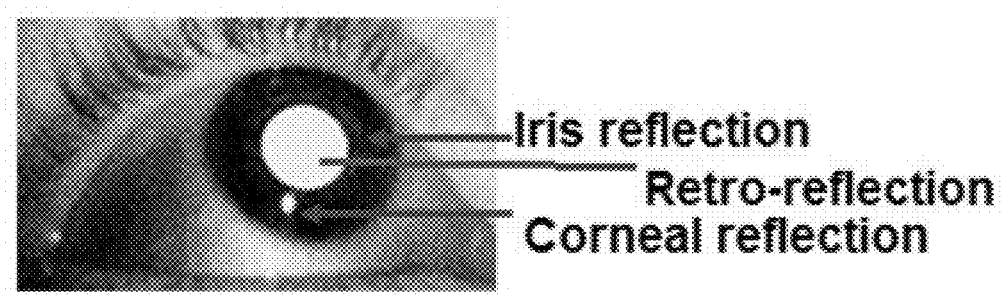
FIGS. 3A and 3B show a diagram and an image of an eye illustrating the three reflections when the eye is illuminated by light sources.
Figure 3B:
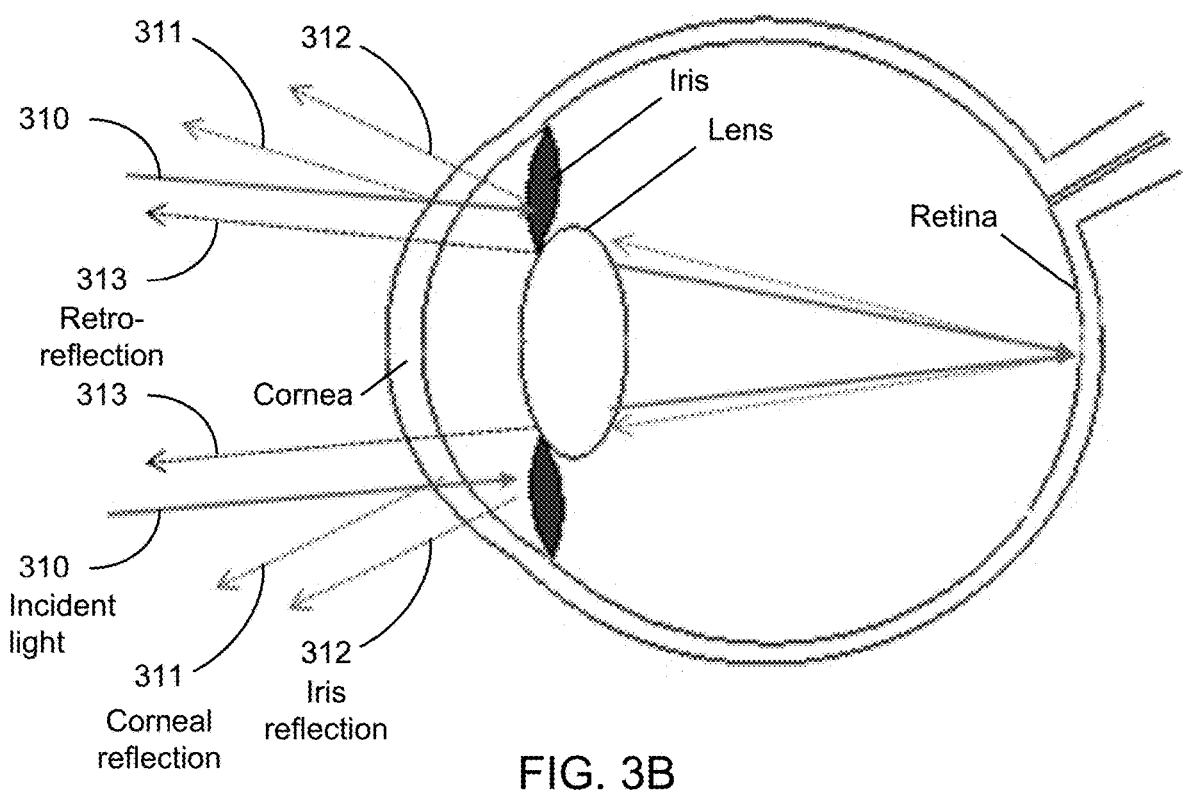

FIGS. 3A and 3B show an image and a diagram of an eye illustrating the three reflections when the eye is illuminated by light sources. The three types of eye reflections include corneal reflections of light reflected off the cornea, iris reflections of light reflected off the iris, and retroreflections of light reflected off the retina. For example, as shown in FIG. 3A, a corneal reflection forms a tiny spot; an iris reflection can look dark but colorful; and a retroreflection can be bright with strong direction dependence. The diagram of FIG. 3B shows a reflected light beam 311 reflected by corneal reflection based on an incident light beam 310 incident upon the cornea of an eye; a reflected light beam 312 reflected by iris reflection based on the incident light beam 310 having passed through the cornea of the eye and incident upon the iris; and a reflected light beam 313 reflected by retroreflection based on the incident light beam 310 having passed through the cornea and lens of the eye and incident upon the retina.

Eye tracking is the process of measuring a point of gaze (where one is looking) or motion of an eye relative to the head. Eye tracker devices and systems measure eye positions and eye movement. Eye tracking has been used clinically and in research on the visual system in medical and cognitive studies, as well as in psychology, in cognitive linguistics and in product design.

One example of an existing eye tracking modality includes video-based eye tracking techniques, e.g. referred to as the single point method. Such techniques in the single point method include tracking one visible feature of the eyeball, e.g., such as the limbus (the boundary of sclera and iris), and/or the pupil. For example, a video camera can observe one of the user's eyes. Image processing software analyzes the video image and traces the tracked feature. Based on calibration, the system determines where the user is currently looking. In such systems, head movements are not allowed, and a bite bar or head rest is typically required. In an alternative but related example of a video-based eye tracking technique, substantially the same idea is implemented as in the previously described example of the single point method, except that two features of eye are tracked, e.g., corneal reflection and the pupil. Such methods use IR light (invisible to human eye) to produce corneal reflection and to cause a bright or dark pupil, which helps the system to recognize pupil from video image.

Each of these exemplary existing methods suffer from significant limitations and deficiencies. For example, both need extra device(s) either mounted on floor or head. Also, such methods require eye tracking systems or devices that cannot be merged into mobile devices like smartphones or tablets. Additionally, these existing methods provide very limited information that can be withdrawn, e.g., no matter using bright pupil measuring or dark pupil measuring, and the associated software can be quite complicated and unreliable.

Techniques, systems, and devices are disclosed for optical sensing and tracking of eye movement using a user interface to interact with a device. In some implementations, for example, the optical sensing and tracking functions are integrated into the device.

The disclosed eye tracking technology can be integrated with mobile devices (e.g., smartphones and tablets) and computing devices (e.g., such as computer monitors) to track an operator's eye position, movement, and blinking state. The disclosed technology can use the retroreflection of light from the eye based on fixation and saccade eye movements for optical sensing and eye tracking In one aspect, a method for tracking the movement of an eye includes emitting light toward an eye of a user using multiple (e.g., three) light sources equally spaced from a photodetector module (e.g., a camera) of a device, receiving at the photodetector module at least a partial retroreflection of the light emitted by each of the multiple light sources retroreflected from the eye, and determining a positional parameter of the eye based on differential values of the at least partial retroreflections corresponding to the multiple light sources. For example, the device can include, but is not limited to, a smartphone, a tablet, a picture or video camera, a computer monitor, or a laptop computer. In some implementations, for example, the method can be implemented while the head of the user is in motion, e.g., relative to the device. In some implementations of the method, for example, the multiple (e.g., three) light sources can emit colored light of different colors, e.g., in which the colored light can include red light, green light, blue light, and yellow light, or any combination thereof, different wavelengths, and/or different modulations of frequency. In some implementations of the method, for example, the emitted light can include infrared light. Also, for example, the emitted light can include flashing light at a frequency correlated with a frame rate of the photodetector module (e.g., camera). In some implementations, for example, the method further includes using the at least partial retroreflections received at the exemplary camera, detecting blinking movements of the eye. Additionally, the method can further include processing the detected blinking movements as data, and in some implementation, the method can also use the data as input data for at least one function of the device.

Figure 4A:
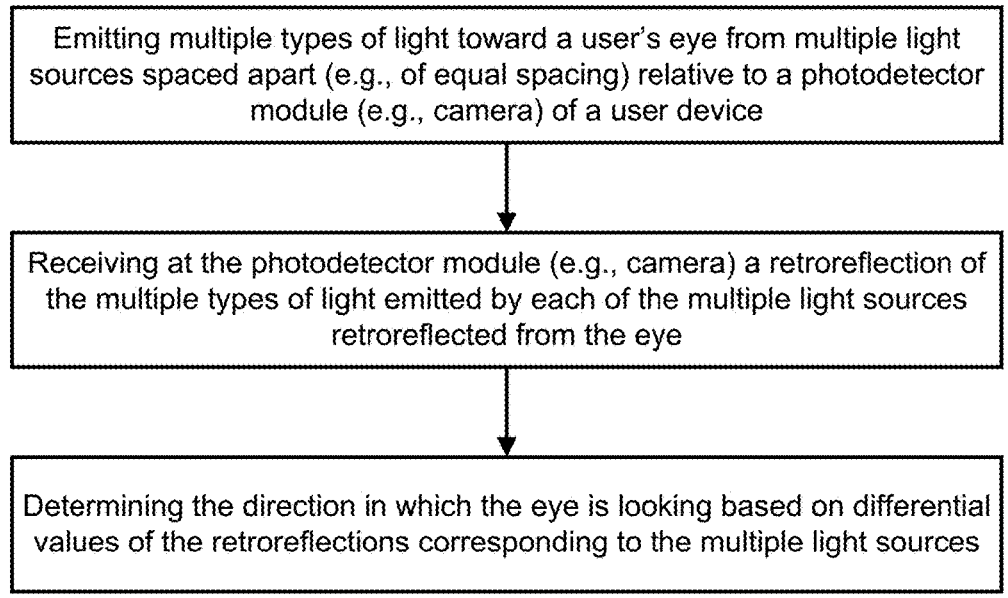
FIG. 4A shows a process diagram depicting the steps of the exemplary method of the disclosed technology for tracking the movement of an eye.

FIG. 4A shows a process diagram depicting an exemplary method of the disclosed technology for tracking the movement of an eye. The method includes a process to emit multiple (e.g., three) types of light from multiple respective light sources toward the eye of the user, in which the three light sources are equally spaced relative to a photodetector module (e.g., a camera) of a user's device. For example, the process can be implemented using one camera, in which the three light sources are offset from the camera with equal distance.

Figure 4B:
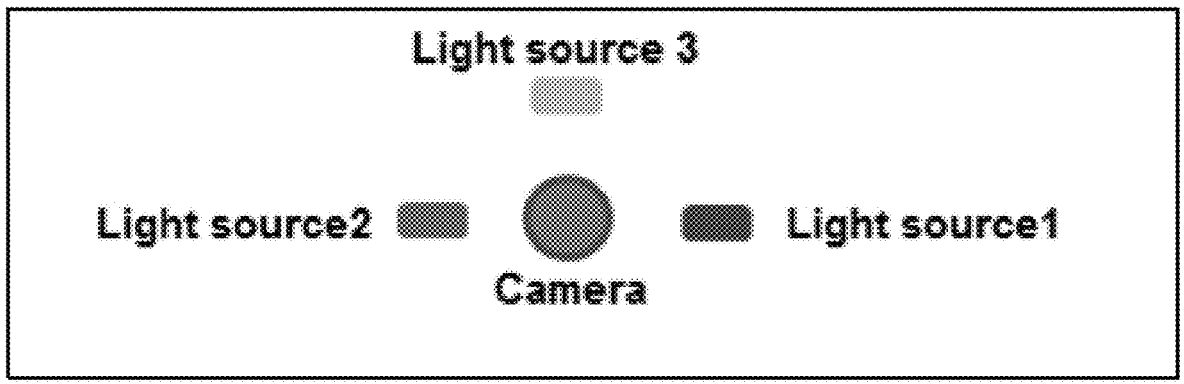
FIG. 4B shows a illustrative diagram of an exemplary interface of a user device to implement the exemplary eye tracking method.

The method includes a process to receive at least a partial retroreflection of the three types of light emitted by each of the three light sources that is retroreflected from the eye using the exemplary camera. For example, the distance is configured such that the camera can receive at least partial of the retro-reflections from all light sources. For example, the three light sources can emit colored light of the same or differing colors, or in other examples, infrared light to avoid stimulating the user. In some examples, the light sources can be color light-emitting diodes (LEDs), as exemplified in FIG. 4B, which shows an illustrative diagram of an exemplary interface of the user's device to implement the exemplary eye tracking method. The exemplary LEDs can be selected to emit particular RGB color, e.g., to match a color filter on the camera sensor. The exemplary LEDs can be infrared LEDs. The exemplary color or infrared LEDs can be turned on in a sequence that is synchronized with the camera video frames. Also, for example, the three light sources can emit flashing light in time domain, but it is noted that flashing light may reduce the data rate.

Referring back to FIG. 4A, the method includes a process to determine a positional parameter of the eye, e.g., such as the direction in which the eye is looking or the location of the eye in space. For example, by calculating the differential values of the three retroreflections (e.g., at least partial retroreflections corresponding to the three light sources), the direction and other parameters of eye movement can be determined.

In some examples, the process to determine the direction, location, and/or other positional parameters of the eye and eye movement can include the following.

The disclosed method is not sensitive to eye distance and head movement, e.g., providing a reliable eye tracking solution. This eye tracker also can easily detect operator eye blinking reliably, in which the blinking information can be processed as data and used as input for the device. For example, smartphone operation tends to be at a distance of 1 to 2 feet. The disclosed method can function with head-free accuracy at a variety of distances and angles, e.g., including 0.1°-0.25°, and include head-free resolution of 0.02° rms.

The disclosed method can be implemented track the movement of both eyes of the user sequentially or concurrently.

Figure 5A:
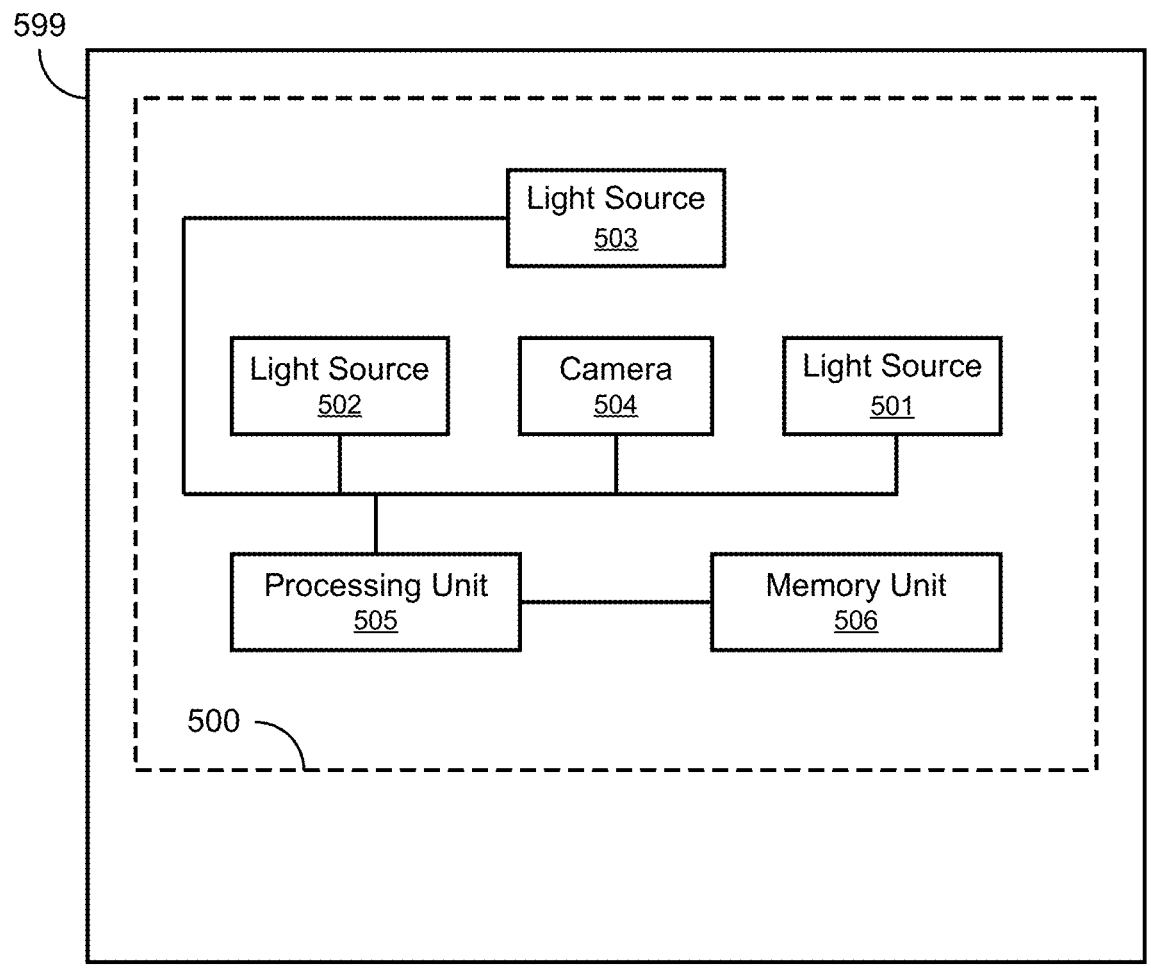
FIG. 5A shows a block diagram of an exemplary eye tracking unit of the disclosed technology implemented in a user device.

FIG. 5A shows a block diagram of an eye tracking unit 500 implemented in a user's device 599, e.g., which can be, but is not limited to, a smartphone, a tablet, a picture or video camera, a computer monitor, or a laptop computer. The eye tracking unit 500 includes three light sources 501, 502, and 503 equally spaced from each other relative to a camera 504 of the device 599. The eye tracking unit 500 includes a processing unit 505 coupled to a memory unit 506. The memory unit 506 can, for example, include processor-executable code, which when executed by the processing unit 505, configures the eye tracking unit 500 to perform various operations, such as receiving information, commands, and/or data, e.g., from the camera 504, processing information and data, and transmitting or providing information/data or commands to another entity, e.g., such as the light sources 501, 502, and 503 and/or the camera 504, or to the user device 599. In some implementations, for example, the memory unit 506 can be configured as a disk or solid-state device (SSD) storage unit.

In some implementations of the eye tracking unit 500, the eye tracking unit 500 can utilize the processing unit(s) and/or memory unit(s) of the user device 599.

Figure 5B:
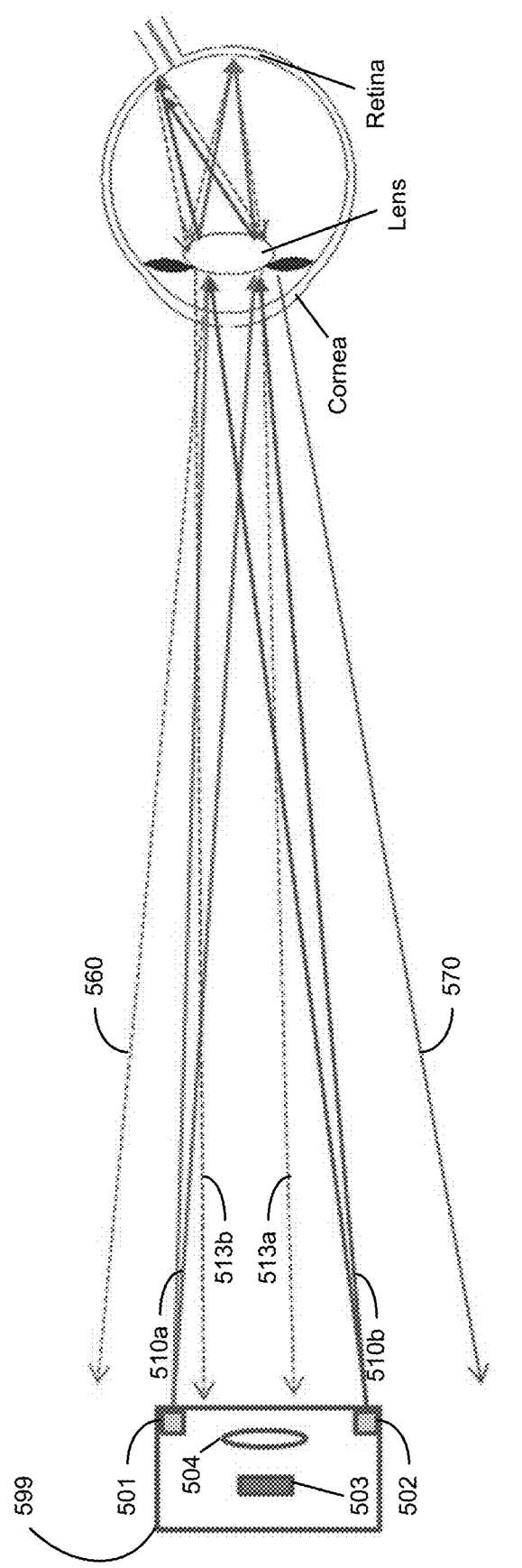
FIG. 5B shows a diagram of operation of the exemplary method described in FIG. 4A using retro-reflection of the eye and multiple light sources and one camera of an exemplary mobile device.

FIG. 5B shows a diagram of operation of the exemplary method described in FIG. 4A using retro-reflection of the eye and multiple light sources and one camera of the user device 599, e.g., such as a smartphone. The diagram of FIG. 5B shows reflected light beams 513a and 513b reflected by retroreflection based on incident light beams 510a and 510b produced by the light sources 501 and 502, respectively. The light path of the incident light beams 510a and 510b includes passing through the cornea and lens of the eye and becoming incident upon the retina. The light incident upon the retina can be retroreflected by the retina such that the light path of the retroreflected light passes again through the lens and cornea and directed towards its source, as shown by the retroreflected light beams 513a and 513b. The retroreflected light beams 513a and 513b can be captured by the camera 504. For example, some of the retroreflected light can be directed away from the user's device 599, as illustrated as retroreflected light 560 in the exemplary diagram of FIG. 5B. Also for example, some of the emitted light can be reflected from the iris, as represented in the diagram as iris reflections 570.

Figure 6A:
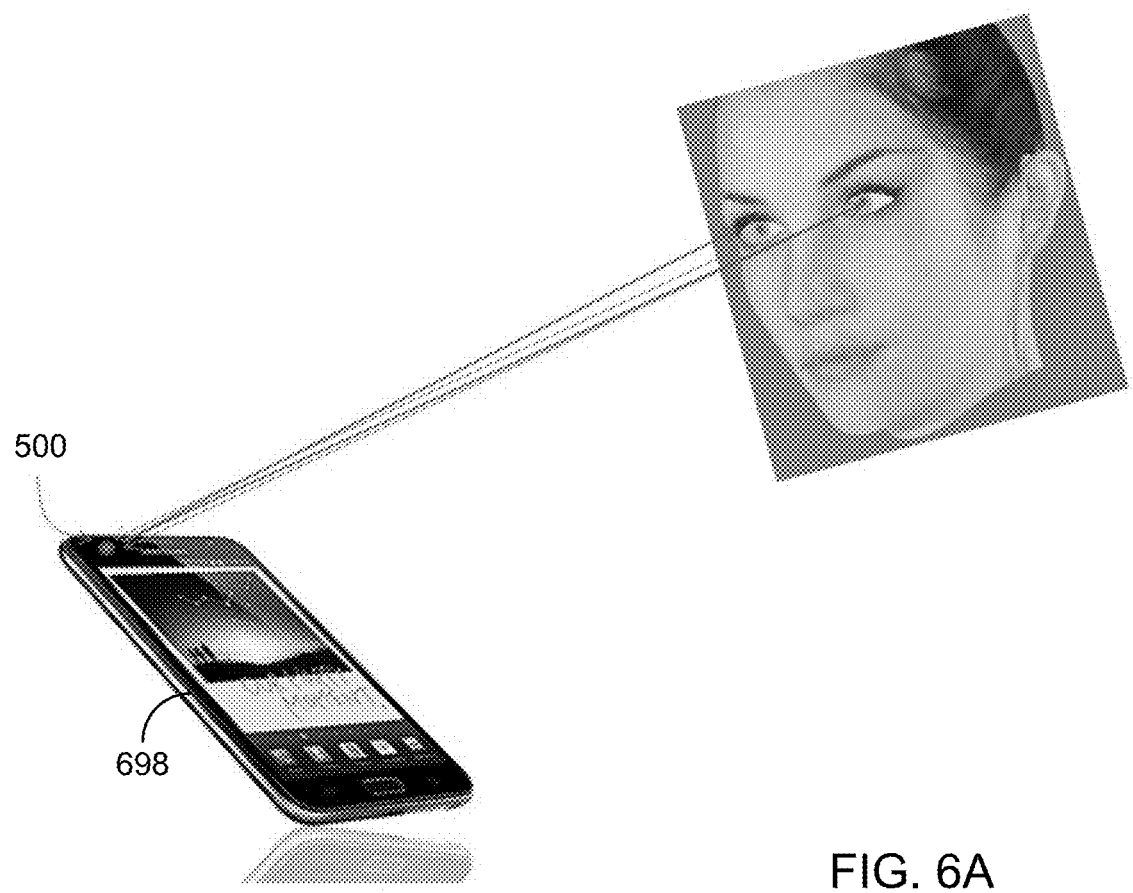
FIG. 6A shows a diagram of an exemplary eye tracking device of the disclosed technology implemented on a mobile smartphone device.

FIG. 6A shows a diagram of the eye tracking device 500 implemented on a mobile smartphone device 698.

Figure 6B:
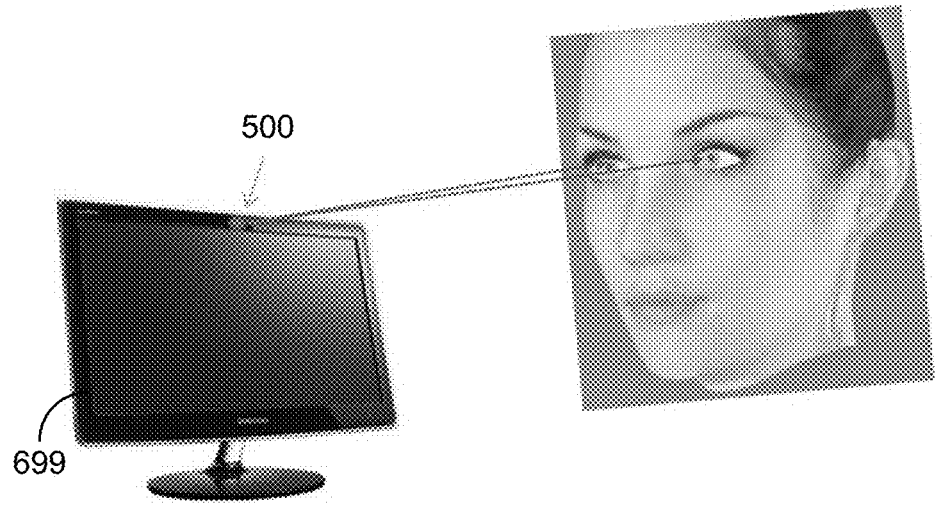
FIG. 6B shows a diagram of an exemplary eye tracking device of the disclosed technology implemented on a computer monitor or a television device.

FIG. 6B shows a diagram of the eye tracking device 500 implemented on a computer monitor or a television device 699.

In other examples, the disclosed eye tracking technology can be implemented on a head mount display (HUD) device, e.g., such as Google glass.

In some implementations, for example, the eye tracking unit 500 includes a display screen 515 configured on the same side of the exterior of the user device 599 that the light sources 501, 502 and 503 and the camera 504 are located. The display screen 515 can be communicatively coupled to the processing unit 505 and/or the memory unit 506. For example, the display screen 515 can be a display screen inherent to the user device 599.

FIG. 7A shows a diagram of an exemplary configuration of the display screen 515 of the eye tracking unit 500 that can be used for calibration of the eye tracking unit 500. For example, a fixed location marker 516 is displayed, in which a calibration operation includes user focus watching one highlighted marker at a time and pushing a select button of the user device 599. The fixed location marker 516 can be moved to several locations on the display screen 515, exemplified in the four corners and center of the screen, in which the active marker is indicated in red. For example, the fixed location marker 516 can be shown several times and in the several locations to be displayed to carry out the calibration operation.

FIG. 7B shows a diagram of the eye tracking unit 500 including the display screen 515 and operated in any of a variety of applications in which eye movement is used as input data for the user device 599 in which the eye tracking unit 500 is implemented. For example, the eye tracking unit 500 can detect positional parameters of the user's eyes in user-performed operations, including, but not limited to, ocularly select buttons, icons or text 517 on the display screen 515 to implementing a program of the user device 599, e.g., such as a smartphone or tablet, among others. Additionally, for example, the disclosed eye tracking technology can use eye blinking, detected by the eye tracking unit 500, and utilize the blinking data, just like the eye movement data, to activate application functions of the user device 599.

Figure 8:
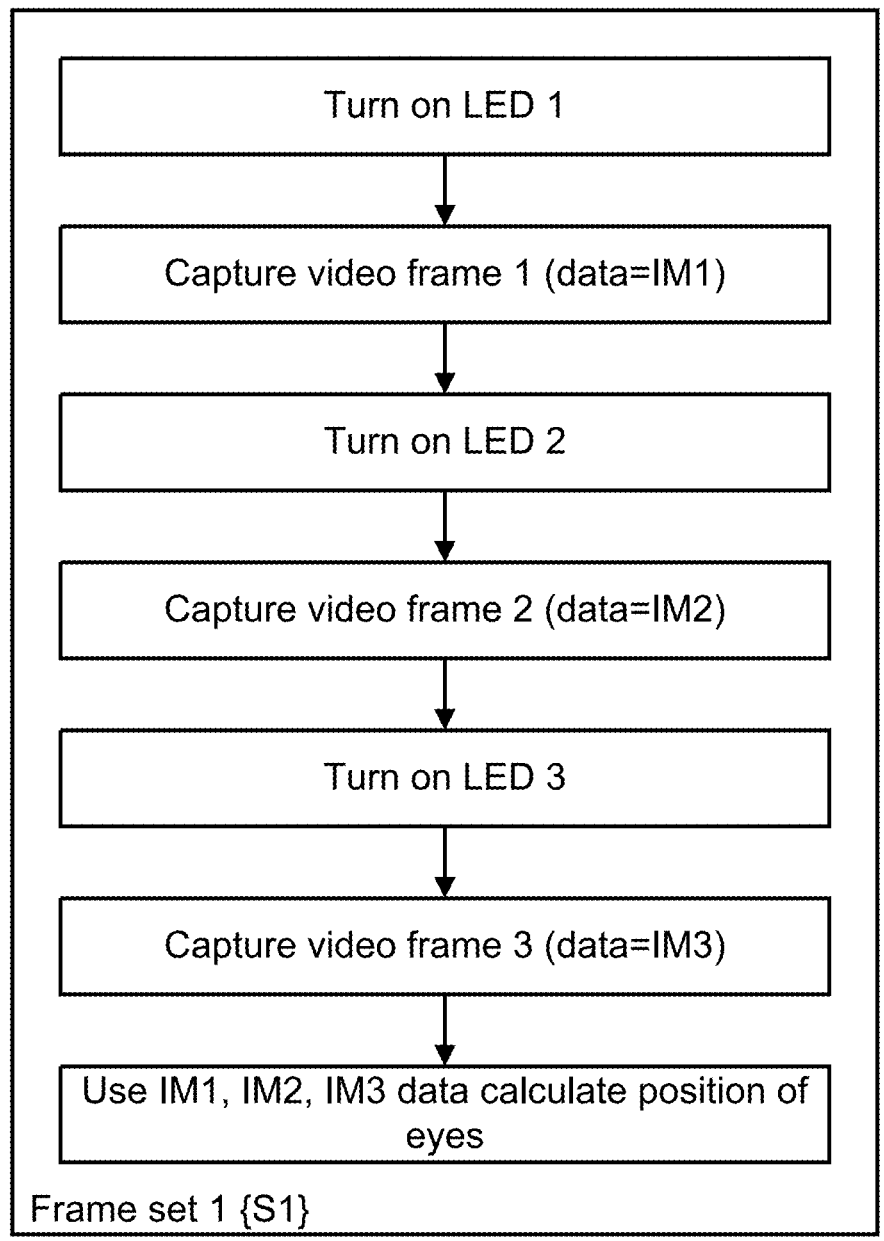
FIG. 8 shows a process diagram of an exemplary method to track the movement of an eye using a sequential light emission and capture using an exemplary tracking unit of the disclosed technology.

FIG. 8 shows a process diagram of an exemplary method to track the movement of an eye using a sequential light emission and capture using the tracking unit 500. The method includes emitting a first light from the light source 501, e.g., such as an LED 1, and capturing, using the camera 504, an image of the retroreflection of the first emitted light retroreflected by the eye in a first video frame. The method includes emitting a second light from the light source 502, e.g., such as an LED 2, and capturing, using the camera 504, an image of the retroreflection of the second emitted light retroreflected by the eye in a second video frame. The method includes emitting a third light from the light source 503, e.g., such as an LED 2, and capturing, using the camera

504, an image of the retroreflection of the third emitted light retroreflected by the eye in a third video frame. The first, second, and third video frames can be included in a frame set (e.g., frame set data 1 or $\{S_1\}$). The method includes using the first, second, and third video frame data of $\{S_1\}$ to calculate the position of the eye corresponding to an instance of time to emit the three lights and capture the three video frames. The method includes repeating this process (e.g., n times) to generate multiple, sequential frame sets $\{S\}_n$.

The method can also include detecting the blinking of the eye and using a detected blink as data for the device hosting the tracking unit 500. For example, when an eye of the user has blinked, the retroflected light is disappeared, which would be detected over multiple frame data set, and it is a feature used to detect eye blinking. For example, multiple frame set data $\{S_n\}$ can be processed to determine the occurrence of an eye blinking event, the frequency of eye blinking events, the speed of the eye blinking, the duration of the eye blinking (e.g., how long the eye is shut), and which eye blinked (e.g., left or right eye blinked or both eyes blinked). These can all be used as input data to affect a function of the device (e.g., the machine state of a smartphone or computer).

FIG. 9 shows a diagram of an exemplary eye tracking device of the disclosed technology including a single sensor set with a prism and used for detecting eye movement and/or blinking to control functions of a device. In some implementations, the exemplary eye tracking device can operate as a high resolution 'eye mouse'. In this example, the exemplary eye tracking device can include a polarized beam splitter 1 optically coupled to a micro lens 3, in which the micro lens 3 is positioned between the polarized beam splitter 1 and a band pass filter 35 to optically filter the light that enters a photodetector module 33. The exemplary eye tracking device can include a light source (e.g., near infrared LED 11), which can be modulated at a particular frequency or frequencies, in which the light source 11 is optically coupled to the linear polarizer 13 that is optically coupled to the polarized beam splitter 1 to transmit a probe light (e.g., LED irradiated light beam 15) from the device that can be retroreflected by the eyes of the user. The photodetector module 33 can be structured to include a photodetector sensitive array 25 to detect the inputted light into the module 33, which can include retroreflected light by a user's eye, e.g., which is filtered by the band pass filter 35. For example, as shown in FIG. 9, the photodetector sensitive array 25 detects light at an image spot 29 corresponding to the retroreflected light beam 21 of the right eye 18 of the user and at an image spot 27 corresponding to the retroreflected light beam 23 of the left eye 19 of the user. The exemplary eye tracking device can include a processing unit communicatively coupled to the photodetector module 33 to process the photodetected signals on the photodetector sensitive array 25 as data. The processing unit can include a general purpose processor coupled to a memory unit to store the raw and processed data. The processing unit can be configured to execute methods to track the eye movements based on the detected retroreflected light signal data and control functions of the user device, e.g., including altering the display of the user device. In some implementations of the exemplary eye tracking device, a processing unit including a processor and memory unit of the user device is used to implement the data processing methods of the disclosed technology.

FIG. 10 shows a diagram of an exemplary eye tracking (eye mouse) device of the disclosed technology including a single sensor set with a light blocking barrier and used for detecting eye movement and/or blinking to control functions of a device. In this example, the exemplary eye tracking device can include a light source (e.g., near infrared LED 11), which can be modulated at a particular frequency or frequencies, in which the light source 11 is optically coupled to the linear polarizer 13 to transmit a probe light (e.g., LED irradiated light beam 15) from the device that can be retroreflected by the eyes of the user. The exemplary eye tracking device can include a linear (receiving) polarizer 41 optically coupled to a micro lens 3 and configured near but separated from the light source 11 and linear (transmitting) polarizer 13 by a light blocker wall or barrier 45. The exemplary light tracking device a band pass filter 35 configured behind the micro lens 3 to optically filter the light that enters a photodetector module 33. The photodetector module 33 can be structured to include a photodetector sensitive array 25 to detect the inputted light into the module 33, which can include retroreflected light by a user's eye, e.g., which is filtered by the band pass filter 35. For example, as shown in FIG. 9, the photodetector sensitive array 25 detects light at an image spot 29 corresponding to the retroreflected light beam 21 of the right eye 18 of the user and at an image spot 27 corresponding to the retroreflected light beam 23 of the left eye 19 of the user. The exemplary eye tracking device can include a processing unit communicatively coupled to the photodetector module 33 to process the photodetected signals on the photodetector sensitive array 25 as data. The processing unit can include a general purpose processor coupled to a memory unit to store the raw and processed data. The processing unit can be configured to execute methods to track the eye movements based on the detected retroreflected light signal data and control functions of the user device, e.g., including altering the display of the user device. In some implementations of the exemplary eye tracking device, a processing unit including a processor and memory unit of the user device is used to implement the data processing methods of the disclosed technology.

Figure 11A:
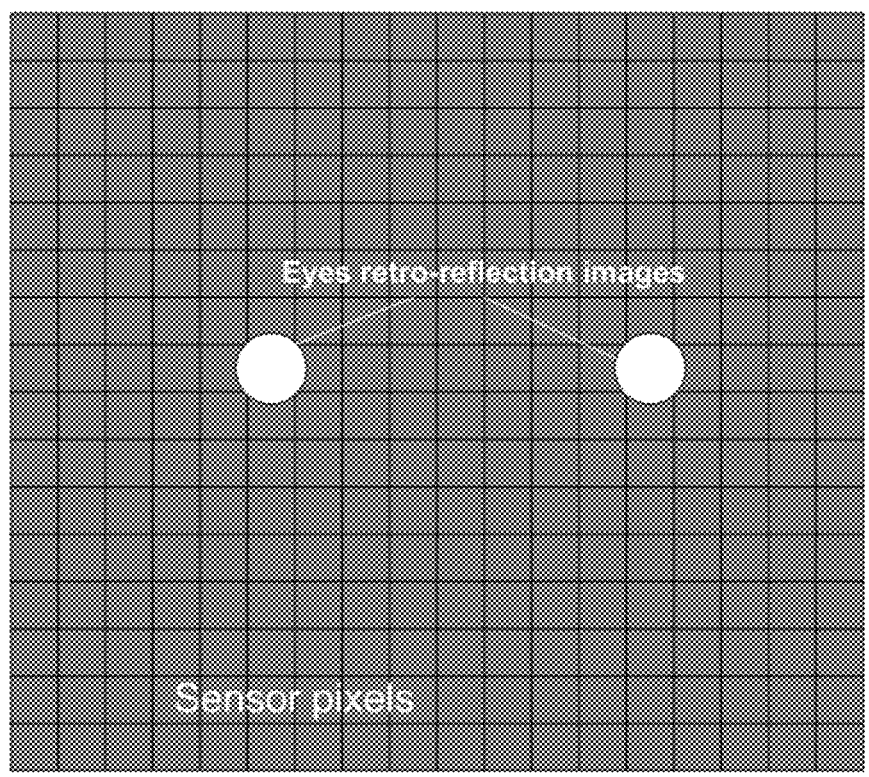
FIG. 11A shows a diagram depicting exemplary retro-reflection images on the exemplary sensor surface of an exemplary eye mouse device detected from retroreflected light by the eyes of a user of the exemplary device.
Figure 11B:
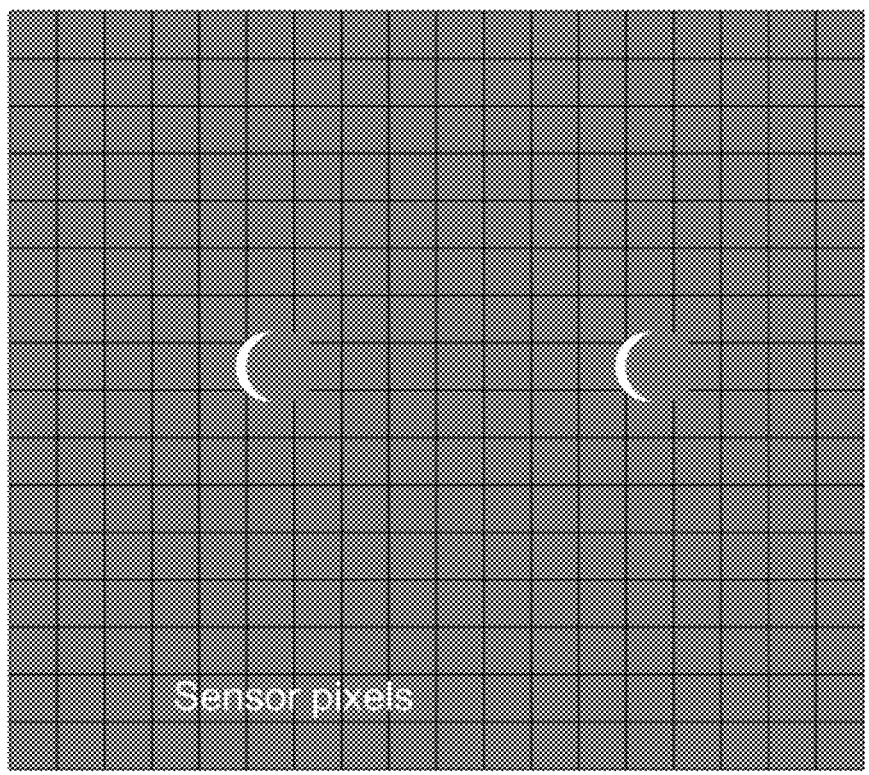
FIG. 11B shows a diagram depicting the exemplary retro-reflection images on the exemplary sensor surface when the user's eyes move.

FIG. 11A shows a diagram depicting exemplary retro-reflection images on the exemplary sensor surface (e.g., photodetector sensitive array 25) of an exemplary eye mouse device, such as those shown in FIGS. 9 and 10, in which the images are detected from retroreflected light by the eyes of a user of the exemplary device. FIG. 11B shows a diagram depicting the exemplary retro-reflection images on the exemplary sensor surface when the user's eyes move, such that the image differential can generate tracking signals using a processing unit of the exemplary device.

Figure 12:
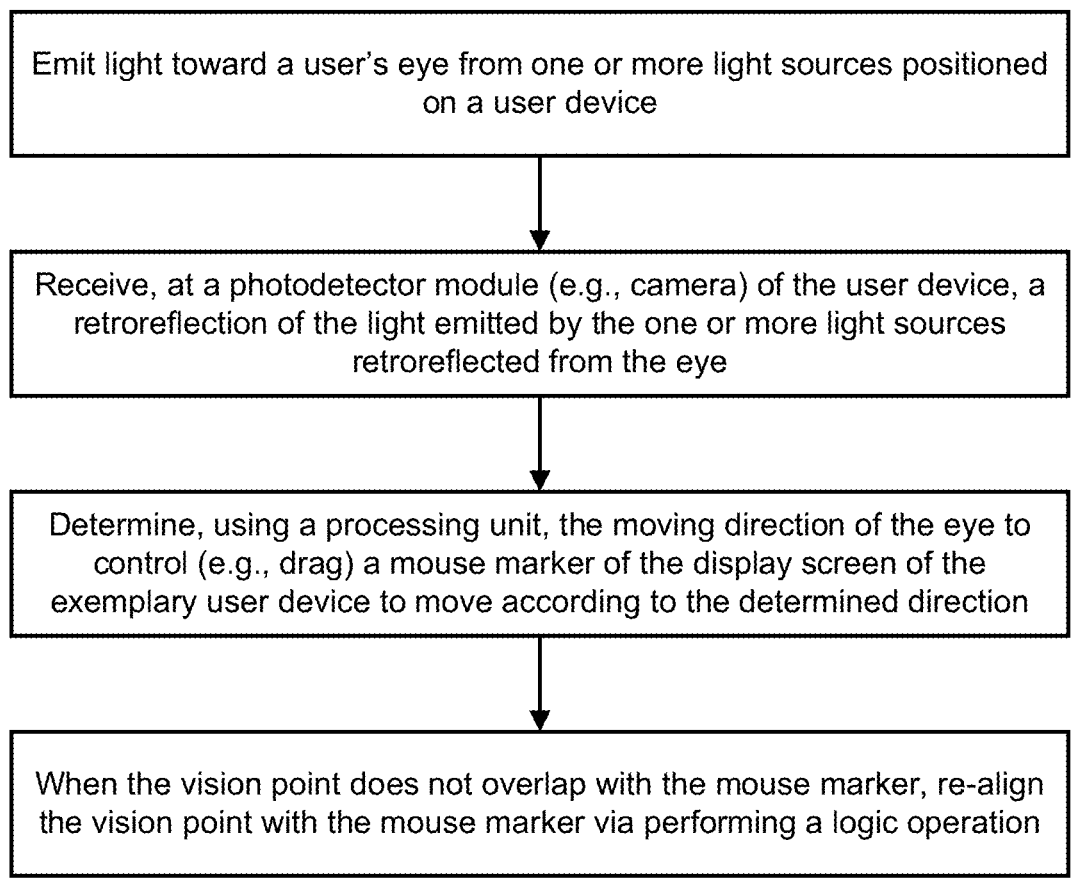
FIG. 12 shows a process diagram of an exemplary method for tracking the movement of an eye and controlling a mouse marker on a display screen using the tracked eye movements.

FIG. 12 shows a process diagram of an exemplary method for tracking the movement of an eye and controlling a mouse marker on a display screen using the tracked eye movements. The exemplary method can include a process to emit light toward a user's eye from one or more light sources configured in a user's device including an eye tracking device of the disclosed technology. For example, the user's device can include, but is not limited to, a smartphone, a tablet, a picture or video camera, a computer monitor, or a laptop computer. The method can include a process to receive, at a photodetector module of the eye tracking device of the disclosed technology in the user's device, a retroreflection of the light emitted by the one or more light sources, where the retroreflected light was retroreflected by an eye (e.g., the left eye, the right eye, and/or both eyes) of the user. The method can include a process to determine, using a processing unit of the eye tracking device of the disclosed technology or a processing unit existing on the user device, a position and/or direction of movement if the eye(s) based on the received/detected retroreflected light. In some implementations, the process to determine the position and/or movement direction of the eye can include controlling functions of the user device, e.g., including dragging a marker (e.g., mouse marker) on a display screen of the user device or altering the display screen according to the determined position and/or direction of movement. For example, when the vision point does not overlap with the mouse marker, the method can include re-aligning the vision point with the mouse marker via performing a logic operation.

Figure 13:
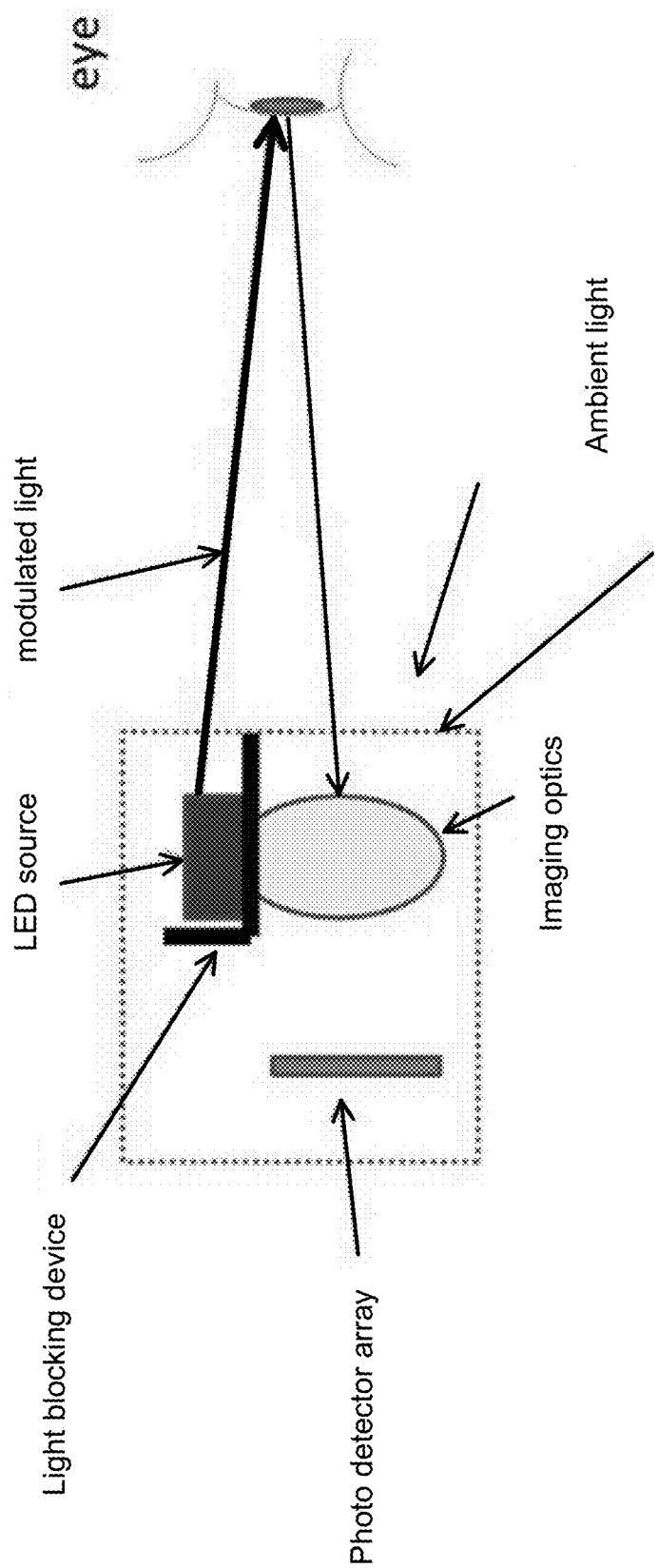
FIG. 13 shows a diagram of an exemplary eye tracking sensor device of the disclosed technology with modulated illumination light emitter and detection modules.

FIG. 13 shows a diagram of an exemplary eye tracking sensor of the disclosed technology with modulated illumination light and detection units. The exemplary eye tracking sensor device can include a light source unit (e.g., LED light source) to emit modulated light toward a user. The exemplary eye tracking sensor device can include one or more light blocking walls or barriers configured proximate the light source to block light from the light source from shining/illuminating on an image sensor of the exemplary eye tracking sensor device. The exemplary eye tracking sensor device can include imaging optics (e.g., one or more micro lens(es)) to receive and input light into the device, in which imaging optics can be configured proximate the light blocking wall (that prevents the emitted light from the light source unit from directly entering the imaging optics). The exemplary eye tracking sensor device can include a photodetector array to detect light transmitted through the imaging optics. In implementations of the exemplary eye tracking sensor device, the light source is configured to emit modulated light (e.g., at one or more frequencies) that can be retroreflected from the eye and be received by the photodetector array via the imaging optics of the exemplary eye tracking sensor device. For example, the photodetector array can be configured to include pixels and a demodulation circuit to discern between light of the modulated frequency or frequencies emitted by the light source from other light without such modulation (e.g., such as ambient light in the surrounding environment). In some implementations, the exemplary eye tracking sensor device can be communicatively coupled with a processing unit of a user device.

Figure 14:
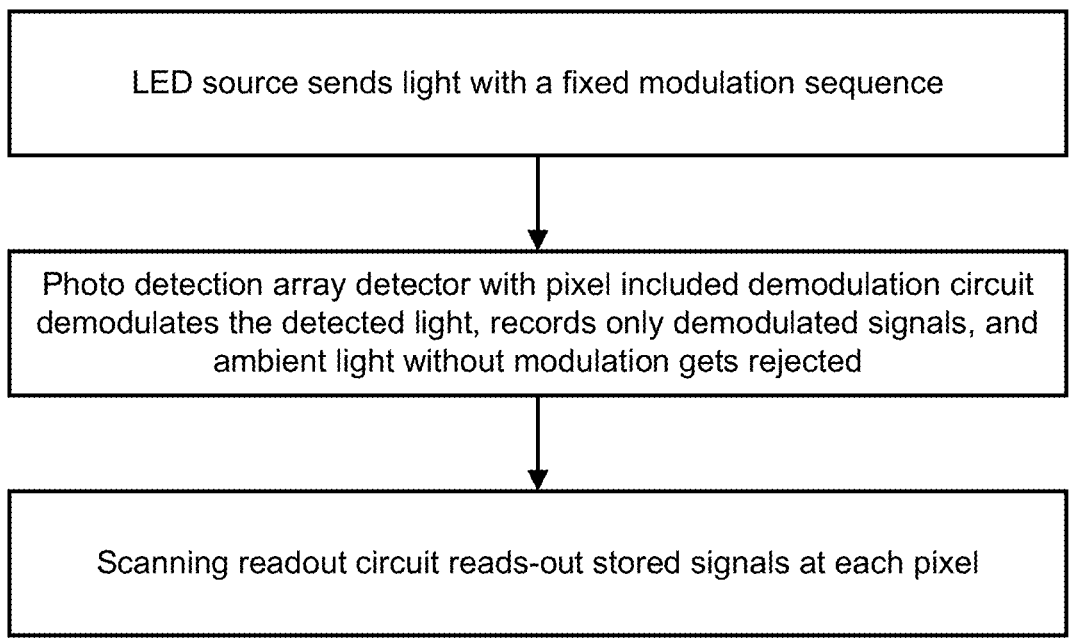
FIG. 14 shows a process diagram of an exemplary method for detecting modulated eye tracking sensor signals.

FIG. 14 shows a process diagram of an exemplary method for detecting modulated eye tracking sensor signals. The exemplary method can include a process to emit light (e.g., LED light) with a fixed modulation from a light emitting unit of an eye tracking sensor device of the disclosed technology, e.g., such as that in FIG. 13. The exemplary method can include a process to detect the modulated light at a photodetector array including a pixel included demodulation circuit. The method can include a process to demodulate the detected modulated light, in which only demodulated signals are recorded and stored (e.g., in a memory, which can be configured in the demodulation circuit), and light not of the modulated frequency (or frequencies) are rejected. The method can include a process to read out the stored signals for each pixel, e.g., using a scanning readout circuit coupled to or included in the demodulation circuit.

Figure 15:
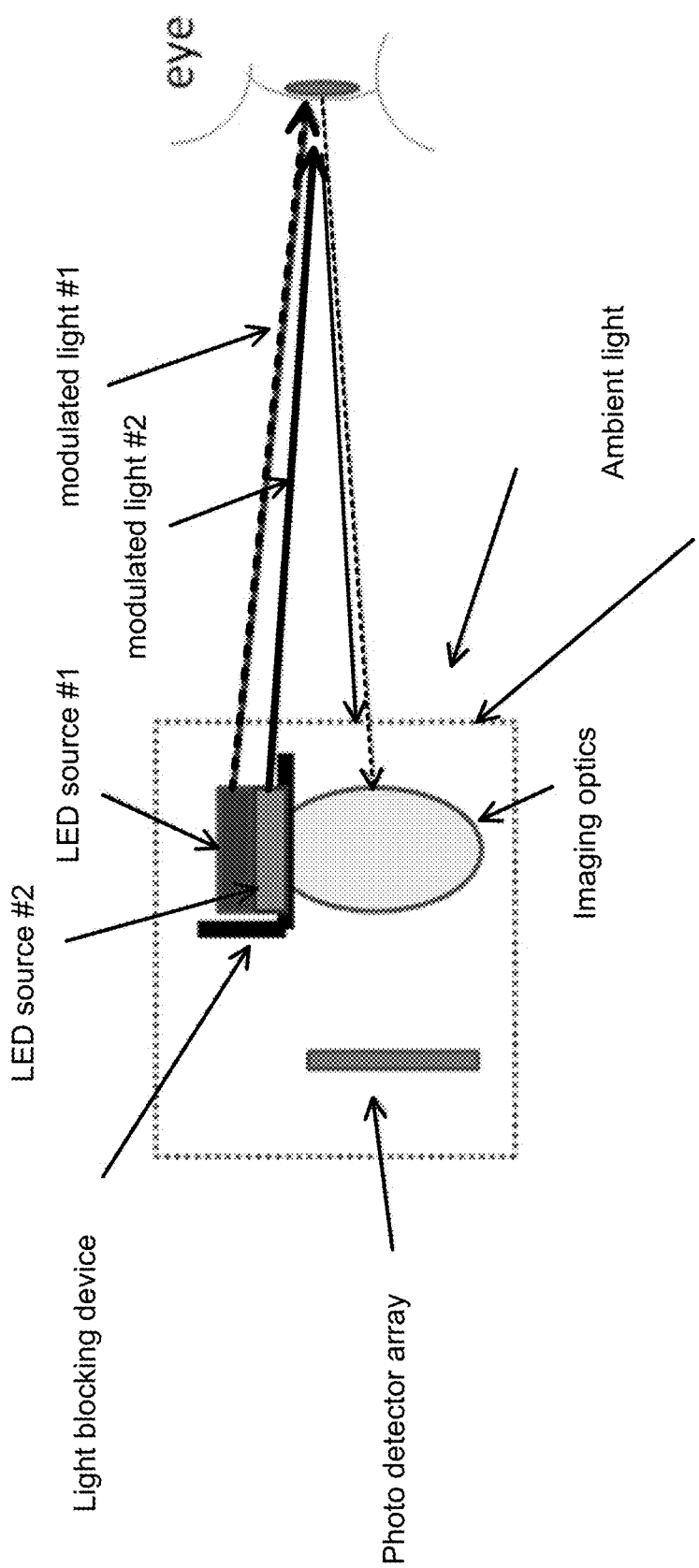
FIG. 15 shows a diagram of another exemplary eye tracking sensor device of the disclosed technology with multiple modulated illumination light emitter and detection modules.

FIG. 15 shows a diagram of another exemplary eye tracking sensor of the disclosed technology with modulated illumination light and detection units. The exemplary eye tracking sensor device of FIG. 15 can include a multiple light source unit (e.g., LED light source #1 and LED source #2) to emit multiple modulated light (e.g., modulated light #1 and modulated light #2) toward a user. The exemplary eye tracking sensor device can include one or more light blocking walls or barriers configured proximate the light source to block light from the light source from shining/illuminating on an image sensor of the exemplary eye tracking sensor device. The exemplary eye tracking sensor device can include imaging optics (e.g., one or more micro lens(es)) to receive and input light into the device, in which imaging optics can be configured proximate the light blocking wall to prevent the emitted light from the multiple light source unit from directly entering the imaging optics. The exemplary eye tracking sensor device can include a photodetector array to detect the inputted light transmitted through the imaging optics. In implementations of the exemplary eye tracking sensor device, the multiple light source is configured to emit multiple modulated light beams (e.g., at different modulated frequencies) that can be retroreflected from the eye and be received by the photodetector array via the imaging optics of the exemplary eye tracking sensor device. For example, the photodetector array can be configured to include pixels and a demodulation circuit to discern between light of the modulated frequencies emitted by the multiple light source unit from other light without such modulation (e.g., such as ambient light in the surrounding environment). In some implementations, the exemplary eye tracking sensor device can be communicatively coupled with a processing unit of a user device.

Figure 16:
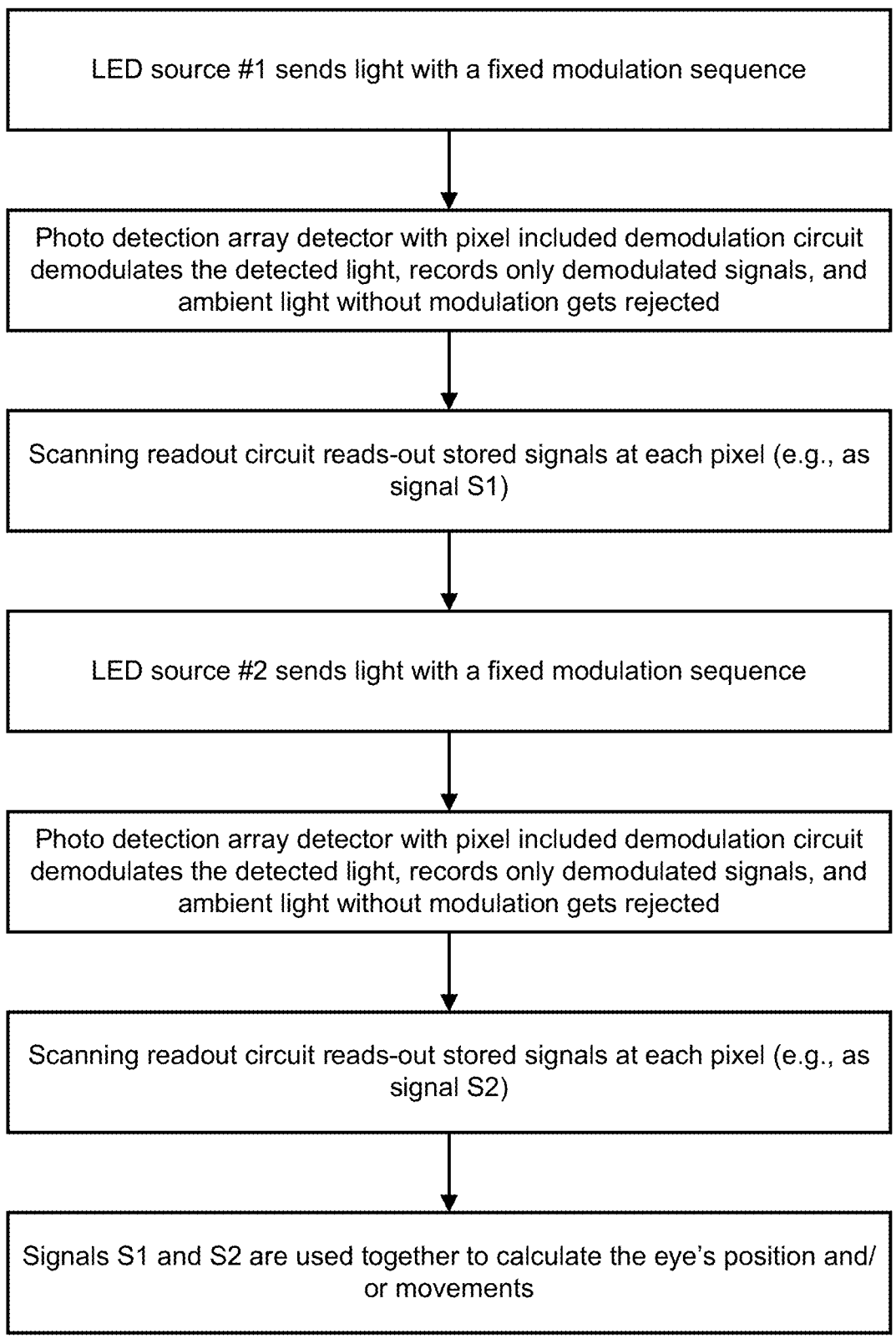
FIG. 16 shows a process diagram of an exemplary method for detecting multiple modulated eye tracking sensor signals.

FIG. 16 shows a process diagram of an exemplary method for detecting multiple modulated eye tracking sensor signals. The exemplary method can include a process to emit a first light beam (e.g., LED light) with a fixed modulation from a first light emitting source (e.g., LED light source) of an eye tracking sensor device of the disclosed technology, e.g., such as that in FIG. 15. The exemplary method can include a process to detect the first modulated light beam at a photodetector array including a pixel-included demodulation circuit. The method can include a process to demodulate the detected first modulated light, in which only demodulated signals are recorded and stored (e.g., in a memory, which can be configured in the demodulation circuit), and light not of the first modulated frequency (or frequencies) are rejected. The method can include a process to read out the stored signals corresponding to the first modulated light for each pixel, e.g., using a scanning readout circuit coupled to or included in the demodulation circuit. The exemplary method can include a process to emit a second light beam (e.g., LED light) with a fixed modulation from a second light emitting source (e.g., LED light source) of an eye tracking sensor device of the disclosed technology, e.g., such as that in FIG. 15. The exemplary method can include a process to detect the second modulated light beam at a photodetector array including a pixel-included demodulation circuit. The method can include a process to demodulate the detected second modulated light, in which only demodulated signals are recorded and stored (e.g., in a memory, which can be configured in the demodulation circuit), and light not of the second modulated frequency (or frequencies) are rejected. The method can include a process to read out the stored signals corresponding to the second modulated light for each pixel, e.g., using a scanning readout circuit coupled to or included in the demodulation circuit. The method can include implementing the emitting, detecting and demodulating, and read-out processes of the exemplary first and second modulated light sequentially, as shown in FIG. 16, or concurrently, as shown in FIG. 17.

Figure 17:
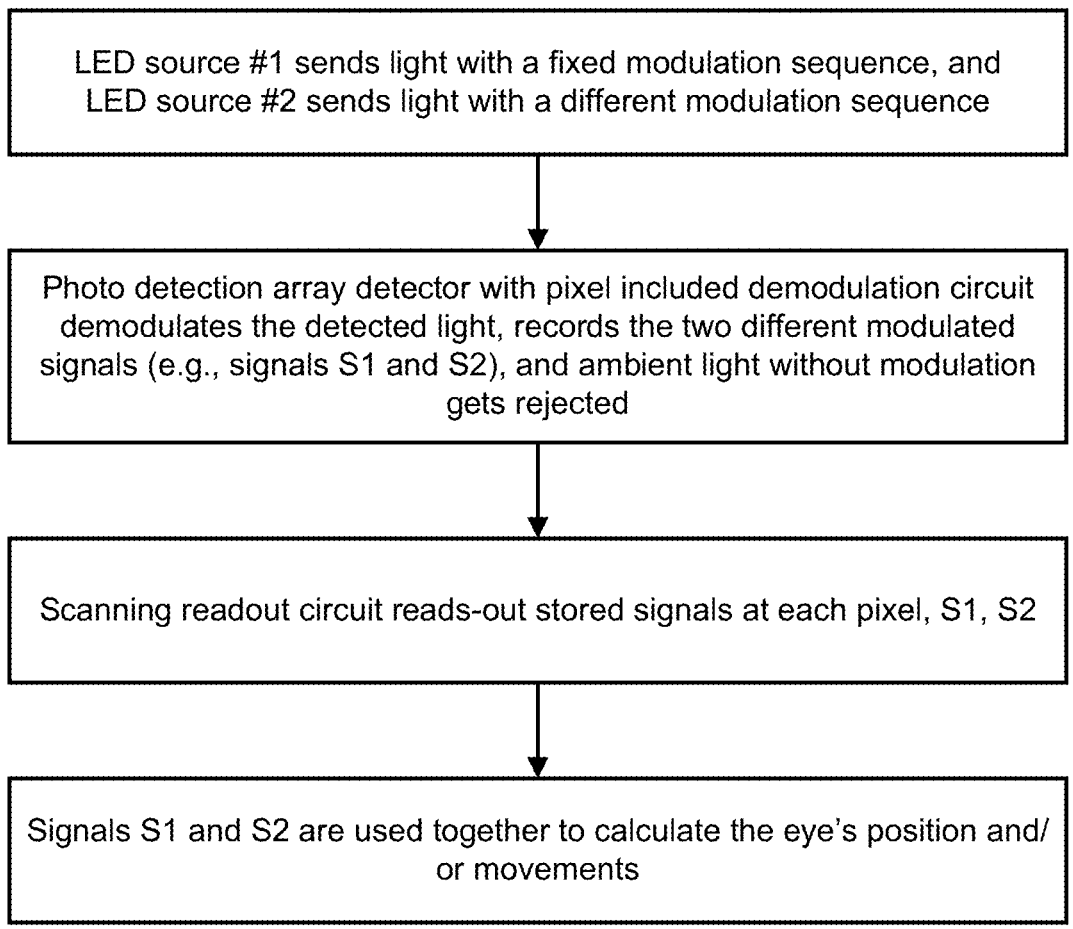
FIG. 17 shows a process diagram of an exemplary method for concurrently detecting multiple modulated eye tracking sensor signals.

FIG. 17 shows a process diagram of an exemplary method for concurrently detecting multiple modulated eye tracking sensor signals. For example, two different light sources can be used that are different in wavelength, e.g., in which the first light source emits light at wavelengths>850 nm, e.g., in some examples at 940 nm, and in which the second light source emits light at wavelengths<850 nm, e.g., at 780 nm. For example, the exemplary wavelengths can be used because the eye crystal can have different absorption on the two different wavelengths, whereas the human skin and other backgrounds have little difference to these two wavelength. By comparing the S1 and S2 signals, one can further reject the back ground signals. In other implementations, the two light sources can also be of the same wavelength and/or same modulation frequency but with a well defined phase difference, such as a phase difference of π, so that the processor can process the signals to extract information on the eye position or movement.

Functioning like a regular mouse, a proposed "eye mouse" module controls the computer cursor on a display by tracking and detecting the user's eye gaze. In some implementations, when a user slightly rotates or moves a mobile device, or rotates or moves his/her head, or rotates/moves the mobile device while rotating/moving the head, the cursor is continuously moved to a desired location of the user. Hence, the user may regard the mobile device as a regular mouse in such applications.

When operating an eye mouse module, which is integrated with a mobile device, light sources (which is part of the eye mouse module) on the mobile device can project light towards user. The retroreflected light from user's eyes return to the light sources with a small amount of divergence. However, the face of the user and other surfaces can scatter the light from the light sources and the scattered light can return to the light sources. Assuming eye pupil aperture is 3 mm in diameter, and the face and other surfaces have a total area of about 5000 times of the eye pupil area. This example means that only 1/5000 light returned to the light sources may be useful, which represents a serious problem for detecting the useful signal. In some embodiments, an eye mouse module is configured with a self-cancelation structure to reject background signals due to scattering from face and other object surfaces, so that only eyes or similar optics can be tracked while operating the eye mouse.

Figure 18A:
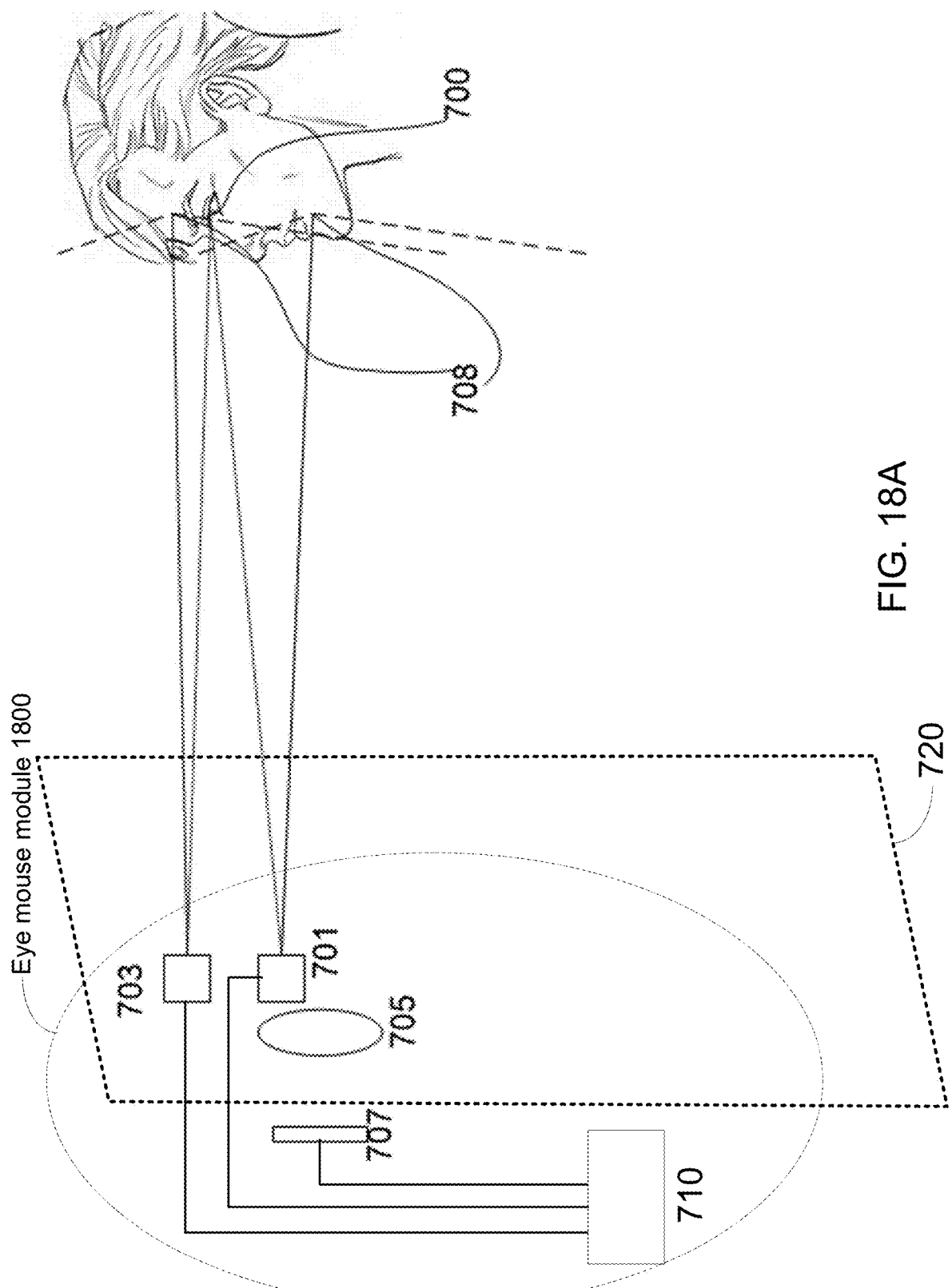
FIG. 18A shows a diagram of an exemplary eye mouse module which includes eye sensor mechanism and a self-cancellation structure.

FIG. 18A shows a diagram of an exemplary eye mouse module 1800 which includes eye sensor mechanism and a self-cancellation structure. Note that eye mouse module 1800 is typically located on a device including a display screen. In this exemplary implementation, two groups of light sources in eye mouse module 1800 are used to facilitate detecting the eye pupil. More specifically, first group of light sources 701 is placed close to the receiving sensor 707 and the axis of lens 705. Light sources 701 may be referred to as the "co-axis light sources." The other group of light sources 703 is placed further away from the axis of lens 705. Light sources 703 may be referred to as the "reference light sources." Typically, the distance between reference light sources 703 and lens 705 may be set to about 5 mm. The light beams from light sources 701 and 703 are then projected toward the user. In some embodiments, each of the first and second groups of light sources 701 and 703 comprises a single light source, such as an LED.

In typical situations that the users hold the device that includes the eye mouse module by hands, the light power projected on the eye pupil 700 is significantly less than (e.g., only about 1/5000) the light power that is projected on the user's face 708 and other surfaces such as user's shoulder. The retroreflected light from the user's eyes may be distributed within a limited area (e.g., ~10 mm diameter aperture area at 600 mm distance) with the light source at the center of the aperture. The light scattered from the face and other surfaces is typically distributed into a much larger area, which may be described by a half globe if Lambert scattering model is used (e.g., ~$2\pi R^2$ or 251000~2262000 $mm^2$). Note that if the receiving lens 705 has an aperture smaller than the retroreflected light beam size, the contrast between the retroreflected light and the scattered light is typically only 0.64~5.8. This low ratio means that the sensor 707 has to have multiple elements. For example, if the sensor has N detector elements, the contrast can be improved by N times at the eye image location.

The design illustrated in FIG. 18A provides a technique to improve the eye detection contrast without the need of increasing sensor elements. In particular implementations, the two groups of light sources 701 and 703 can be of similar wavelengths and substantially the same spatial power distribution. This can be realized by adjusting the drive current of light sources 701 and 703. The two groups of light sources can be modulated with substantially the same frequency and same modulation depth. However, the modulations performed on the two light sources have a phase difference ~180°. Note that the received scattered light from human face and other scattering surfaces include the scattered light of both light sources 701 and light sources 703. Because of the modulation phase difference of ~180°, the scattered light from these two sources are substantially cancelled out each other, and the remaining portion of the scattered light constitutes a stable power which generates DC signals. In some implementations, a DC-rejection filter circuit is used to filter these high DC ratio signals. Moreover, the retroreflected light from light sources 701 and 703 typically has a very small divergence angle, and the configuration illustrated in FIG. 18A allows sensor 707 to receive much more retroreflected light from co-axis light sources 701. As a result, the received AC signal is primarily from the retroreflection light of the co-axis light sources 701. This result is referred to as "self-cancellation."

Further referring to FIG. 18A, the output signals from sensor 707 are coupled to a processing unit 710 of the eye mouse module, which is operable to run programs to process the AC signals generated by sensor 707 to determine a point of gaze of the eye of the user on a display 720. More specifically, the processing unit can determine the point of gaze based on the retroreflected light corresponding to the co-axis light sources 701 and the reference light sources 703. In some embodiments, the processing unit can determine the point of gaze based primarily on the retroreflected light corresponding to the co-axis light sources 701. The processing unit 710 can then display or update the display of a cursor on display 720 based on the determined point of gaze. Note that as the eye mouse module continuously tracks the relative movement (both linear and rotational) between display 720 and the eye of the user 700, the processing unit continuously updates the positions of the cursor on display 720 based on changing points of gaze of the eye.

Figure 18B:
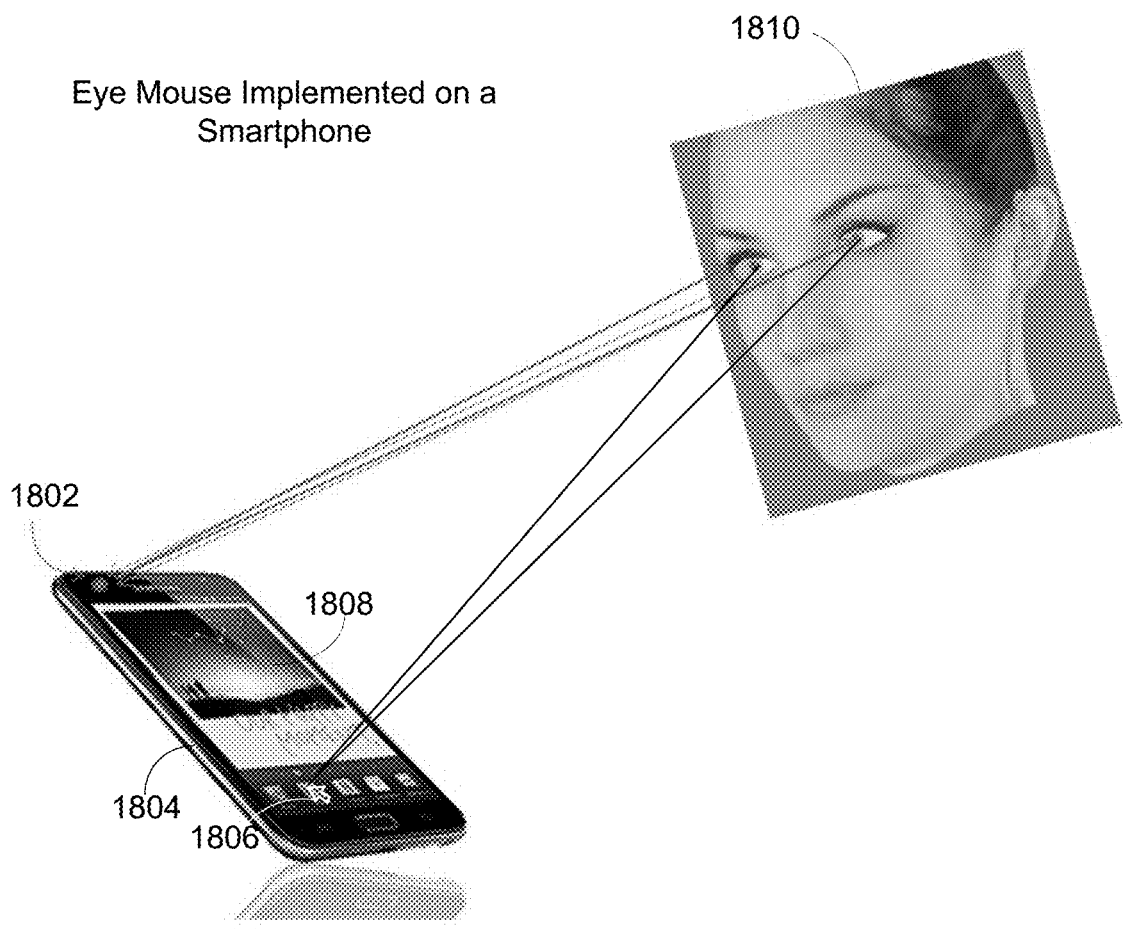
FIG. 18B shows a diagram of an exemplary eye mouse device integrated with a smartphone.

FIG. 18B shows a diagram of an exemplary eye mouse module 1802 integrated with a smartphone 1804 which displays a cursor 1806 on the display screen 1808 based on the determined point of gaze of user 1810.

Figure 19A:
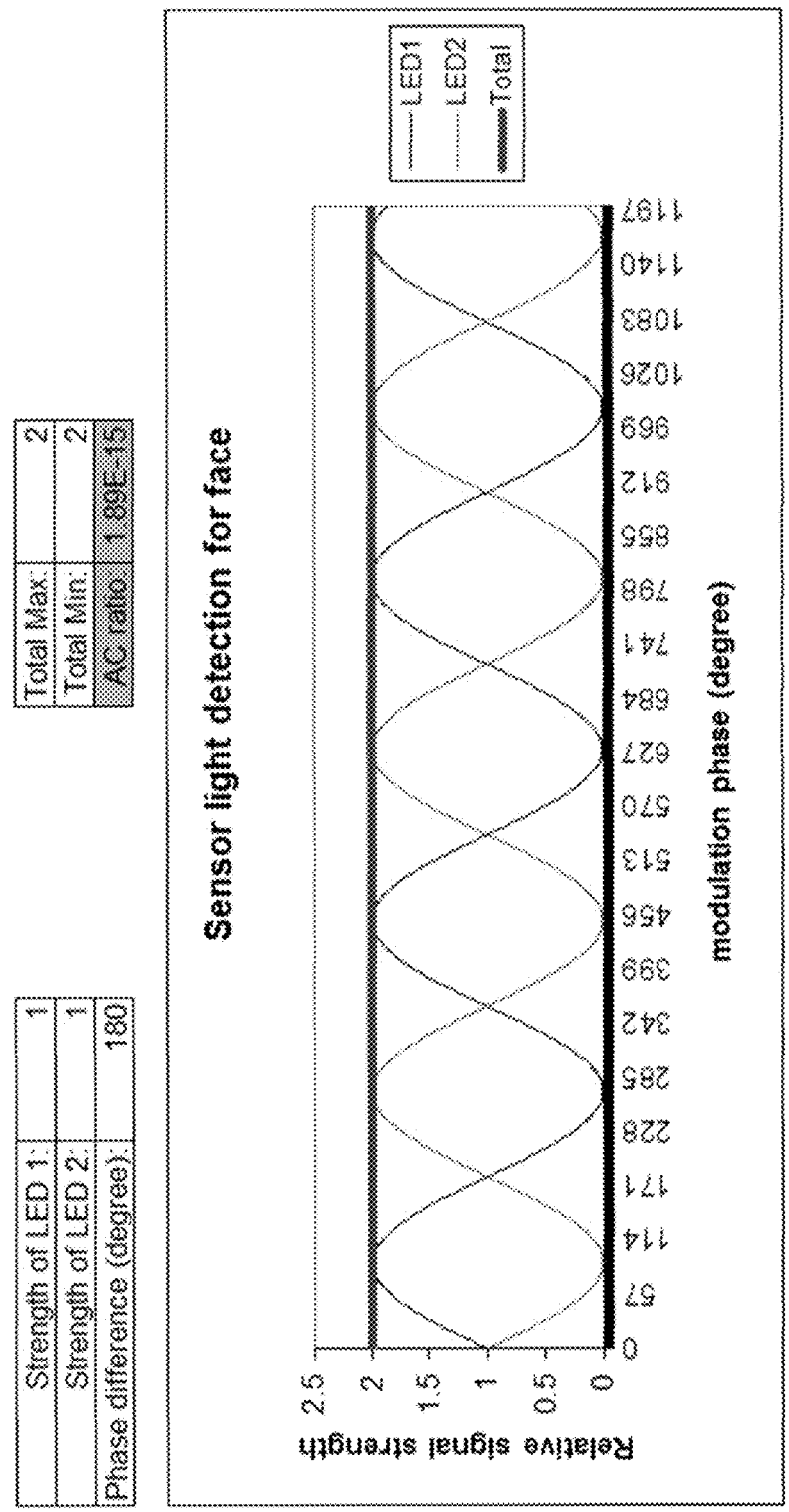
FIG. 19A shows a simulation result of an exemplary eye mouse module using the self-cancellation structure when the two groups of light sources are perfectly matched.

FIG. 19A shows a simulation result of an exemplary eye mouse module using the self-cancellation structure when the two groups of light sources are perfectly matched. In this embodiment, the two perfectly-matched light sources have the same strength, the same modulation profile and an opposite phase. Moreover, the scattering light from the face and other surfaces has mostly an DC output which is rejected by the filter circuit. As a result, the detected AC signal component substantially corresponds to the eyes. It is observed that the face and other scattering surface cause a 41% increase of probe light noise. This is generally negligible comparing with the noise from the ambient background light.

Figure 19B:
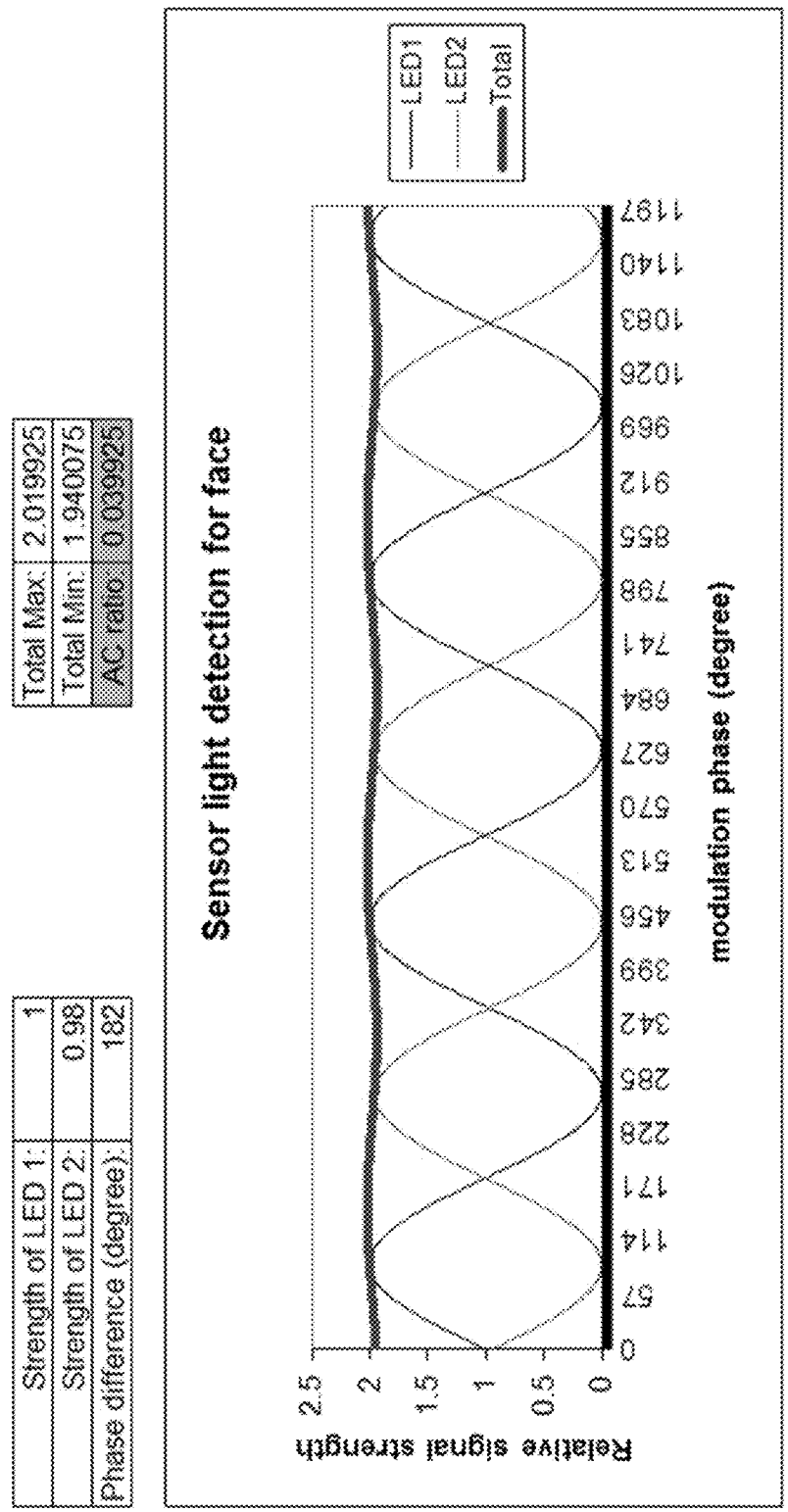
FIG. 19B shows a simulation result of an exemplary eye mouse module using the self-cancellation structure when the two groups of light sources are matched with a small amount of difference.

FIG. 19B shows a simulation result of an exemplary eye mouse module using the self-cancellation structure when the two groups of light sources are matched with a small amount of difference. In this example, the two light source has a 2% difference in strength, and the modulation phase difference is 178° instead of 180°. The simulation result shows that such a design achieved ~25 times signal to background contrast improvement, or ~18 times SNR improvement.

Note that using the design shown in FIG. 19A and FIG. 19B, the pupil size change can be conveniently and reliably detected by calibrating the received AC signal component with respect to the outputs of the light sources and the ambient light strength. More specifically, the retroreflection signal intensity change can be used to determine the pupil size change by measuring the received retroreflection signal strength change or by directly counting number of the pupil image occupied sensor elements. Moreover, the received retroreflection signal can also be used to determine whether a person is looking at screen and which region on the screen the person is looking at.

Note that the system does not need to compare between two frames to reject background in order to generate the eye tracking signals. Instead, the eye tracking signals are generated by sensor 707 in real time. This is very useful especially during slow frame rate sensing. Further, the proposed eye mouse structure can reduce the requirement on number of detector elements by a factor of ~18 or better. For example, a 10×20 sensor of self-cancellation eye mouse module can achieve better result than 40×80 sensor using direct detection without the self-cancellation design.

Figure 20A:
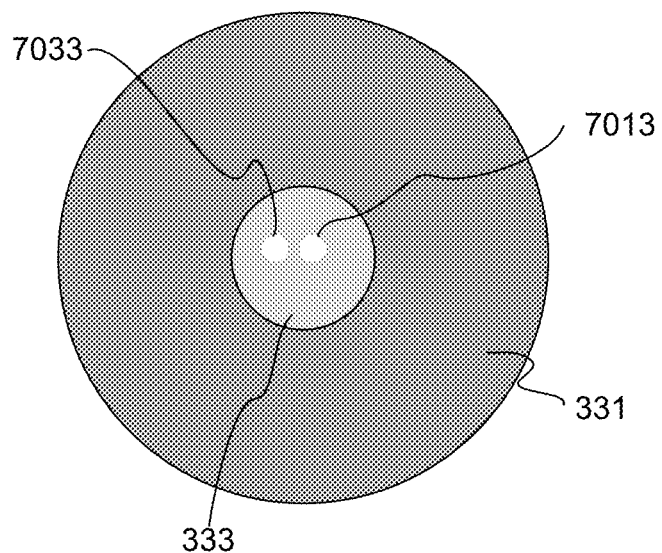
FIG. 20A shows a schematic of the eye image when both co-axis light source and the reference light source in FIG. 18A are turned.

FIG. 20A shows a schematic of the eye image when both co-axis light source and the reference light source in FIG. 18A are turned on. Note that pupil 333 is bright. The bright spot 7013 on the right within pupil 333 represents the corneal reflection image of co-axis light sources 701 in FIG. 18A, and the bright spot 7033 on the left represents the corneal reflection image of the reference light sources 703 in FIG. 18A. Because the reflected light from corneal surface 331 has a wide divergence angle and the co-axis light source 701 and the reference light sources 703 are close to each other, the sensor 707 in FIG. 18A receives same ratio of light power reflected by the corneal surface 331 under the co-axis light sources 701 illumination and under the reference light sources 703 illumination. In other words, the eye mouse sensor does not distinguish the two light sources' corneal reflections unless the sensor resolution is extremely high. Due to the self-cancellation design wherein the two corneal reflections have the opposite phase, the corneal reflection contribution can be eliminated. Similarly to the corneal reflection cancellation, the influence of the reflection from other smooth surfaces, such as glasses frame surfaces, can also be also removed. Consequently, the self-cancellation design of eye mouse illustrated in FIG. 18A significantly improves the eye pupil detection. In a well-calibrated eye mouse sensor module, the AC signal strength directly reflects the eyes' retroreflection strength which is proportional to the eye pupil size.

Figure 20B:
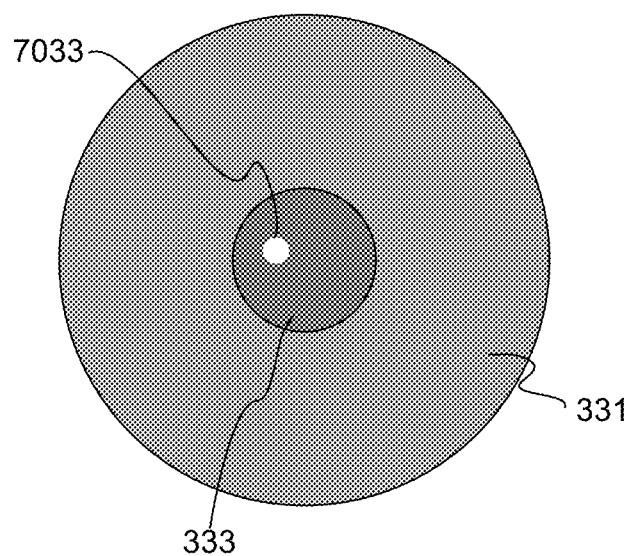
FIG. 20B shows a schematic of the eye image when only the reference light source in FIG. 18A is detected.

FIG. 20B shows a schematic of the eye image when only the reference light source in FIG. 18A is detected. In this situation, the pupil area 333 is dark. The corneal reflection image 7033 of the reference light sources 703 in FIG. 18A becomes detectable. This situation can be realized either by turning off the co-axis light sources 701, or by modulating the two group of light sources at difference frequencies so that the detection is done in different band.

Figure 20C:
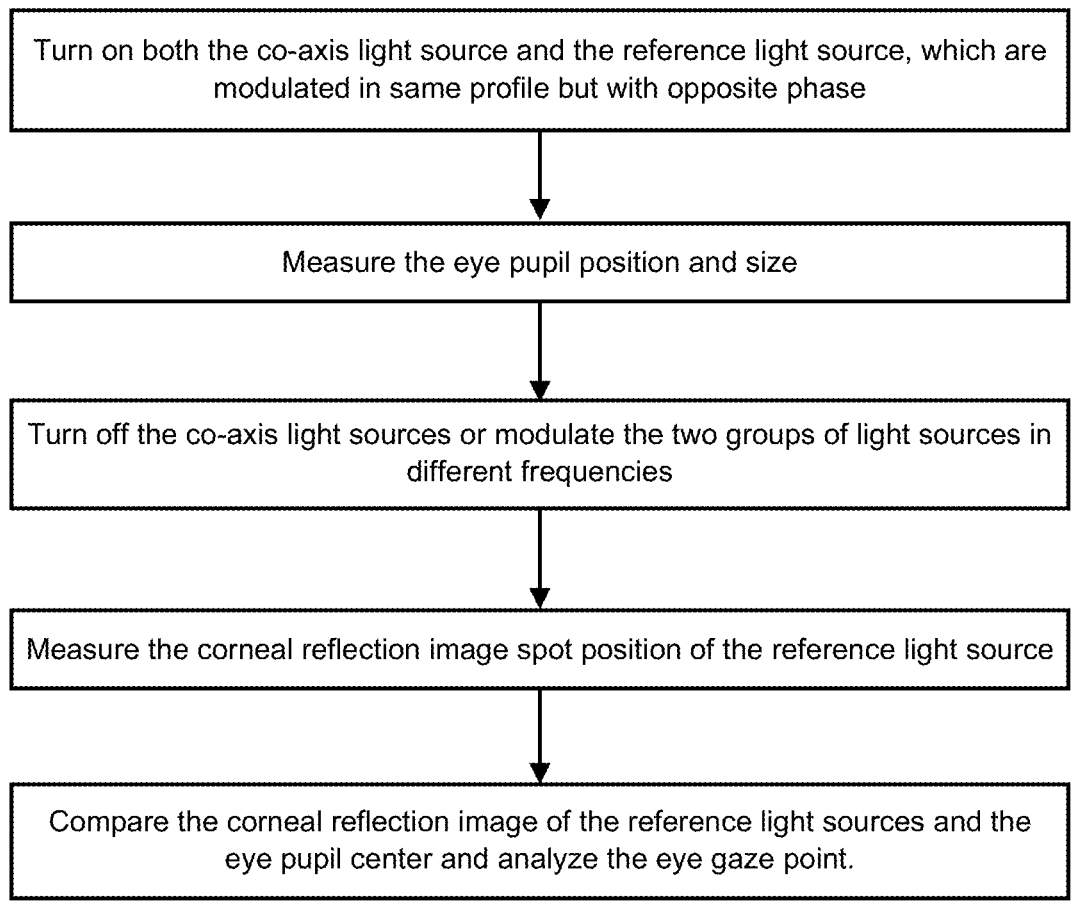
FIG. 20C presents a flowchart illustrating an exemplary process of tracking the eye gaze point.

FIG. 20C presents a flowchart illustrating an exemplary process of tracking the eye gaze point. The process is described in the context of FIG. 18A and FIGS. 20A and 20B. The process may begin by turning on both the co-axis light source and the reference light source, wherein both of the light sources are modulated with the same profile (e.g., same frequency and depth) but with substantially opposite phase. Next, the eye pupil position and size are measure. Once the eye pupil positions are measured, the eye mouse sensor can focus on the nearby detector elements to detect the corneal reflection image 7033 of the reference light sources 703. More specifically, the process can either turns off the co-axis light source or modulate the two groups of light sources at different frequencies. The process subsequently measures the corneal reflection image spot position of the reference light source. The process can then compare the corneal reflection image spot position of the reference light source and the position of the eye pupil center. The offset between the eye pupil center and the corneal reflection image spot provides the information about the eye gaze direction. The process can also analyze the eye gaze point. The distance between the two images of both eyes on the sensor 707 in FIG. 18A provides a measure scale to calibrate the eye gaze direction.

Figure 21:
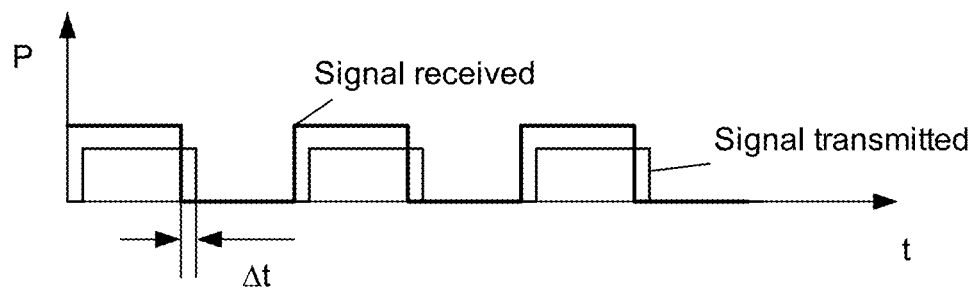
FIG. 21 shows the range finding function of the proposed eye mouse module.

FIG. 21 shows the range finding function of the proposed eye mouse module. With the eyes' retroreflection light, the proposed eye mouse module can realize a 3D detection function. More specifically, the range or the distance between the light sensor and the user's eyes may be measured by comparing the phase shift. Note that the received retroreflection light has a time delay with respect to the probe light that is transmitted towards the user's eyes. The processor in the eye mouse module can measure the distance from the sensor to the user's eyes by measuring the phase delay between the transmitted light signal and the received light signal. Note that the determined range or distance information can be combined with the determined point of gaze in the 2-D plane of the display to generate 3D eye-tracking data.

Figure 22A:
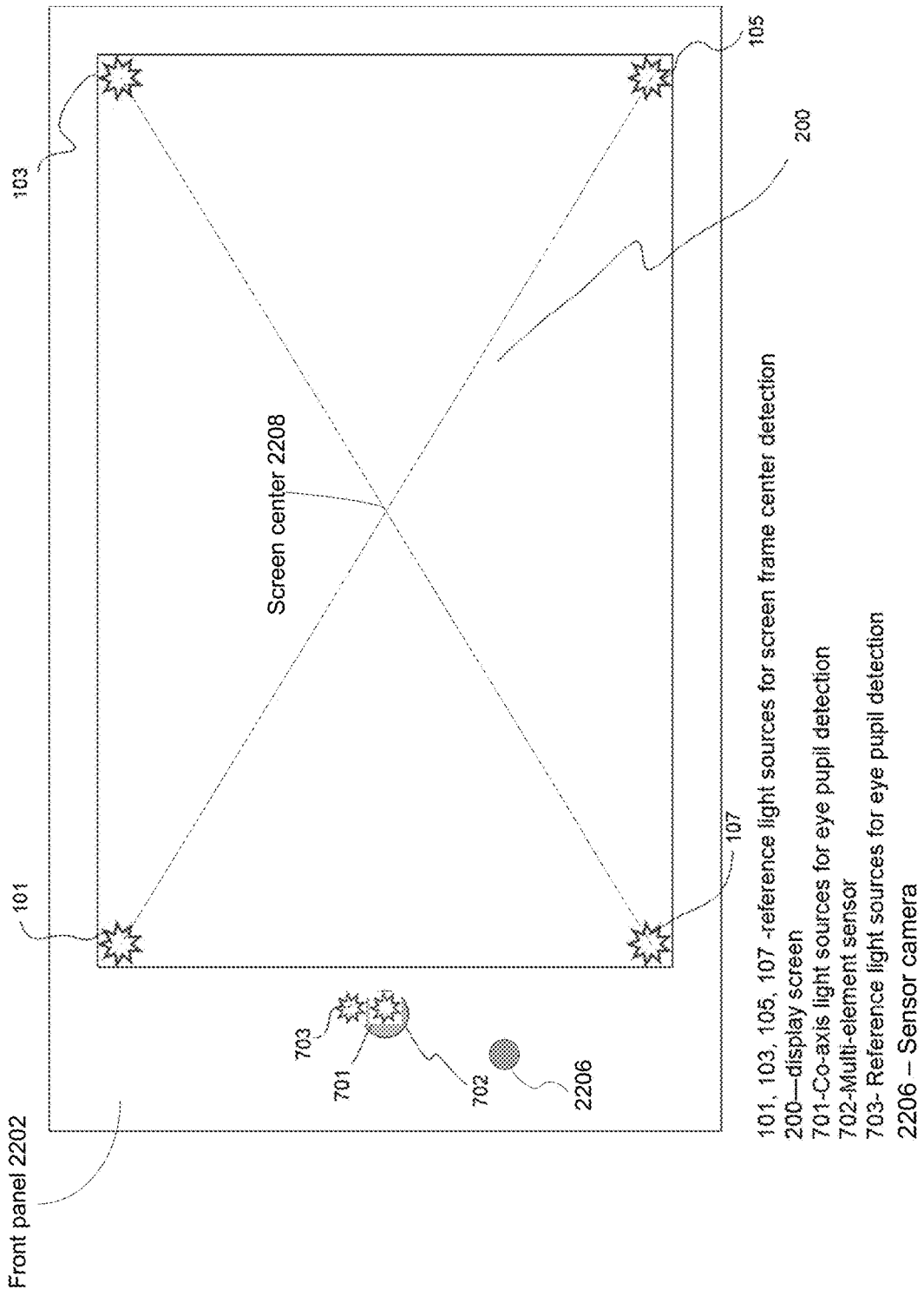
FIG. 22A shows an exemplary implementation of a calibration-free eye mouse module on a mobile device.

FIG. 22A shows an exemplary implementation of a calibration-free eye mouse module on a mobile device. More specifically, FIG. 22A shows an exemplary mobile device 2200 comprising a front panel 2202, a display screen 200 shown as a rectangular area within the front panel 2202, and multiple sensors and light sources. A calibration-free eye mouse module includes light sources 701, 703, and sensor assembly 702, which are located on the front panel 2202 of mobile device 2202 but outside of display screen 200. In accordance with the above-described techniques, light sources 701, 703, and sensor assembly 702 are configured in a self-cancellation design to detect the eye pupil center coordinates. In other words, sensor assembly 702 can perform all the functions of sensor 707 described in conjunction with FIG. 18A, including to detect the eye pupil positions. In one embodiment, light sources 701 are co-axis light sources, light sources 703 are off-axis reference light sources, and sensor assembly 702 is a multi-element sensor, for example, sensor assembly 702 can include a high definition photodiode array.

The calibration-free eye mouse module also includes a group of reference light sources 101, 103, 105, and 107. In one embodiment, reference light sources 101, 103, 105, and 107 are located within the display screen 200 at the four corners of the display screen 200 (i.e., one reference light source for each corner), and are placed under the display screen 200's cover glass. This arrangement is practical for mobile devices that have limited frame margins. In other embodiments, reference light sources 101, 103, 105, and 107 can be positioned slightly outside the display screen 200 and near the four corners of the display screen 200 (i.e., one reference light source near each corner), or they can be positioned right on each corner of the display screen 200. In the embodiment shown, the four reference light sources 101, 103, 105, and 107 are positioned symmetrically to the four corners of display screen 200 to define a rectangular area, wherein the center of the defined rectangular area coincides with the center of the display screen 200, which is referred to as the "screen center" 2208.

In some embodiments, to determine the screen center 2208 coordinates, reference light sources 101, 103, 105, and 107 emit light and beams of the emitted light can be directed toward a user's eyes. The cornea reflected light from the eyes forms image of each of the reference light sources 101, 103, 105, and 107 on sensor assembly 702. To adjust to the relative movement between the mobile device and user's eye or head, sensor assembly 702 can take frames of user's eye images in a given time interval. Further, sensor assembly 702 can take videos of user's eye for screen center coordinates detection.

In one embodiment, reference light sources 101, 103, 105, and 107 are modulated at different frequencies. Moreover, sensor assembly 702 can detect modulated light, either in high frame rate or in high frequency. Hence, by distinguishing the frequencies of the multiple sensor signals, sensor assembly 702 and associated circuitry can determine the positions of individual reference light sources 101, 103, 105, and 107. Similarly to the eye pupil coordinates detection using light sources 701, 703, screen center coordinates detection using modulation/demodulation techniques facilitates rejecting the effects of background light.

The calibration-free eye mouse module can also include a camera 2206 configured to detect the screen center coordinates of display screen 200. In the embodiment shown, sensor camera 2206 is located at a border region of front panel 2202 but outside of display screen 200 of mobile device 2200. In one embodiment, sensor camera 2206 is the original video camera of the mobile device 2200. In another embodiment, sensor camera 2206 is a dedicated camera for screen center detection. In a further embodiment, sensor camera 2206 is a high-definition (HD) camera. To determine the screen center 2208 coordinates, reference light sources 101, 103, 105, and 107 can emit light toward a user's eyes, and sensor camera 2206 can take frames of images of the user's eye including eye pupil, which has reflection images of the reference light sources 101, 103, 105, and 107. To adjust to the relative movement between the mobile device and user's eye or head, sensor camera 2206 can take frames of user's eye images in a given time interval. Sensor camera 2206 can to take videos of user's eye for screen center coordinates detection.

The calibration-free eye mouse module also includes a processing unit (not shown) coupled to sensor assembly 702 and sensor camera 2206 and also optionally coupled to reference light sources 101, 103, 105, and 107. The processing unit is configured to process the user's eye images captured by sensor assembly 702 or by sensor camera 2206 including the reflection images of light sources 101, 103, 105, and 107 to determine the screen center 2208 coordinates of display screen 200. In one embodiment, the processing unit for determining the screen center 2208 coordinates is the same processing unit for detecting the eye pupil center coordinates, such as processing unit 710 shown in eye mouse module 1800 in FIG. 18A. The processing unit is also configured to determine an eye gaze point coordinates on the display screen 200 based on the determined eye pupil center coordinates and the screen center coordinates, and subsequently generate an eye mouse cursor on display screen 200. More detail of the calibration-free eye mouse module is provided below in conjunction with FIGS. 23A-25E.

In some implementations, the eye gaze point coordinates can be determined by comparing the pupil center coordinates, determined by light sources 701, 703, and sensor assembly 702, and the screen center coordinates, determined by the reference light sources 101, 103, 105, and 107 and sensor assembly 702 or sensor camera 2206. The eye gaze point information can then be used as an "calibration-free" eye mouse cursor to be displayed on the screen of the mobile device, wherein such a cursor is not sensitive to the device movement and head movement. Note that the integration of multiple light sources and the detectors on a mobile device provide the capability for high speed communication between such mobile devices and between station and the mobile devices (more detail of this is provided below in conjunction with FIG. 31). Moreover, the pupil detection function of the eye mouse module can be used to scan the retina of user's eye for security and detail of which is provided below in conjunction with FIG. 32.

Figure 22B:
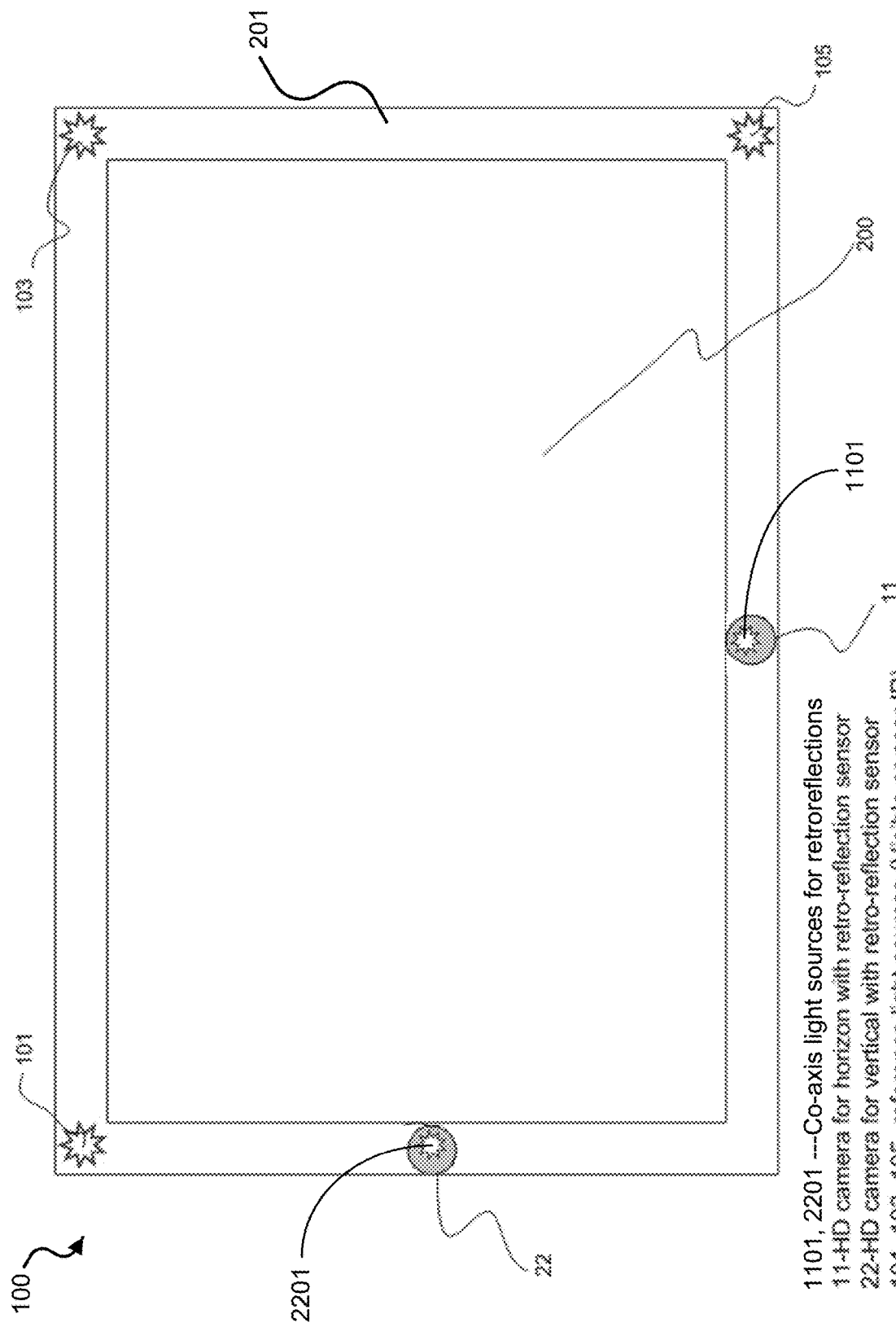
FIG. 22B shows a diagram of an exemplary eye mapping device of the disclosed technology including multiple optical imagers and multiple light sources integrated in a mobile communications and/or computing device and used for detecting eye movement and/or blinking to control functions of the mobile communications/computer device.

FIG. 22B shows a diagram of an exemplary eye mapping device 100 of the disclosed technology including multiple optical imagers 11 and 22 and multiple light sources 1101, 2201, 101, 103, and 105 integrated in a mobile communications, television, and/or computing device 201 and used for detecting eye movement and/or blinking to control functions of the mobile communications, television, and/or computer device 201. The multiple light sources of the eye mapping device 100 include light sources 1101 and 2201 that are configured to emit light that causes a retroreflection of the emitted light from the eye (e.g., retina) of the user of the device 201. For example, the light sources 1101 and 2201 can be configured as co-axis light emitting modules proximate to (e.g., 10 mm or less away from) or within the imager modules 11 and 22, respectively, such that the light emitted by the co-axis light emitter shares an axis with the light received by the respective imager module. For example, the emitted light by the light sources 1101 and 2201 can include visible light and/or near infrared light to produce the retroreflection from the eye of the user.

The multiple light sources of the eye mapping device 100 also include reference light sources 101, 103, and 105 that are configured to emit light that causes a reflection of the emitted light from the cornea of the user's eye. For example, the emitted light by the reference light sources 101, 103, and 105 can include visible light and/or near infrared (NIR) light to produce the corneal reflection from the eye of the user. In some examples, the reference light sources of the exemplary eye mapping device 100 can include two linear arrays of two or more light sources configured perpendicular to one another. As shown in FIG. 22B, for example, a first linear array is arranged horizontally and adjacent to the monitor screen 200 on the device 201 and including the reference light sources 101 and 103. For example, a second linear array is arranged vertically, e.g., perpendicular to the first array, and adjacent to the monitor screen 200 on the device 201 and including the reference light sources 103 and 105. The optical imager 11 is configured on the device 201 adjacent to the monitor screen 200 along a side parallel to the first array of the reference light sources 101 and 103 to detect inputted light into the imager 11 including a retroreflection from the eye of the user produced by the light sources 1101, and the corneal reflection from the eye of the user produced by reference light sources 101 and 103. The optical imager 22 is configured on the device 201 adjacent to the monitor screen 200 along a side parallel to the second array of the reference light sources 103 and 105 to detect inputted light into the imager 22 including a retroreflection from the eye of the user produced by the light sources 2201, and the corneal reflections from the eye of the user produced by reference light sources 103 and 105.

In some examples, the imagers 11 and 22 of the exemplary eye mapping device 100 can be structured to include a photodetector sensitive array to detect the inputted light into the imager and a bandpass filter to filtered the signal produced by the photodetector sensitive array. In some examples, the light sources (e.g., near infrared LEDs) of the exemplary eye mapping device 100 can be modulated at a particular frequency or frequencies, in which the light sources are optically coupled to a linear polarizer of the optical imagers 11 and/or 22 to transmit a modulated probe light from the device 100 that can be reflected by the eyes of the user.

The exemplary eye mapping device 100 can include a processing unit communicatively coupled to the optical imagers 11 and 12 and/or the light sources 1101, 2201, 101, 103, and 105 to process the captured images and/or photodetected signals as data. The processing unit can include a general purpose processor coupled to a memory unit to store the raw and processed data. The processing unit can be configured to execute methods to track the eye movements based on the detected retinal retroreflection and corneal reflection light signal data and control functions of the user device, e.g., including altering the display screen 200 of the user device 201. In some implementations of the exemplary eye tracking device 100, a processing unit including a processor and memory unit of the user device 201 is used to implement the data processing methods of the disclosed technology.

Figure 23A:
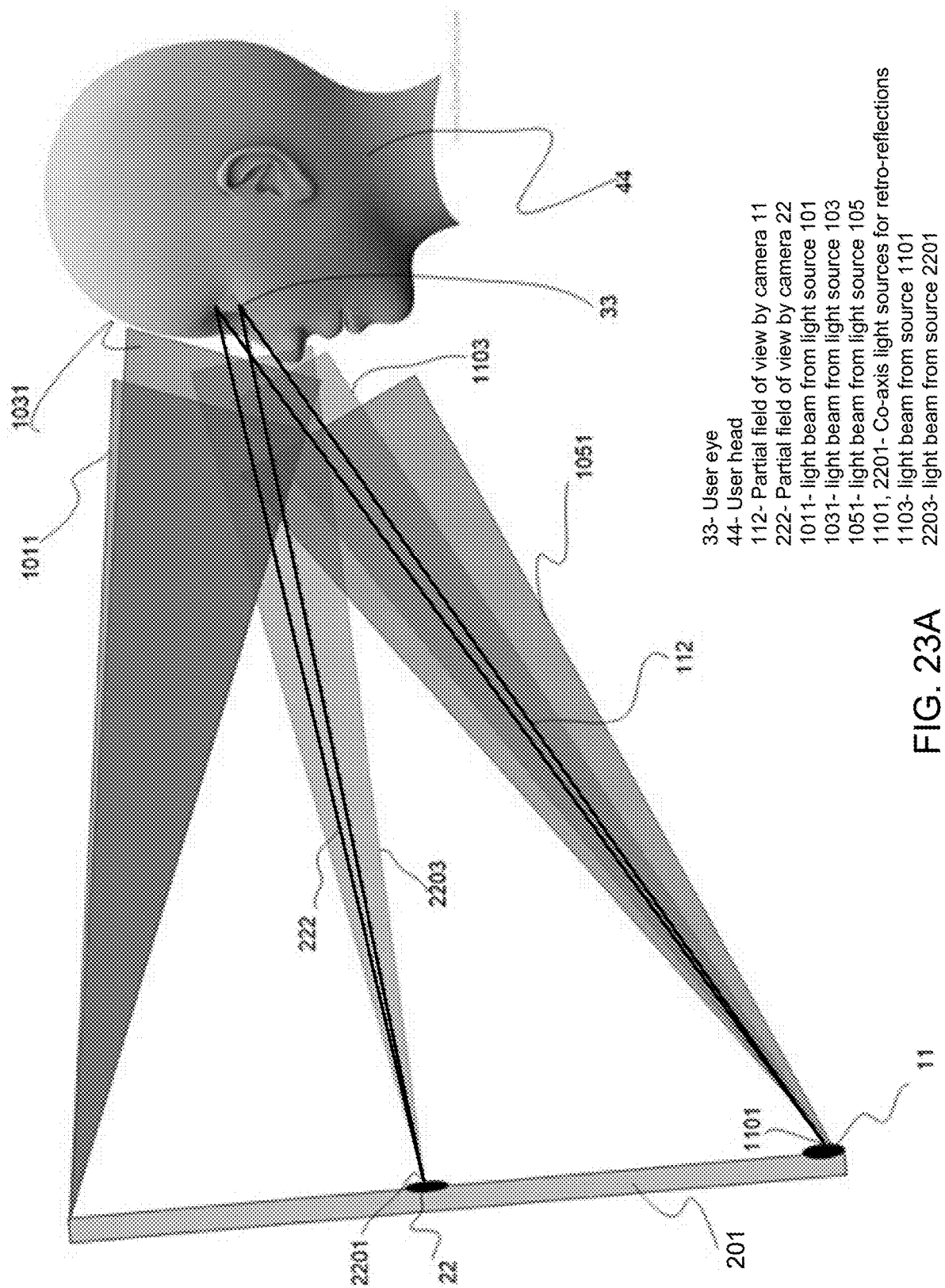
FIG. 23A shows a diagram depicting an exemplary implementation of the device to track and map the position and/or movements of a user's eyes, e.g., while viewing the monitor of the mobile communications/computer device.

FIG. 23A shows a diagram depicting an exemplary implementation of the device 100 to track and map the position and/or movements of a user's eyes, regardless of movements by the user's head 44, e.g., while viewing the monitor 200 of the device 201. For example, as depicted in the diagram of FIG. 10, a light beam 1011 produced by the reference light source 101 and a light beam 1031 produced by the reference light source 103 can generate a corneal reflection on the eye 33 of the user, which can be detected by the imager 11, e.g., off-axis, via its partial field of view 112. Similarly, for example, a light beam 1051 produced by the reference light source 105 and the light beam 1031 produced by the reference light source 103 can also generate a different corneal reflection on the eye 33 of the user, which can be detected by the imager 22, e.g., off-axis, via its partial field of view 222. Also for example, a light beam 1103 produced by the light source 1101 can generate a retroreflection on the eye 33 of the user, which can be detected by the imager 11, e.g., co-axis, via its partial field of view 112. Similarly, for example, a light beam 2203 produced by the light source 2201 can generate a retroreflection on the eye 33 of the user, which can be detected by the imager 22, e.g., co-axis, via its partial field of view 222.

Figure 23B:
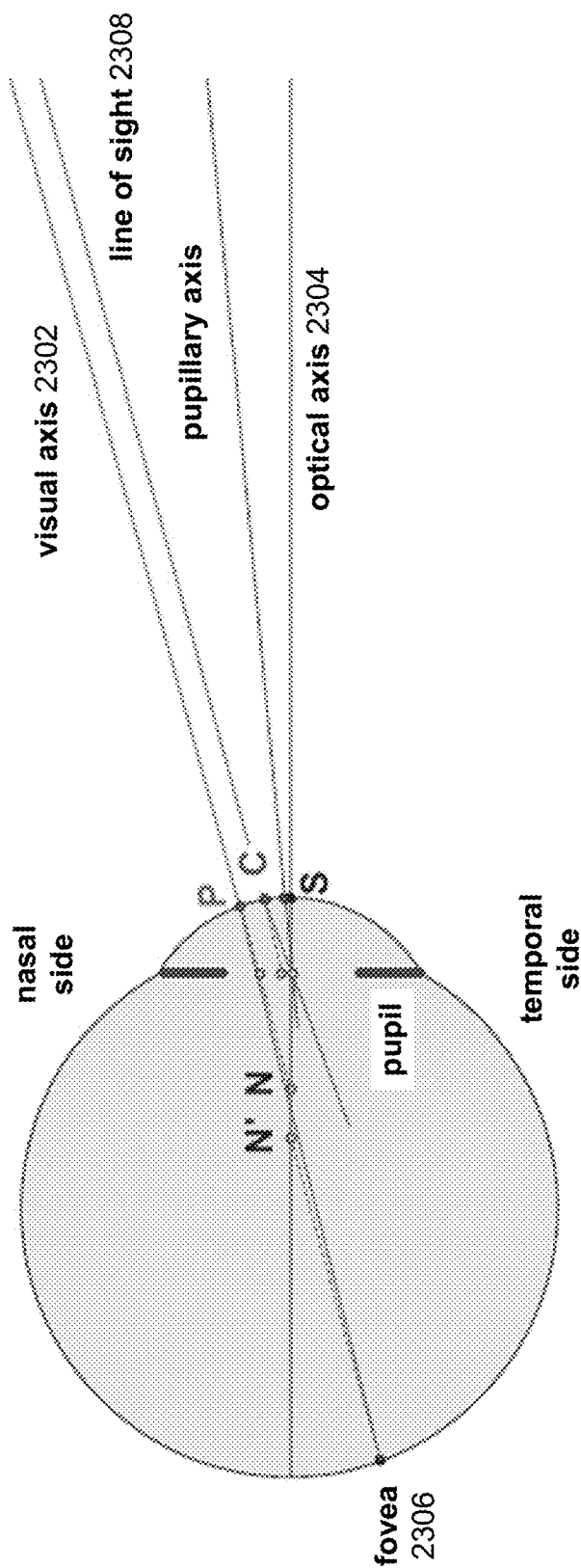
FIG. 23B shows a diagram of various optical axes of a human eye to illustrate the concept of the disclosed screen center coordinates detection technique.

FIG. 23B shows a diagram of various optical axes of a human eye 2300 to illustrate the concept of the disclosed screen center coordinates detection technique. As shown in FIG. 23B, the human eye 2300's visual axis 2302 differs from the optical axis 2304 because that the fovea 2306 is generally not located on the optical axis 2304. Typically, there is a 3° to 8° angle between the line of sight 2308 which is parallel to the visual axis 2302 and the optical axis 2304, while the fovea covers about 5° view angle. Furthermore, the center of the entrance pupil is actually shifted toward the nasal side because of the asymmetric structure of the human eye vision system. On the cornea surface, point C and point S can have a distance of about 0.2~0.55 mm.

FIG. 24 shows a diagram illustrating the concept of using the cornea surface as a reflection lens. The light shone onto the eye cornea surface is partially reflected to a proper direction. An object in front of the eye cornea surface, such as objection 2402, forms a reflection image 2404. In some implementations, the reflection image 2404 position can be determined by the sensor lens axis (e.g., that of receiving lens 705 in FIG. 18A), eye viewing direction, and the object location. When the sensor and the object locations are fixed, the eye viewing direction can be determined based on the reflection image positions. As shown in FIG. 24, the human eye cornea has a diameter of about 11.5 mm and a radius of about 7.86 mm, and an equivalent focal length of about 3.93 mm. Hence, at distance of 600 mm, a 120 mm×60 mm screen can form a reflection image of about 0.8 mm×0.4 mm.

Figure 25A:
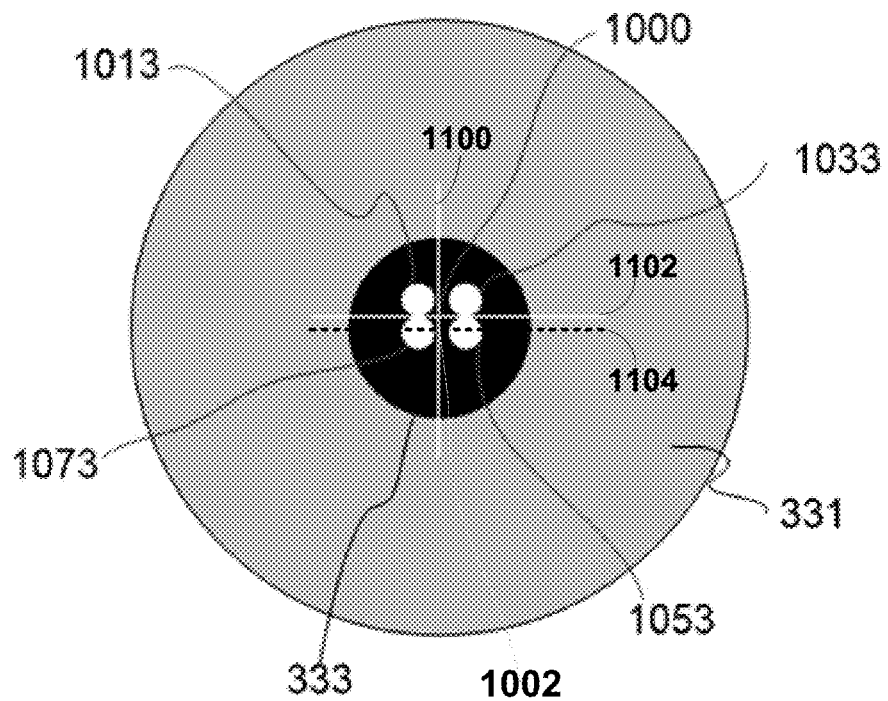
FIG. 25A shows a captured user's eye image including images of four reference light sources for detecting screen center coordinates of a display screen.

FIG. 25A shows a captured user's eye image including images of four reference light sources for detecting screen center coordinates of a display screen. As described above in conjunction with FIG. 22, reference light sources 101, 103, 105, and 107 can be used to measure the screen center 2208. The reflection images of these light sources are shown in FIG. 25A as light spots 1013, 1033, 1053, 1073, respectively. In one embodiment, these reference light sources are modulated at a frequency different from the modulation frequency of the pupil detection light sources 701 and 703 in FIG. 22A. Consequently, the pupil center detection and the screen center detection can be performed at the same time. In one embodiment, these reference light sources are modulated different modulation frequencies. Note that for smaller mobile devices, such as smart phones, the screen size is small. The reference light sources may be positioned at the four corners of the screen, as shown in FIG. 22A, to provide screen size information. Their reflection images can be very close to one another in the captured eye images, and the total size of the images is often smaller than the pupil size.

As shown in FIG. 25A, using the reflection images of the reference light sources 101, 103, 105, and 107, the screen center coordinates can be determined at location 1000 near the intersection of lines 1100 and 1102 in FIG. 25A, which is the center location of a rectangle formed by light spots 1013, 1033, 1053, and 1073. Note that using this technique, there is no need to distinguish the reflection images 1013, 1033, 1053, and 1073. Moreover, the eye pupil center coordinates can be determined as location 1002 near the intersection of lines 1100 and 1104 in FIG. 25A, which is below screen center location 1000. By comparing locations 1000 and 1002, the eye gaze location can be determined to be in the middle of the display screen in the horizontal direction and in the bottom half of the display screen in the vertical direction.

Note that screen center coordinates may also be determined using only three reference light sources, such as 101, 103, and 105, or 103, 105, and 107, as long as three of the four corners are used. In the case of using light sources 101, 103, and 105, light spots 1013, 1033, 1053 can be used to determine the screen center. In the case of using light sources 103, 105, and 107, light spots 1033, 1053, and 1073 can be used to determine the screen center. While it is possible to place only three reference light sources instead of four as shown in FIG. 22A, using four reference light sources can provide useful redundancy if during measurement one of the four reference light sources is accidently blocked, such as by user's finger, and in such cases, the remaining three reference light sources can be used to detect screen center coordinates.

Figure 25B:
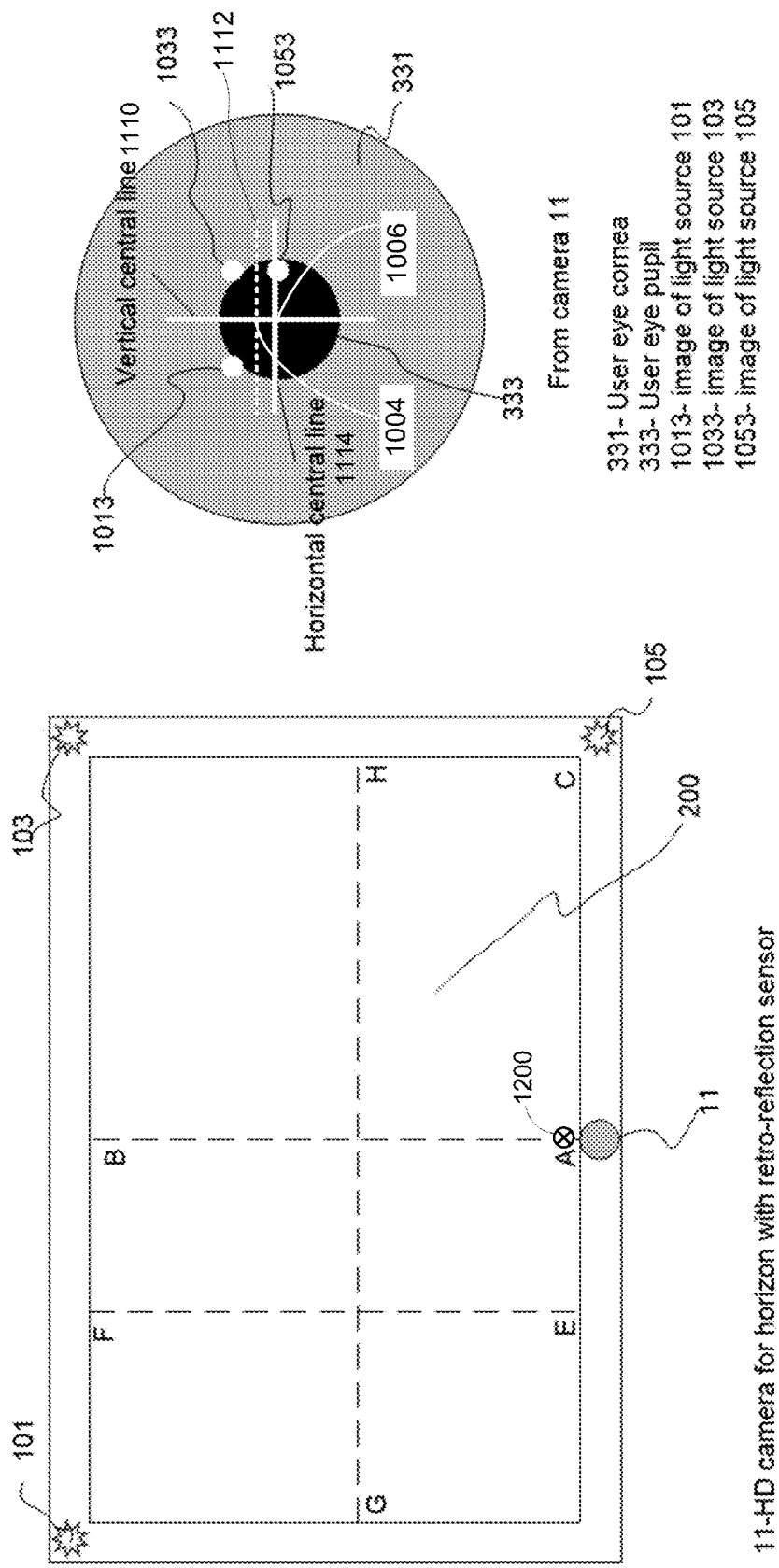
FIG. 25B shows a captured user's eye image including images of three reference light sources for detecting screen center coordinates of a display screen.

FIG. 25B shows a captured user's eye image including images of three reference light sources 101, 103, and 105 for detecting screen center coordinates of a display screen. In one aspect, the left image in FIG. 25B shows a monitor screen 200 and three reference light sources 101, 103, and 105 positioned near and slightly outside three corners of monitor screen 200. The intersection of dashed lines AB and GH defines the screen center location. An HD sensor camera 11 is positioned lightly outside screen 200 near point A and configured to capture the eye image. In this implementation, the vertical coordinate of the screen center needs to be calibrated because the sensor camera 11 is not placed in the middle of light sources 103 and 105. The right image in FIG. 25B shows the captured eye image which includes user's eye cornea image 331, eye pupil image 333, and the reflection images of the light sources as light spots 1013, 1033, and 1053 corresponding to reference light sources 101, 103, and 105, respectively.

In this example, the screen center coordinates can be determined at location 1004 near the intersection of lines 1110 and 1112. The eye pupil center coordinates can be determined as location 1006 near the intersection of lines 1110 and 1114 in FIG. 25A, which is below screen center location 1004. By comparing locations 1004 and 1006, the eye gaze location can be determined to be in the middle of the screen 200 in the horizontal direction and near the bottom of the screen 200 in the vertical direction. After determining the gaze point coordinates, an eye gaze point 1200 can be displayed on the screen 200 near point A.

Figure 25C:
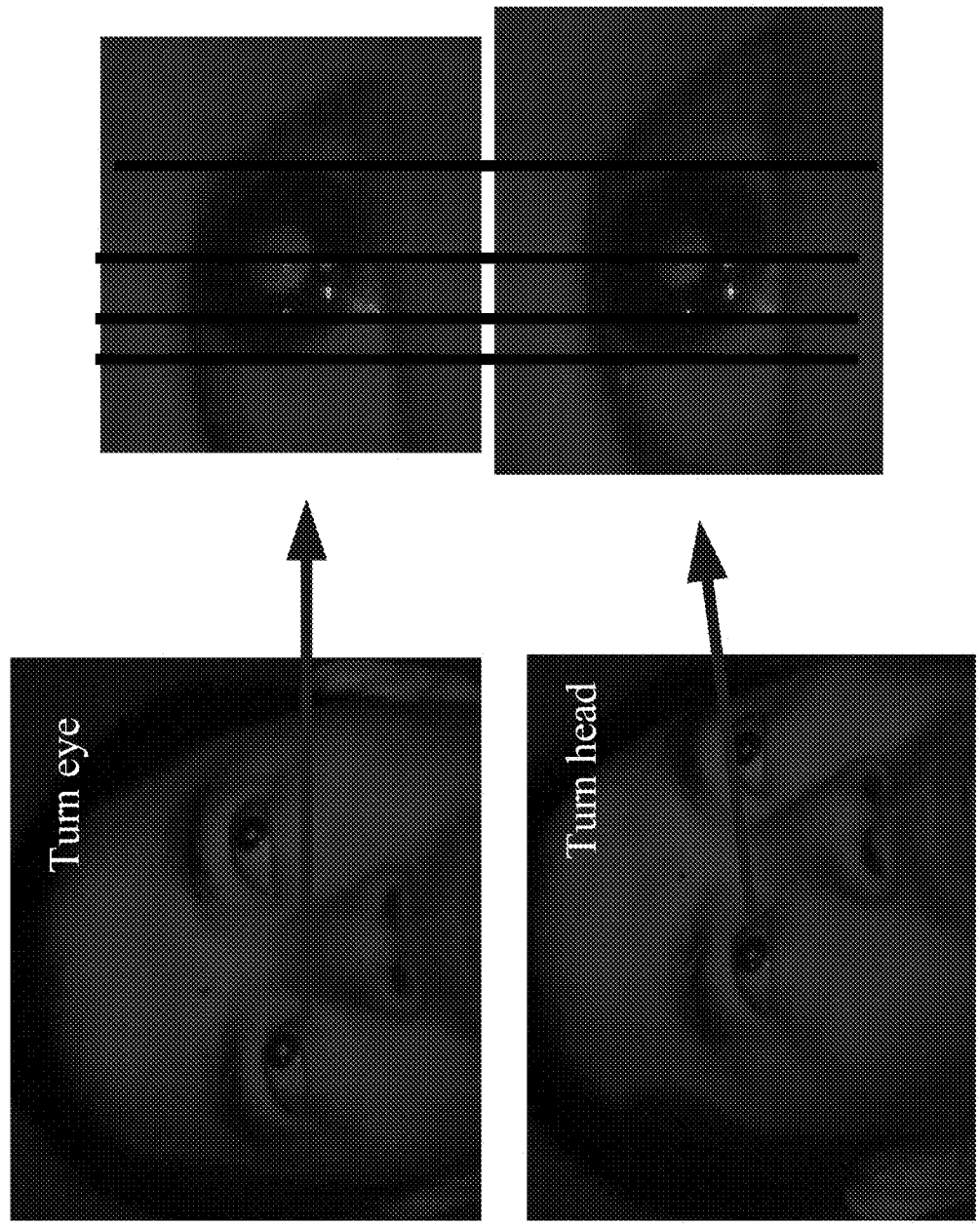
FIG. 25C shows the experimental results demonstrating that the determined eye gaze point of the proposed calibration-free eye mouse is insensitive to the head movement.

FIG. 25C shows the experimental results demonstrating that the determined eye gaze point of the proposed calibration-free eye mouse is insensitive to the head movement. More specifically, the upper part of FIG. 25C shows the effect of a user turning eyes and gazing at a point without turning the head. The corresponding camera image on the right shows multiple reflected images of multiple reference light sources and their positional relationships with respect to the pupil center location. The lower part of FIG. 25C shows the effect of the same user turning eyes and gazing at the same point while turning the head. The corresponding camera image on the right shows multiple reflected images of the same reference light sources and their positional relationships with respect to the pupil center location. As can be observed, the positional relationships in the upper and lower images are identically, suggesting that the head movement has no noticeable effect on the eye gaze point determination.

Once eye pupil center coordinates and the screen center coordinates are accurately measured, the viewing direction is absolutely measured. Because this technique automatically combines the screen signals and the pupil signals, the sensing is not sensitive to head movement and/or device movement. Also because the angle between the eye's optical axis and line of sight may be differ among different users, a general calibration of the eye mouse system can facilitate eliminating the system error. In other words, the pupil center shift described in conjunction with FIG. 23B should to be calibrated. In some implementations, the screen center coordinates calibration can be carried out by slightly adjusting the brightness of the reference light sources. Note that the general calibration for the difference between eye's optical axis and line of sight for a given user can be performed once and stored. Unless a new user is detected on the device, no new calibration is required. Moreover, in the beginning of using an eye mouse system, the system can simply retrieve the stored calibration profile for a regular user of the device without the need of a new calibration.

FIG. 25D shows a diagram and corresponding image from an exemplary implementation of the exemplary eye mapping device 1300 to determine a gazing point 1401 of the user's eye at a first instance. FIG. 25E shows a diagram and corresponding image from the exemplary implementation of the exemplary eye mapping device 1300 to determine the second gazing point 1402 of the user's eye at a second instance, in which the user has moved his gaze from an upper gaze position (e.g., exemplary gazing point 1401) on the user device to a central gaze position on the user device.

Figure 26:
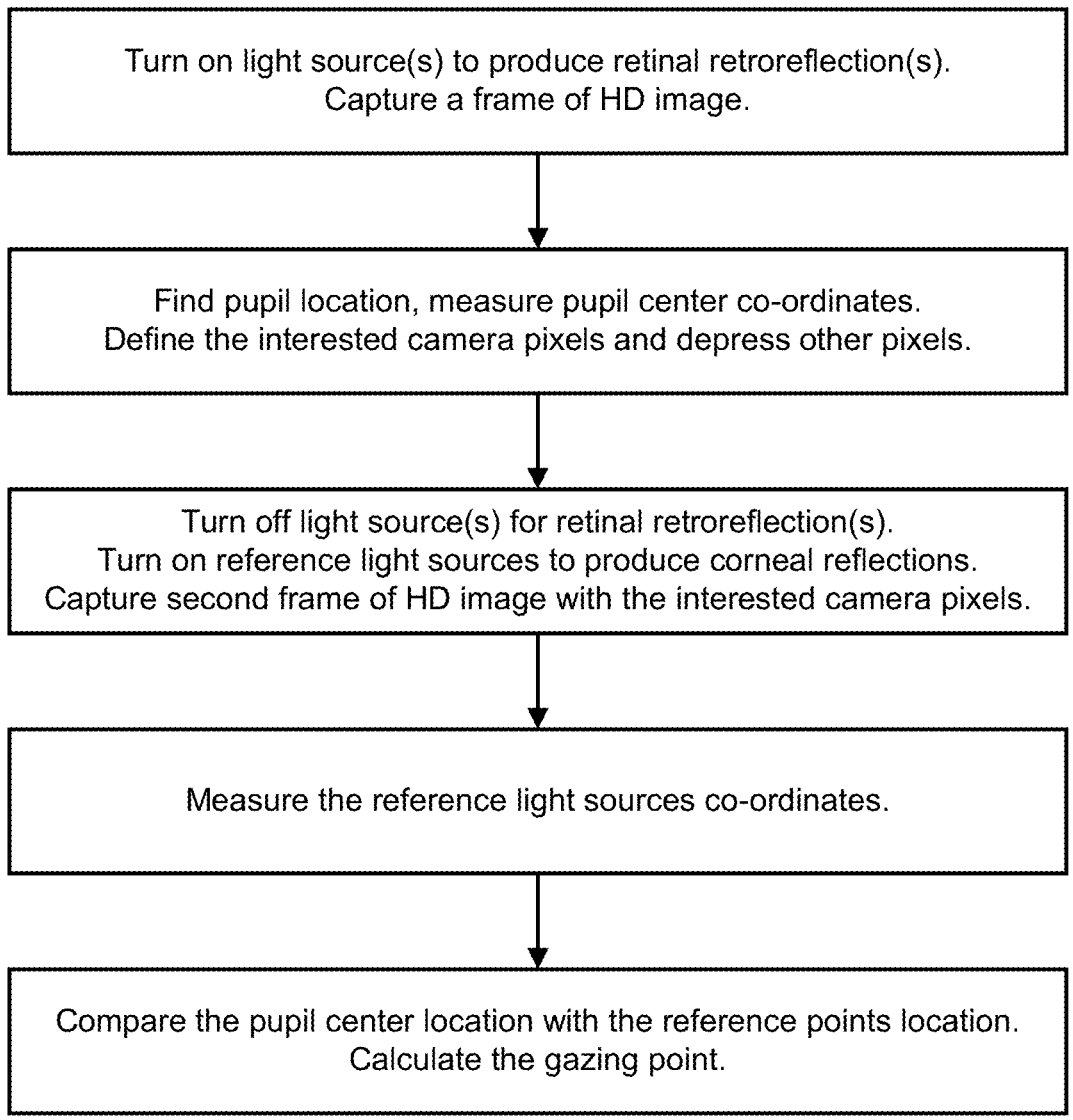
FIG. 26 shows a process diagram of an exemplary method for mapping eye movements using a user device by retroreflections from an eye.

FIG. 26 shows a process diagram of an exemplary method for mapping eye movements using a user device by retinal retroreflections and corneal reflections from an eye. The method can include a process to turn on one or more light source (e.g., co-axis light source 1101 and/or co-axis light source 2201) to produce one or more retinal retroreflections. The method can include a process to capture an image or frame of images (e.g., HD images), including video, of the eye, e.g., using one or more optical imagers (e.g., a camera) of the user device. The method can include a process to find the location of the pupil of the eye, e.g., using the one or more retinal retroreflections in the captured image(s), and determine the pupil center coordinates. In some implementations of the method, for example, the method can include a process to define imager/camera pixels of interest and depress other pixels. The method can include a process to turn off the one or more light sources (e.g., co-axis light sources 1101 and 2201). The method can include a process to turn on light sources (e.g., reference light sources 101, 103, and 105) to produce corneal reflections, e.g., configured as two or more perpendicular linear arrays of two or more light sources on the user device at a particular distance from the one or more cameras. The method can include a process to capture a second image or frame of images (e.g., HD images), including video, of the eye to detect light reflected from the eye via the reference light sources as a corneal reflection using the one or more cameras with the imager/camera pixels of interest. The method can include a process to measure the reference light sources coordinates. In some implementations of the method, for example, the turning on and turning off of the retinal retroreflection light sources and the reference light sources for corneal reflections can be implemented concurrently instead of sequentially. In such examples, a single image and/or frame of images can be used to determine the pupil center coordinates and the reference light sources coordinates of the corneal reflections. The method can include a process to compare the pupil center location with the reference points locations. The method can include a process to determine the gazing point of the eye based on the compared locations.

Figure 27:
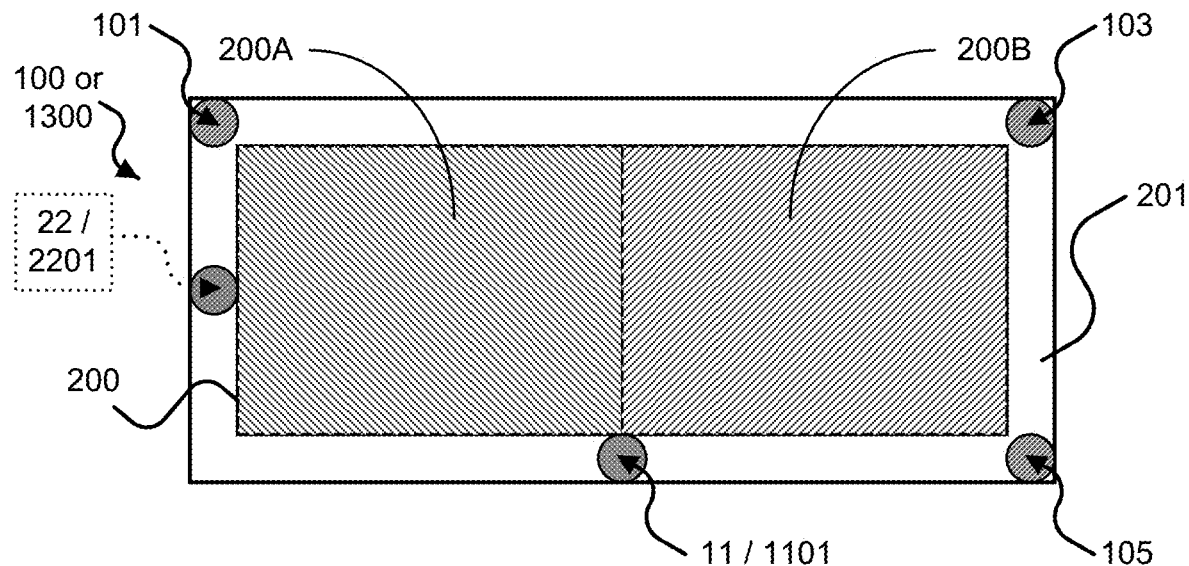
FIG. 27 shows a diagram of a user device including the display screen having a plurality of display regions and an exemplary eye mapping device of the disclosed technology.
Figure 28:
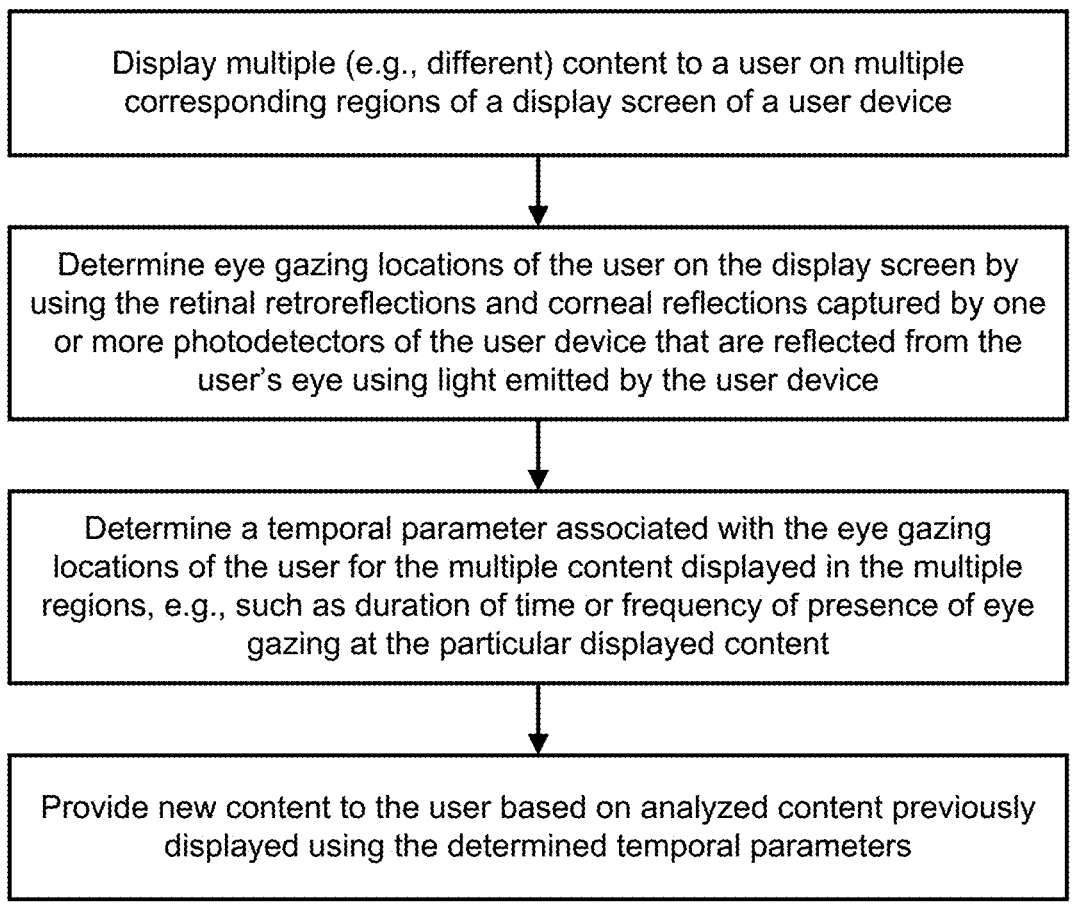
FIG. 28 shows a diagram of an exemplary method to optimize content delivered to a user with a display device using the determined gazing point of the user's eye(s).

In another aspect, the disclosed technology can include a method to optimize content delivered to the user of the user device 201 using the determined gazing point of the user's eye, as shown in FIG. 28. For example, in some implementations, the method can include a process to display a first content message in a first region of a display screen of a user device and display, e.g., concurrently, a second content message different than the first content message in a second region of the display screen. For example, the content messages can include content such as advertisements, entertainment, information and/or news, formed from an image or images, text, audio, and/or video. FIG. 27 shows a diagram of the user device 201 including the display screen 200 having a plurality of display regions, e.g., two display regions including a first region 200A and a second region 200B. The user device 201 shown in FIG. 27 includes one of the exemplary eye mapping devices 100 or 1300. It is understood that the user device can include more than two content display regions to display a variety of differing content simultaneously.

The method includes a process to determine the locations of the user's eye gazing on the display screen of the user device (e.g., display screen 200 of the user device 201 shown in FIG. 27), in which the process determines the eye gazing locations using the disclosed eye mapping technique (e.g., such as that described in FIG. 26) using the retinal retroreflections and corneal reflections captured by one or more photodetectors of the exemplary eye mapping device (e.g., such as device 100 or 1300) that is reflected by the user's eye from the light emitted by the probe light source(s) and reference light sources, respectively. The method includes a process to analyze a temporal parameter of the determined location of the user's eye gazing (e.g., a duration of time and/or frequency of gazing) associated with the first and/or second content messages in the respective first and/or second regions. For example, the analyzed temporal parameter can include how long the user looked at the first and/or second regions of the display screen, as well as, how often the user repeatedly returned to gazing at the first and/or second regions after changing the location of his/her gaze. For example, the analyzed temporal parameter associated with the determined location of the user's gazing can be attributed a level of interest by the user in the content displayed in the display region.

The method can include a process to use the analyzed temporal parameter to determine new content to provide to the user via the display screen of the device. For example, the method can include a process to assess a level of interest based on the analyzed temporal parameter of the user in the respective content messages to provide the new content. In an illustrative example, the first content message can include an advertisement for a sport utility vehicle (SUV) while the second content message can include an advertisement for a compact car. The described method can be used to determine an overall level of interest in one, both, or none of the advertisements based on how long and/or how often the user gazed at the respective advertisements. The method can further include a process to determine a level of preference based on the assessed level of interest. For example, the described method can be used to assess the portions of the advertisement, e.g., spatial portions and/or temporal portions, that captured the longest and/or most frequent attention (e.g., using the temporal parameter associated with the user's eye gazing). For example, the user may have looked longer and/or more frequently at the SUV advertisement, in which he/she gazed more attentively at the front of the SUV rather than at the rear of the SUV. Also for example, the user may have looked longer and/or more frequently at the portion of the SUV advertisement that displayed or discussed the price of the SUV, than, for example, the performance of the SUV.

Figure 29:
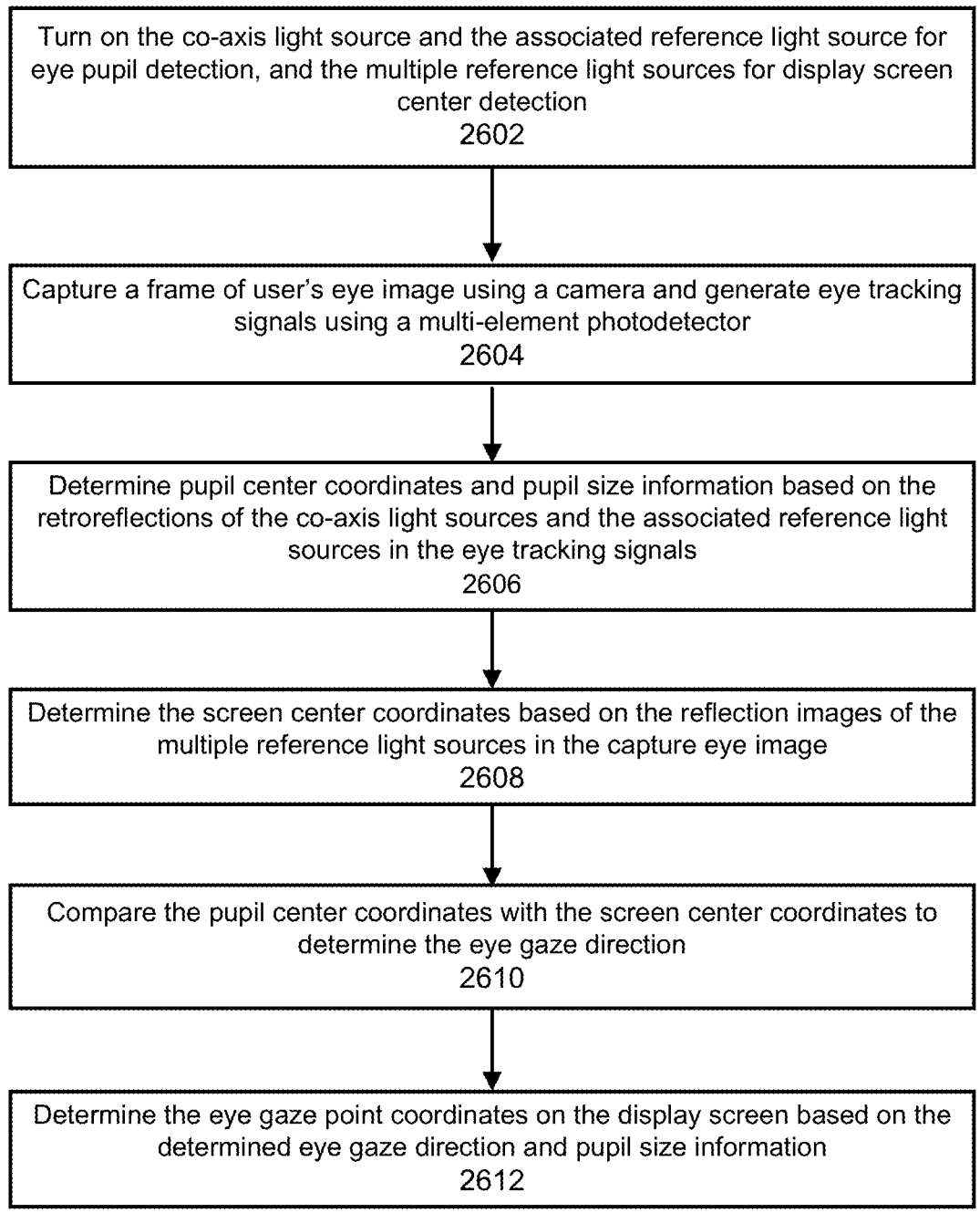
FIG. 29 presents a flowchart illustrating an exemplary process of determining an eye gaze point of a user on a display screen of a device.

FIG. 29 presents a flowchart illustrating an exemplary process of determining an eye gaze point of a user on a display screen of a device. The exemplary process may begin by turning on the light sources, including both multiple reference light sources for display screen center detection, and co-axis light sources and the associated reference light sources for eye pupil detection (2602). The process then captures a frame of user's eye image using a sensor camera and generates eye tracking signals using a multi-element photodetector (2604). Next, the process determines the pupil center coordinates based on the retroreflections of the co-axis light sources and the associated reference light sources in the eye tracking signals (2606). The process also determines the pupil size during process 2606. The process also determines the screen center coordinates based on the reflection images of the multiple reference light sources in the capture eye image (2608). The process then compares the pupil center coordinates with the screen center coordinates to determine the eye gaze direction (2610). Next, the process determines the eye gaze point coordinates on the display screen based on the determined eye gaze direction and pupil size information (2612).

Figure 30:
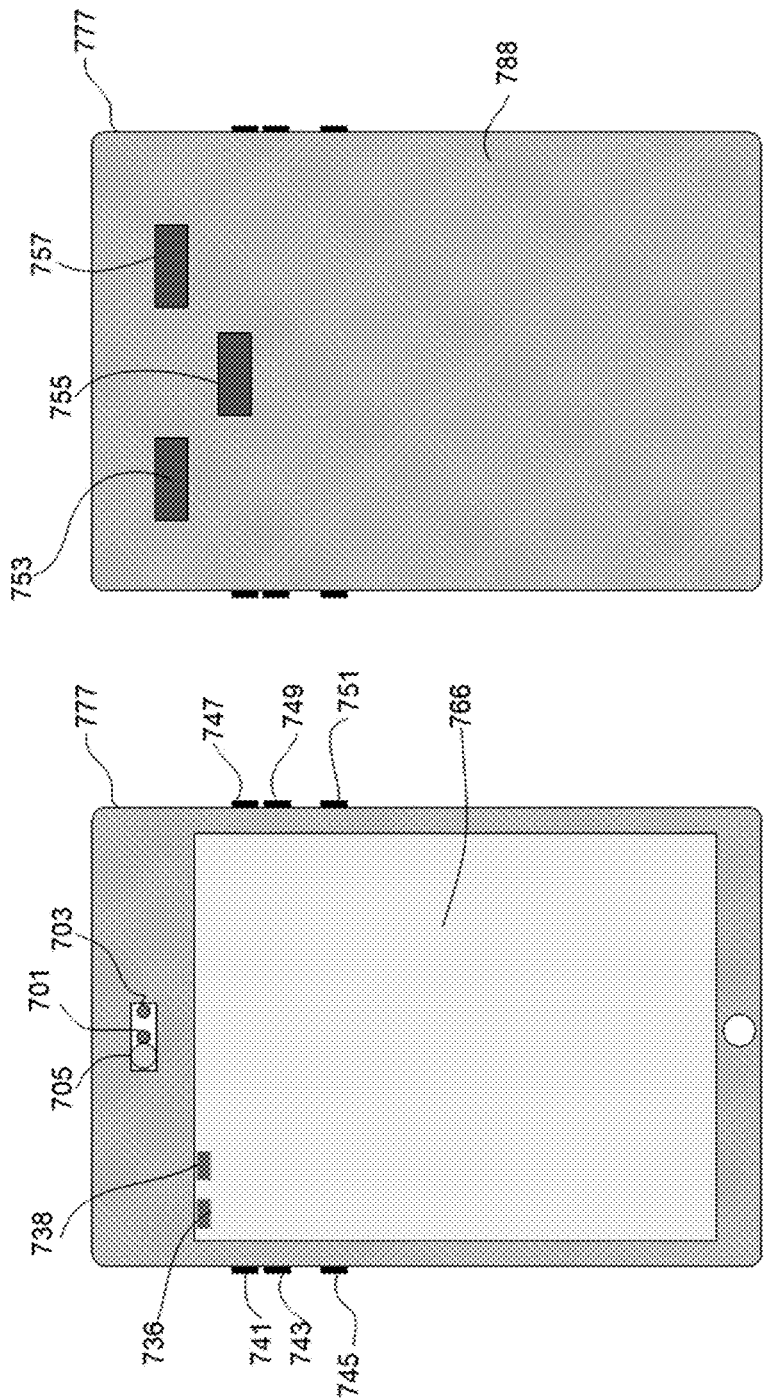
FIG. 30 shows a diagram of an exemplary eye mouse function buttons design on a user mobile device.

FIG. 30 shows a diagram of an exemplary eye mouse function buttons design on a user mobile device. In the example shown, the eye mouse function buttons 741, 743, 745 are designed on the left side of a user mobile device 777. These buttons may be designated with functions of a regular mouse's left click, right click, and middle click respectively. As another example, the eye mouse function buttons 747, 749, 751 are designed on the right side of mobile device 777 and designated with functions of regular mouse's left click, right click, and middle click respectively. In yet another example, the eye mouse function buttons 736 and 738 are designed on the front screen 766 of mobile device 777. In still another example, the eye mouse function buttons 753, 755, 757 are designed on the back side of mobile device 777 and designated with functions of regular mouse's left click, right click, and middle click respectively. In some implementations however, the eye mouse buttons are shared with the existing buttons of the mobile device.

We now consider the attainable resolution of an exemplary eye mouse design. Assuming the distance between the screen of a mobile device and the user's eye is 600 mm, the cornea open angle relative to the screen would be about 1°. Also assume the sensor camera on the mobile device field of version (FOV) is 30°. If the sensor camera has 1.2M pixels resolution, the angular resolution would be about 0.43°. If the sensor camera has 8M pixels resolution, the angular resolution would be about 0.16°. Consequently, by limiting the sensor camera's FOV or by shortening the monitor screen distance to the eye, the resolution of the eye image can be improved. Note that at 600 mm distance, human head corresponds to about 13° open angle, and the separation of the two eyes corresponds to 6° open angle. As such, even about 15° sensor camera FOV would be acceptable for both eyes. In doing so, the resolution can be doubled. Furthermore, if only one eye is tracked with the sensor camera, the resolution can be greatly improved.

Figure 31:
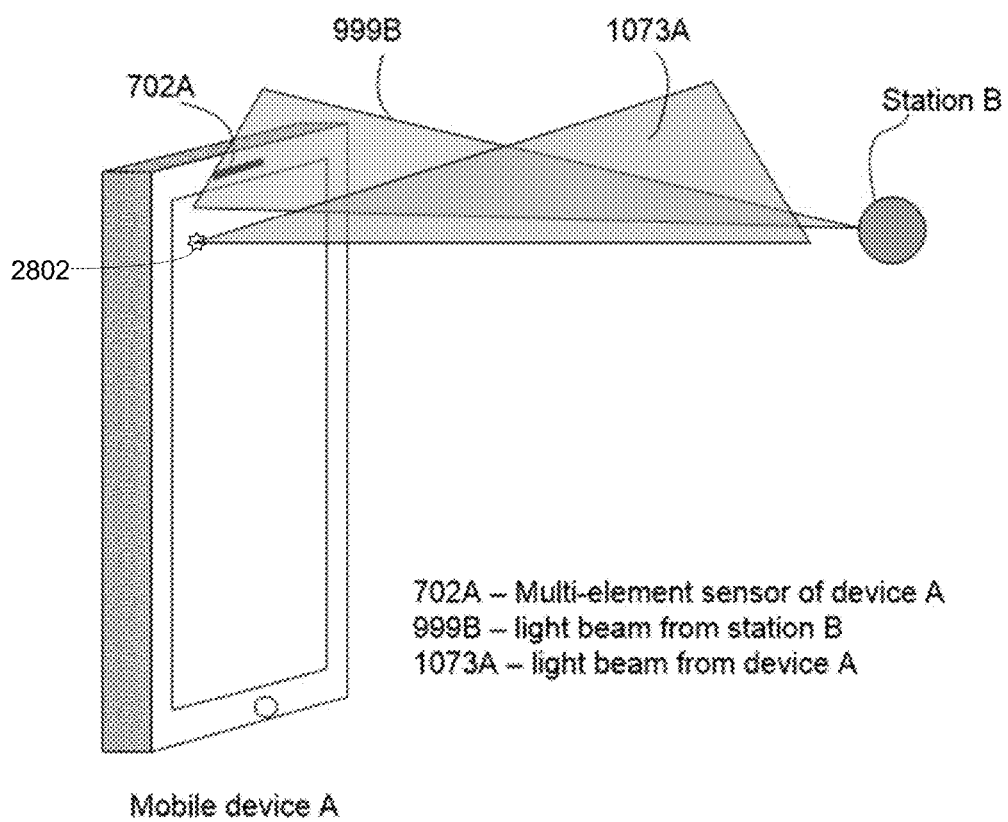
FIG. 31 illustrates a schematic of using the light sources and a multi-element optical sensor on a mobile device A to communicate data information with a station B, such as a second mobile device, which also includes light sources and a multi-element optical sensor.

FIG. 31 illustrates a schematic of using the light sources and a multi-element optical sensor on a mobile device A to communicate data information with a station B, such as a second mobile device, which also includes light sources and a multi-element optical sensor. As can be seen in FIG. 31, mobile device A, which includes a multi-element sensor 702A, and at least one light source 2802, transmits data to station B by emitting a light beam 1073A carrying the data signal toward state B. The multi-element sensor 702A can be used to receive the data carried on a light beam 999B emitted by a light source (not shown) on station B. In some implementations, when multiple light sources exist on each of the devices A and B, different light sources can be used as different communication channels. Moreover, different sensor elements in each multi-element sensor can be used as detectors for the different communication channels. Because optical carrier frequencies are extremely high, high speed communication can be realized between mobile device A and station B, such as another mobile device.

Figure 32:
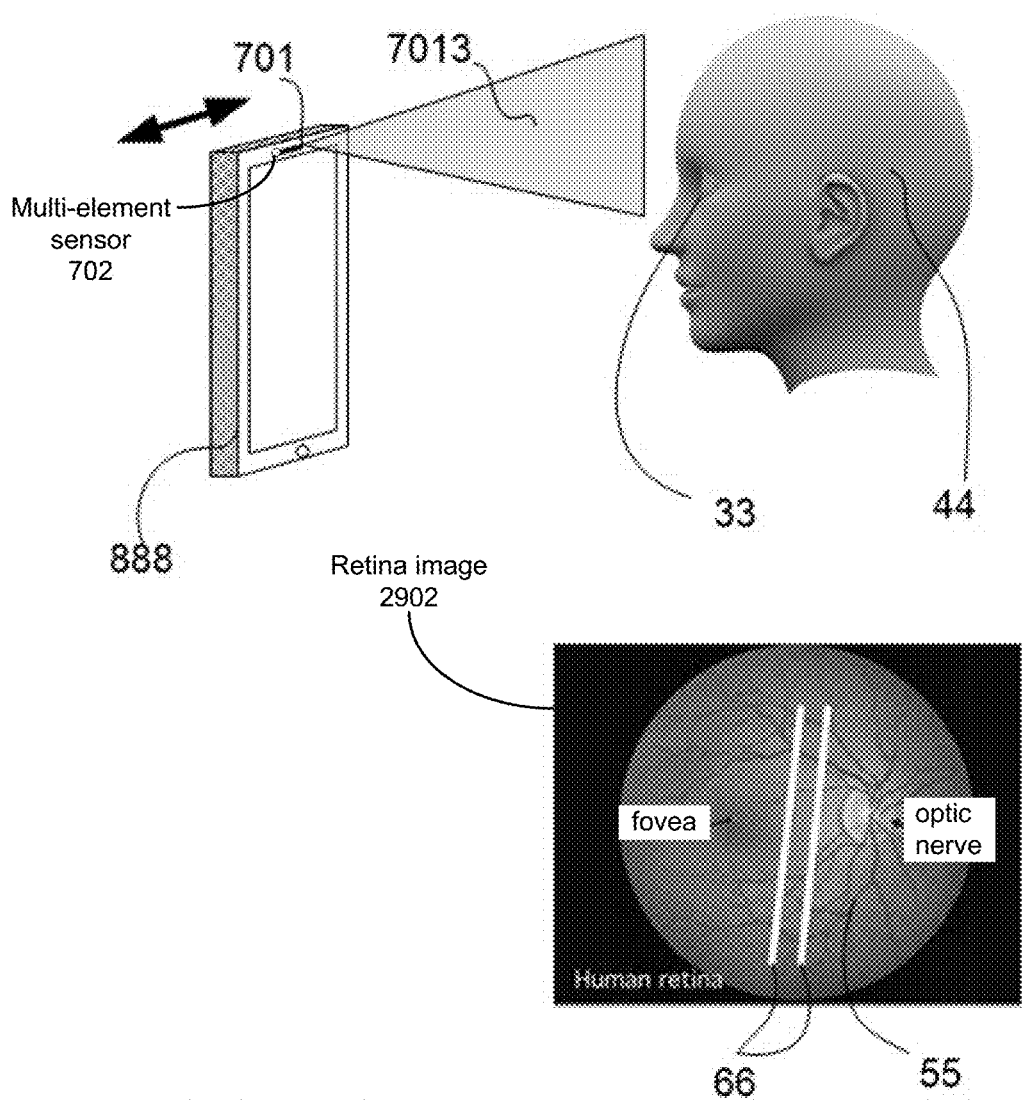
FIG. 32 illustrates a schematic of using the light sources and a multi-element optical sensor on a mobile device for retina scan of a user for security authorization.

FIG. 32 illustrates a schematic of using the light sources and a multi-element optical sensor on a mobile device 888 for retina scan of a user 44 for security authorization. As can be seen in FIG. 32, mobile device 888 includes multiple light sources 701 and a multi-element sensor 702, which is part of the eye pupil detection module of the eye mouse described above. During retina scanning operation, the light sources 701 are scanned across the user 88's eye 33 by either moving device 888 or by moving user 44's head so that the multiple light sources 701 scan across user 44's eyes. As a result, the light sources' image spots on the eye 33's retina are also scanned across the retina. This is illustrated in the inset image 2902 in FIG. 32, wherein the two bright lines are the light spot traces 66 as the two light sources are scanned. The reflectance values from different retina locations are typically different. For example, the blood vessels 55 in the human retina image 2902 typically have different reflectance from the rest of the retina area. Hence, the sensor 701 of device 888 can be used to detect the reflectance difference to form a retina signature/code for user 44. Because every person has a unique retina structure, the obtained retina signature/code of a given user can be used as the security key for that user to be compared with a stored retina signature/code for user authentication.

Figure 33:
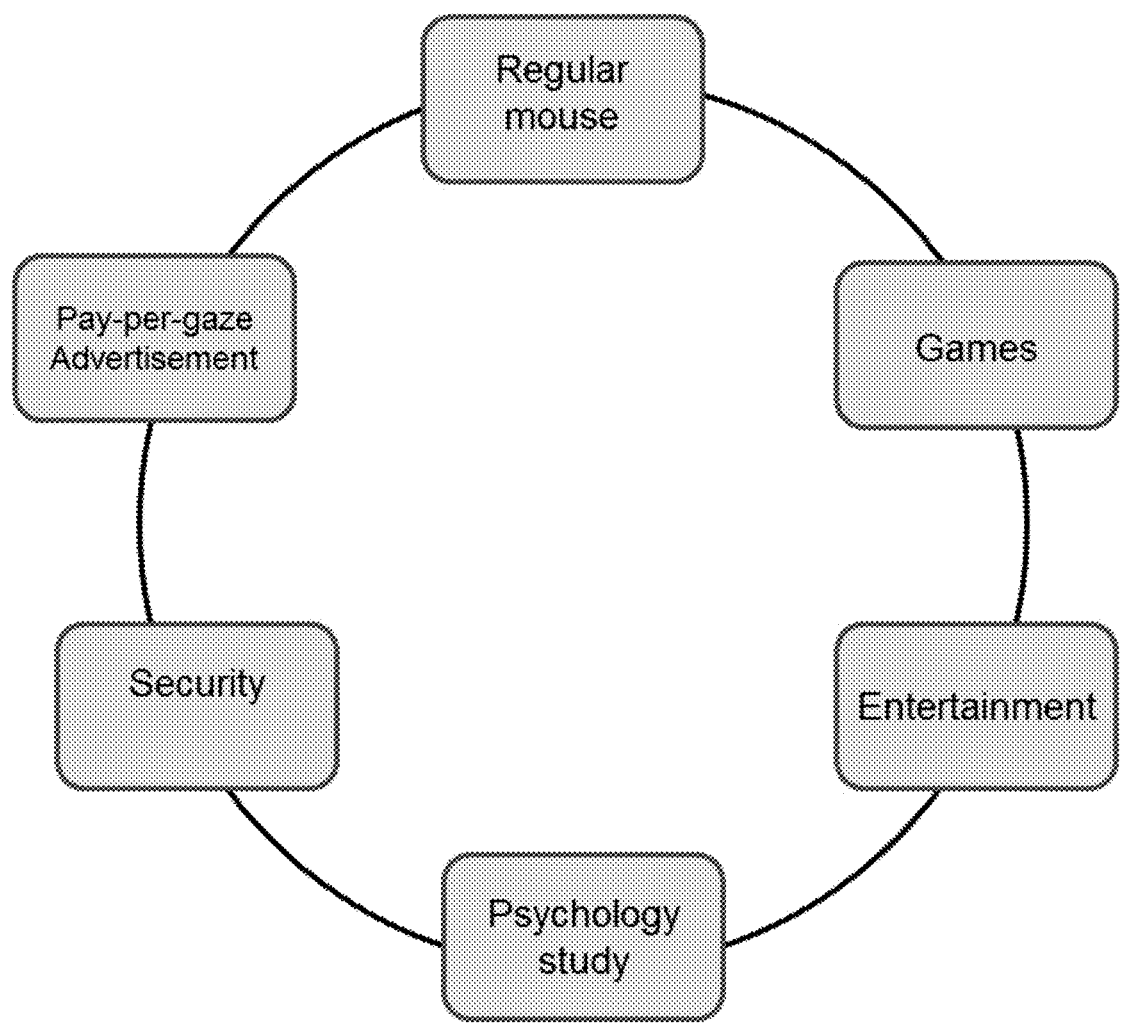
FIG. 33 shows a diagram of the targeted applications of the proposed eye mouse technology.

FIG. 33 shows a diagram of the targeted applications of the proposed eye mouse technology. The proposed eye mouse design has a very small size, high resolution, low cost, and low power consumption. For example, an exemplary eye mouse design can have such a small size as about 2 mm in width, 4 mm in thickness, and 6 mm in length. Such as, the proposed eye mouse module can be easily integrated into small mobile terminals, such as smartphones, tablets, laptops, among others. Moreover, the proposed eye mouse is easy to use because: (1) user does not need to wear any extra tool on his/her head; (1) it allows for one hand operation; and (3) eye blink operation (as confirmation/selection) is made possible. The proposed eye mouse provides an absolute eye gaze point detection technique by comparing the pupil center coordinates with screen center coordinates. Hence, the proposed eye mouse may be calibration free, therefore feeling like a regular optical mouse. The proposed eye mouse is also friendly for further development. For example, the eye mouse may also be developed with high-speed data communication function so that it can transmit and receive data among multiple mobile terminals without signal leakage to non-concerned user. Because of the above unique features, the proposed eye mouse technology is suitable for a wide range of applications.

For example, the eye mouse can be used as regular mouse, and can be used to play computer games. The eye mouse's eye gaze detection function may be used for pay-per-gaze advertisements. As another example, the eye mouse's pupil size detection may be used to collect customer reaction data that is useful for advertisement management, games developer etc.

In one example, the eye mouse may be used in security access, including as a retina scanner. More specifically, when the user moves the eye mouse across his/her eyes, the light sources and the sensor detectors take the user's eye retina reflection properties which can be used to generate passcodes. In another example, the eye mouse is used in security typing. More specifically, when the user types the letters with the eye, people nearby cannot know which letters the user picks. The eye mouse can also be used in psychology studies. More specifically, a designed series of questions, pictures, or videos may be presented to the user, and the eye mouse sensor measures the user's eye reactions in response to the questions, pictures, or videos. The collected information may help the psychologist to investigate the user's true thoughts.

As another example, the eye mouse may be used in entertainment such as spy camera finding. In a further example, with the equipped light sources and the sensor detectors, the proposed eye mouse can be used to transmit and receive data among other mobile devices which are equipped with same type of eye mouse. Furthermore, this proposed eye mouse technology may also find applications for providing disabled people who cannot handle regular mouse and keyboards with an alternative to control a computer cursor.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed are techniques and structures as described and shown, including:

1. A method for controlling a cursor on a display screen based at least partly on detection of an eye gaze of a user with respect to the display screen, comprising:
   presenting a display interface on the display screen to the user;
   emitting a first modulated light from a first group of light sources positioned to be coaxial with a photodetector, wherein the first modulated light is modulated according to a first frequency;
   emitting a second modulated light from a second group of light sources positioned along a periphery of a display screen, wherein the second modulated light is modulated according to a second frequency, wherein the second frequency is a different frequency from the first frequency;
   generating, by the photodetector positioned to receive a first light from the first group of light sources retroreflected from a retina of an eye, a first signal;
   receiving, by the photodetector, images of reflections of the second group of light sources from a cornea of the eye;
   demodulating the first signal according to the first frequency to generate a first demodulated signal;
   demodulating the second modulated light in the images according to the second frequency to generate demodulated images;
   processing the first demodulated signal to determine first center coordinates of a pupil of the eye;
   processing the demodulated images to determine second center coordinates of the display interface on the eye, wherein the second center coordinates of the display interface on the eye are determined from a center location of the images of reflections of the second group of light sources from the cornea;
   comparing the determined first center coordinates and the determined second center coordinates to determine a gaze point of the eye on the display interface, wherein in a case that the first center coordinates are below the second center coordinates, the gaze point is below a center of the display screen, and in another case that the first center coordinates are above the second center coordinates, the gaze point is above the center of the display screen; and
   displaying, on the display interface, the cursor based on the determined gaze point.

2. The method of claim 1, wherein the first group of light sources is modulated according to a first modulation and the second group of light sources is modulated according a second modulation, wherein the first modulation and the second modulation differ in at least a frequency, and wherein the eye pupil center coordinates and the screen center coordinates are determined at substantially the same time.

3. The method of claim 1, further comprising:
   adjusting a position of the cursor on the display screen based on updated coordinates of the gaze point.

4. The method of claim 1, wherein a first and a second scattered lights are generated when the first and second modulated lights scatter off a face and other surfaces near the face.

5. The method of claim 4, wherein the first frequency at which the first group of light sources is modulated is the same as the second frequency at which the second group of light sources is modulated, and wherein the first modulation and the second modulation differ by a phase of 180 degrees.

6. A portable device for high speed communication with another portable device, comprising:
   a front panel including a display screen;
   a first group of light sources positioned to be coaxial with a multi-element sensor and positioned outside the display screen, the first group of light sources configured to emit first modulated light modulated at a first frequency;
   a second group of light sources positioned along a periphery of the display screen and positioned inside the display screen, the second group of light sources configured to emit second modulated light modulated at a second frequency, wherein at least one light source of the first group or the second group is operable to transmit data to the other portable device by emitting a light beam carrying a data signal toward the other portable device,
   wherein the multi-element sensor is positioned on the front panel outside of the display screen, wherein the multi-element sensor is configured to receive a light beam carrying another data signal emitted by the other portable device, wherein the multi-element sensor is positioned to receive a first light from the first group of light sources retroreflected from a retina of an eye, wherein a signal representative of the first modulated light retroreflected from the retina is demodulated according to the first frequency rejecting signals not modulated at the first frequency, and from the demodulated signal first center coordinates of a pupil of the eye are determined, wherein second center coordinates of the display screen on the eye are determined from a center location of images of reflections of the second group of light sources from a cornea of the eye, and wherein second signals corresponding to the images are demodulated according to the second frequency rejecting signals not modulated at the second frequency, and wherein a gaze point of the eye on the display screen is determined by comparing the first center coordinates to the second center coordinates.

7. The portable device of claim 6, wherein more than one of the first group and the second group of light sources is used as a different communication channel for data transmission.

8. The portable device of claim 7, wherein different sensor elements in the multi-element sensor represent detectors for the different communication channels.

9. The portable device of claim 6, wherein the first group and the second group of light sources and the multi-element sensor are collectively used to perform eye pupil detection and eye-track functions.

10. The portable device of claim 6, wherein the portable device includes a mobile phone.

11. The portable device of claim 6, wherein the portable device includes a tablet computer.

12. The portable device of claim 6, wherein the portable device includes a portable computer.

13. The portable device of claim 6, wherein the portable device includes a laptop.

14. The portable device of claim 6, wherein in a case that the first center coordinates are below the second center coordinates, the gaze point is below a center of the display screen, and in another case that the first center coordinates are above the second center coordinates, the gaze point is above the center of the display screen.

* * * * *